US011548886B2

(12) United States Patent
Raimundo et al.

(10) Patent No.: US 11,548,886 B2
(45) Date of Patent: Jan. 10, 2023

(54) MONOCYCLIC COMPOUNDS USEFUL AS GPR120 MODULATORS

(71) Applicant: Valo Health, Inc., Boston, MA (US)

(72) Inventors: Brian Raimundo, Boston, MA (US); Elena S. Koltun, Boston, MA (US); John Griffin, Boston, MA (US); Eric Stangeland, Boston, MA (US)

(73) Assignee: Valo Health, Inc., Boston, MA (US)

( * ) Notice: Subject to any disclaimer, the term of this patent is extended or adjusted under 35 U.S.C. 154(b) by 0 days.

(21) Appl. No.: 16/998,660

(22) Filed: Aug. 20, 2020

(65) Prior Publication Data

US 2021/0101896 A1 Apr. 8, 2021

Related U.S. Application Data

(63) Continuation of application No. 16/331,916, filed as application No. PCT/US2017/050956 on Sep. 11, 2017, now Pat. No. 10,800,773.

(60) Provisional application No. 62/393,616, filed on Sep. 12, 2016.

(51) Int. Cl.
| | | |
|---|---|---|
| C07D 417/14 | (2006.01) | |
| C07D 401/14 | (2006.01) | |
| C07D 401/04 | (2006.01) | |
| C07D 417/04 | (2006.01) | |
| A61P 25/28 | (2006.01) | |
| A61P 1/16 | (2006.01) | |
| A61P 3/10 | (2006.01) | |
| A61P 25/16 | (2006.01) | |
| A61P 29/00 | (2006.01) | |
| C07D 471/04 | (2006.01) | |

(52) U.S. Cl.
CPC .............. *C07D 417/14* (2013.01); *A61P 1/16* (2018.01); *A61P 3/10* (2018.01); *A61P 25/16* (2018.01); *A61P 25/28* (2018.01); *A61P 29/00* (2018.01); *C07D 401/04* (2013.01); *C07D 401/14* (2013.01); *C07D 417/04* (2013.01); *C07D 471/04* (2013.01)

(58) Field of Classification Search
CPC .. C07D 417/14; C07D 401/04; C07D 401/14; C07D 417/04; C07D 471/04
USPC ........................................................ 514/274
See application file for complete search history.

(56) References Cited

U.S. PATENT DOCUMENTS

| | | | |
|---|---|---|---|
| 2,735,225 A * | 2/1956 | Goodhue et al. .... | C07D 239/42 47/57.5 |
| 5,350,761 A | 9/1994 | Van Duzer et al. | |
| 5,411,978 A | 5/1995 | Ladislas et al. | |
| 6,716,836 B2 | 4/2004 | Ogilvie et al. | |
| 8,110,681 B2 | 2/2012 | Heemskerk et al. | |
| 9,562,053 B2 | 2/2017 | Sui et al. | |
| 2009/0275578 A1 | 11/2009 | Clayton et al. | |
| 2010/0035944 A1 | 2/2010 | Epple et al. | |
| 2011/0245247 A1 | 10/2011 | Braje et al. | |
| 2011/0312976 A1 | 12/2011 | Arakawa et al. | |
| 2011/0313003 A1 | 12/2011 | Shi et al. | |
| 2014/0275182 A1 | 9/2014 | Sui et al. | |
| 2015/0274672 A1 | 10/2015 | Chelliah et al. | |
| 2015/0291527 A1 | 10/2015 | Kim et al. | |
| 2015/0322044 A1 | 11/2015 | Jurica et al. | |
| 2019/0047990 A1 | 2/2019 | Berdini et al. | |
| 2019/0202821 A1 | 7/2019 | Raimundo et al. | |

FOREIGN PATENT DOCUMENTS

| | | |
|---|---|---|
| CN | 101500995 A | 8/2009 |
| CN | 105209444 A | 12/2015 |
| DE | 22 53 251 A1 | 5/1974 |
| EP | 0 145 078 A2 | 6/1985 |
| EP | 0 526 402 A1 | 2/1993 |
| EP | 0 548 934 A1 | 6/1993 |
| EP | 2 172 198 A1 | 4/2010 |
| JP | H641104 A | 2/1994 |
| JP | 2004-523590 A | 8/2004 |
| JP | 2014-533736 A | 12/2014 |
| JP | 2016-141618 A | 8/2016 |
| WO | WO-02/076982 A2 | 10/2002 |
| WO | WO-2013/079452 A2 | 10/2002 |
| WO | WO-03/033480 A1 | 4/2003 |
| WO | WO-2005/037779 A2 | 4/2005 |
| WO | WO-2006/020879 A1 | 2/2006 |
| WO | WO-2006/038594 A1 | 4/2006 |
| WO | WO-2007/109211 A2 | 9/2007 |
| WO | WO-2010/048207 A2 | 4/2010 |
| WO | WO-2010/080537 A1 | 7/2010 |
| WO | WO-2010/104195 A1 | 9/2010 |
| WO | WO-2011/159297 A1 | 12/2011 |
| WO | WO-2013/011402 A1 | 1/2013 |
| WO | WO-2014/086663 A1 | 6/2014 |
| WO | WO-2014/096941 A1 | 6/2014 |
| WO | WO-2014/209034 A1 | 12/2014 |

(Continued)

OTHER PUBLICATIONS

Murray et al. Biomedical Mass Spectrometry (1982), 9 (11), 466-72.*
Song et al. Chemical Biology & Drug Design (2015), 85(3), 306-314.*
Ke et al. European Journal of Medicinal Chemistry (2014), 83, 226-235.*
Kita et al. Biological & Pharmaceutical Bulletin (2001), 24(7), 860-862.*
Choi, et al., "Synthesis of aristolactam analogues and evaluation of their antitumor activity", Bioorganic & Medicinal Chemistry Letters, vol. 19, No. 11, Apr. 10, 2009, pp. 3036-3040.
Extended European Search Report dated Feb. 12, 2020, from application No. 17849719.4.

(Continued)

*Primary Examiner* — Kahsay Habte
(74) *Attorney, Agent, or Firm* — Foley & Lardner LLP

(57) ABSTRACT

Provided herein are compounds, compositions including them, and methods of modulating GPR120 activity and treating diseases mediated by GPR120 by administering such compounds and compositions.

10 Claims, 1 Drawing Sheet

(56) References Cited

FOREIGN PATENT DOCUMENTS

| WO | WO-2015/150565 A1 | 10/2015 |
|---|---|---|
| WO | WO-2016/033436 A1 | 3/2016 |

OTHER PUBLICATIONS

Extended European Search Report dated Mar. 30, 2020, from application No. 17849722.8.
Fells, et al., "2D binary QSAR modeling of LPA3 receptor antagonism", Journal of Molecular Graphics and Modelling, vol. 28, No. 8, Jun. 1, 2010, pp. 828-833.
Fells, et al., "Structure-based drug design identifies novel LPA3 antagonists", Bioorganic & Medicinal Chemistry, vol. 17, No. 21, Nov. 1, 2009, pp. 7457-7464.
Final Office Action dated Mar. 20, 2020, from U.S. Appl. No. 16/331,928.
Fuccella, et al., "Fate of the Analgesic and Anti-Inflammatory Drug K 4277 after Oral Administration to Man", European Journal of Clinical Pharmacology, vol. 6, No. 4, Dec. 1, 1973, pp. 256-260.
Golbraikh, et al., "Validation of protein-based alignment in 3D quantitative structure-activity relationships with CoMFA models", European Journal of Medicinal Chemistry, vol. 35, No. 1, Jan. 1, 2000, pp. 123-136.
Hussein, et al., "Synthesis and Structural Investigation of N-Pyridyl-1, 3-Dihydroxyisoindolines", Asian Journal of Chemistry, vol. 3, No. 1, Jan. 1, 1991, pp. 30-37.
International Preliminary Report on Patentability dated Oct. 2, 2018, from application No. PCT/US2017/050964.
International Search Report and Written Opinion dated Nov. 21, 2017, from application No. PCT/US2017/050964.
International Search Report and Written Opinion dated Nov. 27, 2017, from application No. PCT/US2017/050956.
Lorion, et al., "Complementary Synthetic Approaches to Constitutionally Diverse N-Amino-alkylated Isoindolinones: Application to the Synthesis of Falipamil and 5-HT1A Receptor Ligand Analogues", Synthesis, vol. 2009, No. 11, Apr. 14, 2009, pp. 1897-1903.
National Center for Biotechnology Information. PubChem Database. SR-05000020926, Source=The Scripps Research Institute Molecular Screening Center, SID=174009379, https://pubchem.ncbi.nlm.nih.gov/substance/174009379 (accessed on Feb. 11, 2020). Available on Mar. 21, 2015, 7 pages.
Non-Final Office Action dated Nov. 4, 2019, from U.S. Appl. No. 16/331,916.
Non-Final Office Action dated Sep. 9, 2019, from U.S. Appl. No. 16/331,928.
Norcross, et al., "Trisubstituted Pyrimidines as Efficacious and Fast-Acting Antimalarials", Journal of Medicinal Chemistry, vol. 59, No. 13, Jun. 17, 2016, pp. 6101-6120.
Notice of Allowance dated Feb. 10, 2020, from U.S. Appl. No. 16/331,916.
Notice of Allowance dated May 28, 2020, from U.S. Appl. No. 16/331,916.
Sabatucci, et al., "Substituted 4-hydroxyphenyl sulfonamides as pathway-selective estrogen receptor ligands", Bioorganic & Medicinal Chemistry Letters 16 (2006) 854-858.
Selvakumar, et al., "Synthesis of Condensed Tetrahydroisoquinoline Class of Alkaloids by Employing TfOH-Mediated Imide Carbonyl Activation", European Journal of Organic Chemistry, vol. 2015, No. 10, Apr. 1, 2015, pp. 2175-2188.
Sparks, et al., "Identification of diarylsulfonamides as agonists of the free fatty acid receptor 4 (FFA4/GPR120)", Bioorganic & Medicinal Chemistry Letters, vol. 24, Issue 14, Jul. 15, 2014, pp. 3100-3103.
STN Registry Database, Record for Registry No. RN 1252377-76-6, Entered into STN on Nov. 10, 2010, 1 page.
Witty, et al., "Discovery of potent and stable conformationally constrained analogues of the MCH R1 antagonist SB-568849", Bioorganic & Medicinal Chemistry Letters, vol. 16, No. 18, Jul. 12, 2006, pp. 4872-4878.
Mancilla-Percino, et al., "Isoindoline Derivatives of alpha-Amino Acids as Cyclooxygenase 1 and 2 Inhibitors," Arch. Pharm. Chem. Life Sci., 2016, 349, pp. 175-185.
Registry (STN) D 1935530-23-6 [online], Oct. 7, 2011-Jun. 20, 2016 [date of retrieval: Mar. 1, 2021].
RN: 1334634-35-3, Chemical Abstracts Service, STN Registry, Oct. 7, 2011.
RN: 1440520-62-6, Chemical Abstracts Service, STN Registry, Jun. 24, 2013.

* cited by examiner

MONOCYCLIC COMPOUNDS USEFUL AS GPR120 MODULATORS

CROSS-REFERENCE CROSS REFERENCED TO RELATED PATENT APPLICATIONS

This application is a continuation of U.S. application Ser. No. 16/331,916, filed Mar. 8, 2019, which is a national stage entry under 35 U.S.C. § 371 of International Application No. PCT/US2017/050956, filed Sep. 11, 2017, which in turn claims priority from Provisional U.S. Application Ser. No. 62/393,616, filed Sep. 12, 2016, the contents each of which are hereby incorporated by reference in their entireties.

FIELD OF THE INVENTION

The present invention provides compositions and methods for modulating the GPR120 receptor, and generally relates to the fields of medicinal chemistry, medicine, pharmacology, molecular biology, and biology. Compounds modulating the GPR120 receptor are useful for treating various metabolic and inflammatory diseases, including but not limited to, type 2 diabetes, obesity, hepatic steatosis, and Alzheimer's, and one or more symptoms of each thereof.

BACKGROUND OF THE INVENTION

Type 2 diabetes (T2D) is a chronic disease resulting from the body's inefficient use of the insulin it produces. The states of hyperglycemia and insulin resistance observed in T2D typically result from excess weight and lack of physical exercise. Because obesity and sedentary lifestyles are increasing worldwide, the incidence of T2D is also rapidly increasing. The World Health Organization (WHO) estimates that more than 300 million people worldwide have T2D, and that more than 1 million deaths per year can be directly attributed googleto T2D. WHO furthermore projects that diabetes-associated deaths will increase by 50% over the next decade. Current therapeutic strategies for T2D include treatment with agents that target the secretion or utilization of insulin. However, these strategies do not work or do not work well for all patients, and new strategies and agents are needed for treatment of the multiple aspects of T2D pathology.

GPR120, also known as free fatty acid receptor 4 (FFA4), is a 7-transmembrane-spanning G-protein coupled receptor that is activated by long-chain free fatty acids including the ω-3 fatty acids. GPR120 is expressed in a wide range of tissues and mediates multiple effects associated with energy balance and inflammation. In enteroendocrine cells, activation of GPR120 leads to secretion of the incretins glucagon-like peptide-1 (GLP-1) and gastric inhibitory peptide (GIP), which in turn stimulate release of insulin from pancreatic beta cells. Activation of GPR120 in adipocytes stimulates glucose uptake and adipogenesis while inhibiting lipolysis. Activation of GPR120 in macrophages exerts anti-inflammatory effects, inhibiting the release of cytokines including TNF-α and IL-6. In enteroendocrine cells and adipocytes, GPR120 signaling proceeds through Gq/11, but in macrophages GPR120 signaling proceeds through the β-arrestin pathway. Dysfunction in GPR120 has been associated with diabetes and obesity in both mice and humans. Accordingly, GPR120 agonists have been tested for the treatment of T2D and other metabolic diseases.(1-4)

Hepatic steatosis is a state of inflammation and cell injury associated with the accumulation of fat in the liver. In cases not related to alcohol intake, the disease is known as non-alcoholic steatohepatitis (NASH). NASH is increasingly common, can lead to liver cirrhosis or liver failure, and is often observed in people with obesity, glucose intolerance, or dyslipidemia. Recent studies utilizing wild type and GPR120 deficient mice confirm a positive role for GPR120 in controlling lipid metabolism, triglyceride and diacylglycerol levels, and inflammatory markers. Consistent with these results, a study of children with nonalcoholic fatty liver disease who were treated with the GPR120 agonist docosahexaenoic (DHA) acid resulted in reduced liver damage and inflammatory macrophages, and increased GPR120 hepatocyte expression.(5a).

Alzheimer's disease (AD) is the most common cause of dementia in the elderly, with an estimated 47M cases worldwide at present and an expectation for more than 130M cases by 2050. Recently it has been demonstrated that activation of GPR120 exerts anti-inflammatory effects in immortalized hypothalamic neurons,(6a) and that GPR120 and another long chain free fatty acid receptor, GPR40 (FFA1), control energy homeostasis and inflammation in the mouse hypothalamus (7a). NLRP3 inflammasome activity has been shown to contribute to pathology in APP/PS1 mice (8a). Omega-3 fatty acids block activation of NLRP3 inflammasomes in macrophages, thereby inhibiting downstream activation of caspase-1 and maturation and release of interleukin-1beta (IL-1beta) (9a). Expression of NLRP1 inflammasomes is also upregulated in the brains of APP/PS1 mice, and Aβ induces NLRP1- and caspase-1 dependent pyroptosis in cultured cortical neurons from these animals (10a). Levels of inflammasome-activated caspase-1 are strongly enhanced in the brains of humans with mild cognitive impairment and AD, and activation of NLRP1 in cultured human neurons induces axonal degeneration (11a). Accordingly, GPR120 agonists hold promise as disease-modifying therapeutics for AD, Parkinson's disease, frontotemporal dementia (FTD), amyotrophic lateral sclerosis (ALS), multi-system atrophy (MSA) and other disorders associated with neuroinflammation.

The present invention provides novel compounds, compositions of matter, particularly pharmaceutical compositions, methods for the synthesis or preparation of the compounds and compositions, and methods for using them to modulate GPR120 and treat T2D, hepatic steatosis, Alzheimer's, and other disease associated with metabolic dysfunction and inflammation.

SUMMARY OF THE INVENTION

The present invention provides, in certain aspects, compounds, compositions of matter (particularly pharmaceutical compositions), methods for the synthesis or preparation of the compounds and compositions, and methods for using them to modulate GPR120.

Provided herein are compounds, compositions including them, and methods of modulating the GPR120 receptor and treating diseases by administering such compounds and compositions.

The first aspect of the present invention provides compounds of Formula I that in various embodiments comprise a bicyclic core element containing a 6-membered heteroaromatic ring with 1-3 ring nitrogen atoms and up to 3 ring substituents:

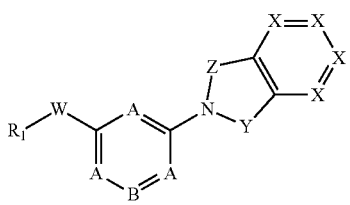

Formula I as well as tautomers, isotopomers and stereoisomers thereof, and prodrugs of any of the foregoing, and pharmaceutically acceptable salts and solvates of all of the foregoing, wherein each A is independently N or CH; B is N or $CR_2$, with the provision that at least one of A or B is N; W is a covalent bond or O; each X independently is CH, $CR_3$ or N wherein $R_3$ is halogen, alkyl, alkoxy, or CN; Y is $SO_2$, CO, $CH_2$, or —C(CH$_3$)$_2$—, or —CH(CH$_3$)—; Z is —CH$_2$—, —CH(CH$_3$)—, —C(CH$_3$)$_2$—, —C(CH$_2$CH$_2$)— (cyclopropano), CO, —(CO)CH$_2$—, —CH$_2$CH$_2$—, or —CHCH—; $R_1$ is an optionally substituted alkyl group, an optionally substituted 3-7 membered cycloalkyl or heterocyclyl group, or an optionally substituted aryl or heteroaryl group; $R_2$ is H, halogen, CN, $OCH_3$, $OCF_3$, NHAc, an optionally substituted alkyl group, an optionally substituted amido group, an optionally substituted cycloalkyl or heterocyclyl group, or an optionally substituted aryl or heteroaryl group. As used herein, an amido includes carboxamido and a sulfonamide group.

The compounds of Formula I are contemplated to stimulate release of GLP-1, GIP and/or glucagon, inhibit release of ghrelin, stimulate glucose uptake and/or exert anti-inflammatory effects, and thereby exert therapeutic effects in T2D. In another aspect, provided herein is a method for agonizing GPR120, comprising contacting the GPR120 with a compound or the composition provided or disclosed herein.

In another aspect, provided herein is a method for modulating metabolism in a mammal, comprising contacting GPR120 in the mammal with an amount of the compound provided herein that is effective to modulate metabolism in the mammal. In another aspect, provided herein is a method for modulating metabolism in a mammal, comprising administering to the mammal an amount of the composition provided herein that is effective to modulate metabolism in the mammal.

In another aspect, provided herein is a method for reducing inflammation in a mammal, comprising contacting GPR120 in the mammal with an amount of the compound provided herein that is effective to reduce the inflammation. In another aspect, provided herein is a method for reducing inflammation in a mammal, comprising administering to the mammal an amount of the composition provided herein that is effective to reduce the inflammation.

In another aspect, provided herein is a method for reducing neuroinflammation in a mammal, comprising contacting GPR120 in the mammal with an amount of the compound provided herein that is effective to reduce the neuroinflammation. As used herein, neuroinflammation refers to inflammation of the nervous tissue. In another aspect, provided herein is a method for reducing neuroinflammation in a mammal, comprising administering to the mammal an amount of the composition provided herein that is effective to reduce neuroinflammation.

In another aspect, provided herein is a method for treating diabetes, pre-diabetes or metabolic syndrome, or one or more symptoms of each thereof in a mammal, comprising contacting GPR120 in the mammal with a therapeutically effective amount of the compound provided herein. In another aspect, provided herein is a method for treating diabetes, pre-diabetes or metabolic syndrome, or one or more symptoms of each thereof in a mammal, comprising administering to the mammal a therapeutically effective amount of the composition provided herein.

In another aspect, provided herein is a method for treating steatohepatitis in a mammal, comprising contacting GPR120 in the mammal with a therapeutically effective amount of the compound provided herein. In another aspect, provided herein is a method for treating steatohepatitis in a mammal, comprising administering to the mammal a therapeutically effective amount of the composition provided herein.

In another aspect, provided herein is a method for treating non-alcoholic steatohepatitis in a mammal, comprising contacting GPR120 in the mammal with a therapeutically effective amount of the compound provided herein. In another aspect, provided herein is a method for treating non-alcoholic steatohepatitis in a mammal, comprising administering to the mammal a therapeutically effective amount of the composition provided herein.

In another aspect, provided herein is a method for treating a disorder associated with, leading to, or resulting from neuroinflammation in a mammal, comprising contacting GPR120 in the mammal with a therapeutically effective amount of the compound provided herein. In another aspect, provided herein is a method for treating a disorder associated with leading to, or resulting from neuroinflammation in a mammal, comprising administering to the mammal a therapeutically effective amount of the composition provided herein.

In another aspect, provided herein is a method for treating Alzheimer's disease, Parkinson's disease, frontotemporal dementia, amyotrophic lateral sclerosis or multi-system atrophy, or one or more symptoms of each thereof, comprising contacting GPR120 in the patient with a therapeutically effective amount of the compound provided herein.

In another aspect, provided herein is a method for treating Alzheimer's disease, Parkinson's disease, frontotemporal dementia, amyotrophic lateral sclerosis or multi-system atrophy, or one or more symptoms of each thereof, comprising administering to the patient a therapeutically effective amount of the composition provided herein.

DETAILED DESCRIPTION OF THE INVENTION

Figure 1:
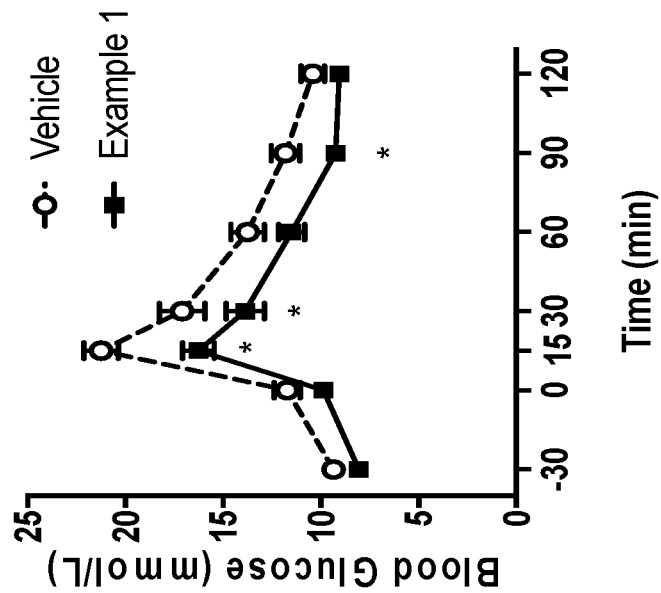
FIG. 1 Anti-Inflammatory activity in LPS-Stimulated human peripheral blood mononuclear cells.
Figure 2:
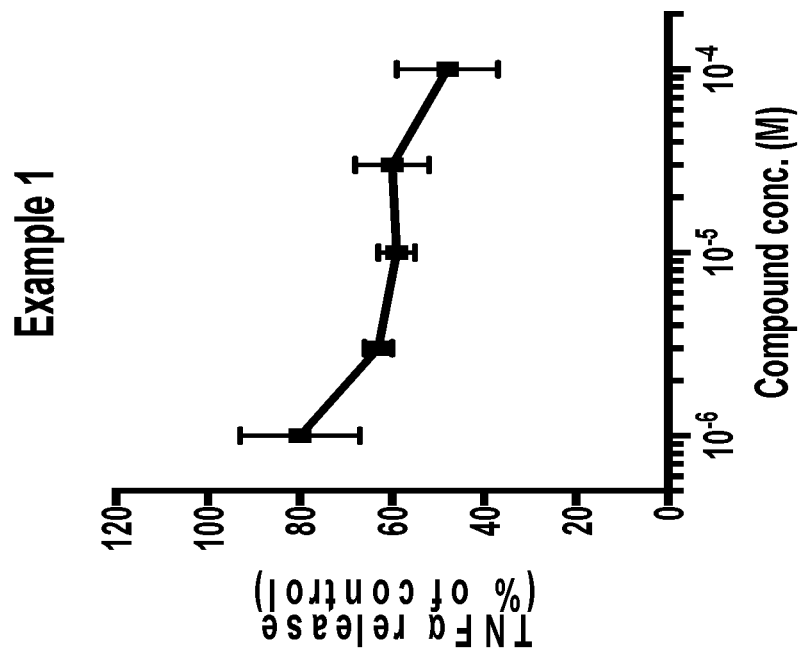
FIG. 2 αTNF levels as a function of drug concentration.

To aid the reader in understanding the invention, how it is made and used, and the benefits thereof, the following usages and definitions are provided.

All technical and patent publications cited herein are incorporated herein by reference in their entirety.

All numerical designations, e.g., pH, temperature, time, concentration, and molecular weight, including ranges, are approximations which may be varied (+) or (−) by increments of, e.g., 0.1 or 1. Thus, all numerical designations may be interpreted by the reader as preceded by the term "about". Similarly, the reagents described herein are merely exemplary; generally, the artisan of ordinary skill will appreciate that equivalents of such are known in the art. As used in the specification and claims, the singular forms "a", "an" and "the" should be interpreted as inclusive of plural references unless the context clearly dictates otherwise.

"Acyl" refers to a group of formula —CO—$R_x$ wherein $R_x$ is H, or is optionally substituted alkyl, cycloalkyl, heterocyclyl, aryl, or heteroaryl. Examples of acyl groups include, for example, —CHO, —CO-Me, and —CO-Ph.

"Administering" or "administration of" a compound or composition drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Alkoxy" refers to an alkyl group covalently bonded to an oxygen atom. In other words, an alkoxy group has the general structure —O-alkyl. $C_1$-$C_6$ alkoxy groups include, for example, methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy.

"Alkenyl" refers to a straight (or linear) or branched chain hydrocarbon group containing at least one carbon-carbon double bond. $C_1$-$C_6$ alkenyl groups include, for example, vinyl, allyl, and butenyl.

"Alkyl" refers to a straight (or linear) or branched chain hydrocarbon group. $C_1$-$C_6$ alkyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl.

"Amino" refers to a monovalent radical —$NR^aR^b$ wherein $R^a$ and $R^b$ are independently hydrogen, alkyl, aryl or heteroaryl. The term "alkylamino" refers to the group —$NR^aR^b$ where $R^a$ is alkyl and $R^b$ is H or alkyl. For dialkylamino groups, the alkyl portions can be the same or different and can also be combined to form a 3- to 8-membered ring with the nitrogen atom to which each is attached. Accordingly, a group represented as —$NR^aR^b$ is meant to include heterocyclyl groups such as piperidinyl, pyrrolidinyl, morpholinyl, azetidinyl and the like.

"Aryl" refers to a cyclic moiety that includes one or more monocyclic or fused ring aromatic systems containing from 6-20 ring carbon atoms. Such moieties include any moiety that has one or more monocyclic or bicyclic fused ring aromatic systems, including but not limited to phenyl and naphthyl.

"($C_m$-$C_n$), $C_m$-$C_n$, or $C_{m-n}$" refer to the number of carbon atoms in a certain group before which one of these symbols are placed. For example, $C_1$-$C_6$ alkyl refers to an alkyl group containing from 1 to 6 carbon atoms.

"Carboxamide or carboxamido" refers to a monovalent radical —CO—$NR^aR^b$, wherein NRaRb is an "amino" group as defined above.

"Carrier" refers to a solid or liquid substance such as a polymer, solvent, suspending agent, absorbing agent, or adsorbing agent for the pre-delivery or capture of a compound of this invention for subsequent delivery. The carrier may be liquid or solid and is selected with the planned manner of administration in mind.

"Comprising" when used to define compounds, compositions and methods means that the recited elements may be present with other materials or steps. "Consisting essentially of," when used to define compounds, compositions or methods, means that the recited elements may not be present with other elements that would materially affect the basic and novel characteristics of the claimed invention. "Consisting of," means only the recited elements. Embodiments defined by each of these transition terms are within the scope of this invention.

"Cycloalkyl" refers to, unless otherwise stated, cyclic versions of "alkyl", "alkenyl" and "alkynyl" in which all ring atoms are carbon. "Cycloalkyl" refers to a mono- or polycyclic group. "Cycloalkyl" may form a bridged ring or a Spiro ring. The cycloalkyl group may have one or more double or triple bond(s). Typical cycloalkyl groups have from 3 to 8 ring atoms. Examples of cycloalkyl include cyclopentyl, cyclohexyl, 1-cyclohexenyl, 3-cyclohexenyl, and cycloheptyl.

"Halogen" or halo" refers to by themselves or as part of another substituent, unless otherwise stated, a fluorine, chlorine, bromine, or iodine atom.

"Heteroaryl" refers to a monocyclic aromatic system having 5 or 6 ring atoms, or a fused ring bicyclic aromatic system having 8-20 atoms, in which the ring atoms are C, O, S, SO, $SO_2$, or N, and at least one of the ring atoms is a heteroatom, i.e., O, S, SO, $SO_2$, or N. Heteroaryl groups include, for example, acridinyl, azocinyl, benzimidazolyl, benzofuranyl, benzothio-furanyl, benzothiophenyl, benzoxazolyl, benzothiazolyl, benzotriazolyl, benzotetrazolyl, benzisoxazolyl, benzisothiazolyl, benzimidazolinyl, carbazolyl, NH-carbazolyl, carbolinyl, chromanyl, chromenyl, cinnolinyl, dithiazinyl, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazole, pyridinyl, pyridyl, pyrimidinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienyl, thienothiazolyl, thienooxazolyl, thienoimidazolyl, thiophenyl, triazinyl and xanthenyl. Unless indicated otherwise, the arrangement of the heteroatoms within the ring may be any arrangement allowed by the bonding characteristics of the constituent ring atoms.

"Heterocyclyl" or heterocyclic refers to a monocyclic or fused ring multicyclic cycloalkyl group at least a portion of which is not aromatic and in which one or more of the carbon atoms in the ring system is replaced by a heteroatom selected from O, S, SO, $SO_2$, P, or N. Examples of heterocyclyl groups include but are not limited to imidazolinyl, morpholinyl, piperidinyl, piperidin-2-onyl, piperazinyl, pyrrolidinyl, pyrrolidine-2-onyl, tetrahydrofuranyl, tetrahydropyranyl, and tetrahydroimidazo [4,5-c] pyridinyl.

"Pharmaceutically acceptable salts" refers to salts of the active compounds which are prepared with relatively nontoxic acids or bases, depending on the particular acidic or basic nature of the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, lithium, magnesium, potassium, sodium, and the like. Salts derived from pharmaceutically-acceptable organic bases include salts of primary, secondary and tertiary amines, including substituted amines, cyclic amines, naturally-occurring amines and the like, such as arginine, betaine, caffeine, choline, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galactunoric acids. Certain specific compounds of the present invention may contain both basic and acidic functionalities that allow the compounds to be converted into either base or acid addition salts.

"Pharmaceutically acceptable excipient, carrier, or diluent" refers to an excipient, carrier, or diluent that is useful in preparing a pharmaceutical composition that is generally safe, non-toxic and neither biologically nor otherwise undesirable, and includes an excipient, carrier, or diluent that is acceptable for human pharmaceutical use as well as veterinary use. A "pharmaceutically acceptable excipient, carrier, or diluent" includes both one and more than one such excipient, carrier, or diluent.

"Reduction" or "inhibition" of a symptom or symptoms (and grammatical equivalents of this phrase) of a pathological condition or disease refers to decreasing the severity or frequency of the symptom(s), or elimination of the symptom(s).

"Subject," used herein interchangeably with "individual" and "patient," refers to a vertebrate, typically a mammal, and usually a human. Mammals include, but are not limited to, mice, rats, rabbits, simians, bovines, ovines, porcines, canines, felines, farm animals, sport animals, pets, equines, and primates.

"Substituted" refers to a group as defined herein in which one or more bonds to a carbon(s) or hydrogen(s) are replaced by a bond to non-hydrogen and non-carbon atom "substituents" include, but are not limited to, a halogen atom; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as nitro, —NH$_2$, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. For cycloalkyl, heterocyclyl, aryl, and heteroaryl groups, "substituents" still further include, substituted and unsubstitued alkyl groups. Other substituents include ethynyl, vinyl, carboxyl and its esters and amides, hydroxymethyl, and methyl. Another "substituent" is the trifluoromethyl or other fluoroalkyl group and other groups that contain these groups. Two substituents on same or adjacent carbon atoms may together with the carbon atoms to which they are bonded form a heterocyclic or cycloalkyl group. Typically, a particular group may have 0 (unsubstituted), 1, 2 or 3 substituents. As will be apparent to the skilled artisan, substitutions with substituents will not result in polymeric moieties of greater than 1000 molecular weight.

"Sulfonamide or sulfonamido" refers to a monovalent radical —SO$_2$—NR$^a$R$^b$, wherein NRaRb is an "amino" group as defined above.

"Therapeutically effective amount" is an amount administered to a patient with a disease mediated by GPR120 that is sufficient to effect beneficial or desired results. A therapeutically effective amount can be administered in one or more administrations, applications, or dosages.

"Treating" or "treatment of" a condition or patient refers to taking steps to obtain beneficial or desired results, including clinical results such as the reduction of symptoms. For purposes of this invention, beneficial or desired clinical results include, but are not limited to, alleviation or amelioration of one or more symptoms of diseases mediated by GPR120; diminishment of extent of such diseases; delay or slowing of such disease progression; amelioration, palliation, or stabilization of such diseases; or other beneficial results.

"Reduction" or "inhibition" of a symptom or symptoms (and grammatical equivalents of this phrase) of a pathological condition or disease refers to decreasing the severity or frequency of the symptom(s), or elimination of the symptom(s).

Accordingly, in a first aspect, the invention provides compounds of Formula I:

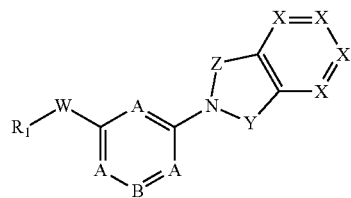

Formula I as well as tautomers, isotopomers and stereoisomers thereof, and prodrugs of any of the foregoing, and pharmaceutically acceptable salts and solvates of all of the foregoing, wherein each A independently is N or CH; B is N or CR$_2$, with the provision that at least one of A or B is N; W is a covalent bond or O; each X independently is CH, CR$_3$ or N wherein R$_3$ is halogen, alkyl, alkoxy, or CN; Y is SO$_2$, CO, CH$_2$, —C(CH$_3$)$_2$—, or —CH(CH$_3$)—; Z is —CH$_2$—, —CH(CH$_3$)—, —C(CH$_3$)$_2$—, —C(CH$_2$CH$_2$)—, CO, —(CO)CH$_2$—, —CH$_2$CH$_2$—, or —CHCH—; R$_1$ is an optionally substituted alkyl group, an optionally substituted 3-7 membered cycloalkyl or heterocyclyl group, or an optionally substituted aryl or heteroaryl group; $R_2$ is H, halogen, CN, $OCH_3$, $OCF_3$, —NH-acyl, an optionally substituted alkyl group, an optionally substituted amido group, an optionally substituted cycloalkyl, or heterocyclyl group, or an optionally substituted aryl or heteroaryl group.

In one preferred embodiment, the central heterocycle is a di- or trisubstituted pyrimidine comprising an optionally substituted 5,6- or 6,6-bicyclic fused ring system, such as without limitation of Formula II:

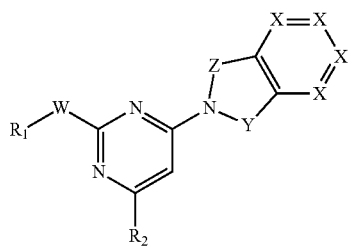

Formula II wherein W is a covalent bond or O; each X independently is CH, $CR_3$ or N wherein $R_3$ is halogen, alkyl, alkoxy, or CN; Y is $SO_2$, CO, $CH_2$, —$C(CH_3)_2$—, or —$CH(CH_3)$—; Z is —$CH_2$—, —$CH(CH_3)$—, —$C(CH_3)_2$—, —$C(CH_2CH_2)$—, CO, —(CO)$CH_2$—, —$CH_2CH_2$—, or —CHCH—; $R_1$ is an optionally substituted alkyl group, an optionally substituted 3-7 membered cycloalkyl or heterocyclyl group, or an optionally substituted aryl or heteroaryl group; $R_2$ is H, halogen, CN, $OCH_3$, $OCF_3$, NHAc, an optionally substituted alkyl group, an optionally substituted amido group, an optionally substituted cycloalkyl, or heterocyclyl group, or an optionally substituted aryl or heteroaryl group.

In a more preferred embodiment of Formula II, W is O and $R_1$ is an optionally substituted cycloalkyl or heterocyclyl group. Examples of specific preferred cycloalkyl and heterocyclyl groups are shown below wherein $R_{11}$ is attached to W. $R_{12}$ and $R_{13}$ are independently H, $CH_3$, $CF_3$, or F.

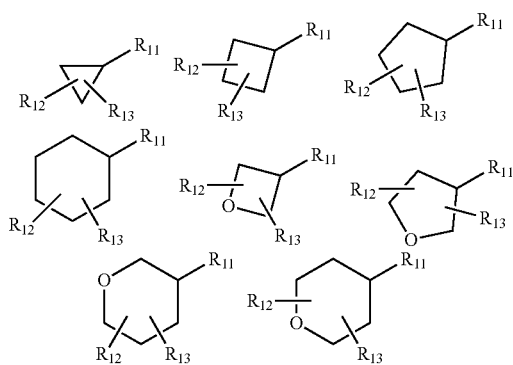

In another more preferred embodiment of Formula II, W is O and $R_1$ is an optionally substituted aryl or heteroaryl group. Examples of specific preferred aryl and heteroaryl groups are shown below wherein $R_{11}$ is attached to W, $R_{15}$ is H, halogen, alkyl, $CF_3$, $OCH_3$, $OCF_3$, or CN, and $R_{16}$ is H, halogen, alkyl, $CF_3$, $OCH_3$, $OCF_3$, CN, $NHCOR_{14}$, or $N(CH_3)COR_{14}$ wherein $R_{14}$ is alkyl, cycloalkyl, aryl or heteroaryl.

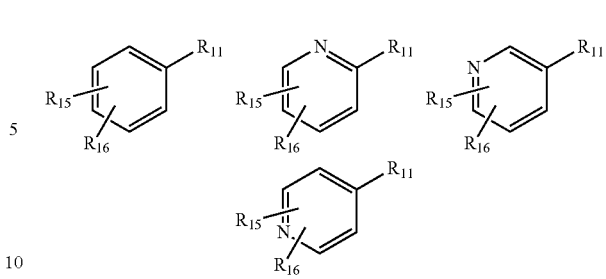

In another more preferred embodiment of Formula II, W is O and $R_1$ is an optionally substituted fused bicyclic aryl or heteroaryl group. Examples of specific preferred fused bicyclic aryl or heteroaryl groups are shown below wherein $R_{11}$ is attached to W, and $R_{15}$ and $R_{17}$ are independently H, halogen, alkyl, $CF_3$, $OCH_3$, $OCF_3$, or CN.

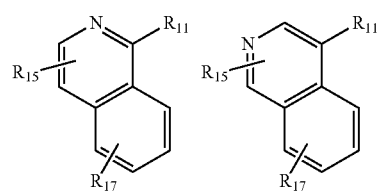

In another more preferred embodiment of Formula II, W is a covalent bond and $R_1$ is an optionally substituted bicyclic amine. Examples of specific preferred bicyclic amines are shown below wherein $R_{11}$ is attached to W, and $R_{15}$ and $R_{17}$ are independently H, halogen, alkyl, $CF_3$, $OCH_3$, $OCF_3$, or CN.

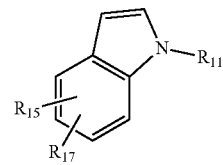

In a second preferred embodiment, the central heterocycle is a di- or trisubstituted pyrimidine comprising an optionally substituted 5,6- or 6,6-bicyclic fused ring system, such as without limitation of Formula III:

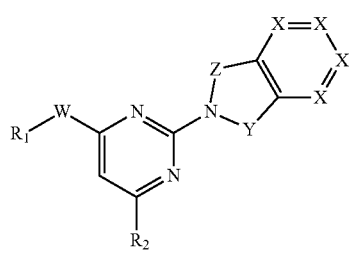

Formula III wherein W is a covalent bond or O; each X independently is CH, $CR_3$ or N wherein $R_3$ is halogen, alkyl, alkoxy, CN; Y is $SO_2$, CO, $CH_2$, —$C(CH_3)_2$—, or —$CH(CH_3)$—; Z is —$CH_2$—, —$CH(CH_3)$—, —$C(CH_3)_2$—, —$C(CH_2CH_2)$—, CO, —(CO)$CH_2$—, —$CH_2CH_2$—, or —CHCH—; $R_1$ is an optionally substituted alkyl group, an optionally substituted 3-7 membered cycloalkyl or heterocyclyl group, or an optionally substituted aryl or heteroaryl group; $R_2$ is H, halogen, CN, $OCH_3$, $OCF_3$, NHAc, an optionally substituted alkyl group, an optionally substituted amido group, an optionally substituted cycloalkyl, or heterocyclyl group, or an optionally substituted aryl or heteroaryl group.

In a more preferred embodiment of Formula III, W is O and $R_1$ is an optionally substituted cycloalkyl or heterocyclyl group. Examples of specific preferred cycloalkyl and heterocyclyl groups are shown below wherein $R_{11}$ is attached to W. $R_{12}$ and $R_{13}$ are independently H, $CH_3$, $CF_3$, or F.

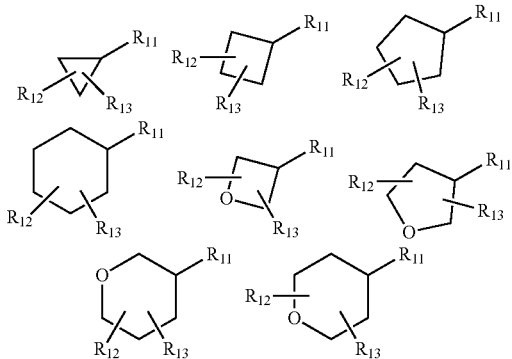

In another more preferred embodiment of Formula III, W is O and $R_1$ is an optionally substituted aryl or heteroaryl group. Examples of specific preferred aryl and heteroaryl groups are shown below wherein $R_{11}$ is attached to W, $R_{15}$ is H, halogen, alkyl, $CF_3$, $OCH_3$, $OCF_3$, or CN, and $R_{16}$ is H, halogen, alkyl, $CF_3$, $OCH_3$, $OCF_3$, CN, $NHCOR_{14}$, or $N(CH_3)COR_{14}$ wherein $R_{14}$ is alkyl, cycloalkyl, aryl or heteroaryl.

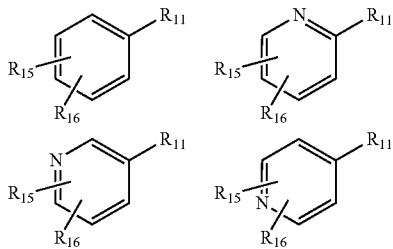

In another more preferred embodiment of Formula III, W is O and $R_1$ is an optionally substituted fused bicyclic aryl or heteroaryl group. Examples of specific preferred fused bicyclic aryl or heteroaryl groups are shown below wherein $R_{11}$ is attached to W, and $R_{15}$ and $R_{17}$ are independently H, halogen, alkyl, $CF_3$, $OCH_3$, $OCF_3$, or CN.

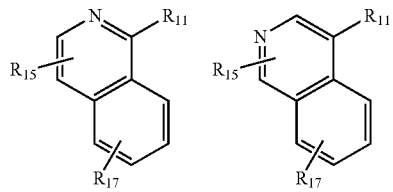

In another more preferred embodiment of Formula III, W is a covalent bond and $R_1$ is an optionally substituted bicyclic amine. Examples of specific preferred bicyclic amines are shown below wherein $R_{11}$ is attached to W, and $R_{15}$ and $R_{17}$ are independently H, halogen, alkyl, $CF_3$, $OCH_3$, $OCF_3$, or CN.

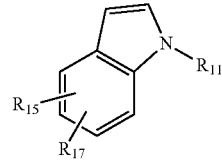

In a third preferred embodiment, the central heterocycle is a di- or trisubstituted pyridine comprising an optionally substituted 5,6- or 6,6-bicyclic fused ring system, such as without limitation of Formula IV:

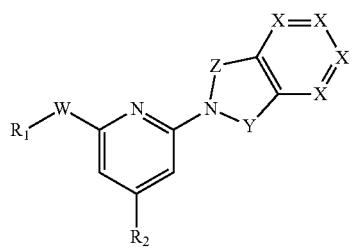

Formula IV
wherein W is a covalent bond or O; each X independently is CH, $CR_3$ or N wherein $R_3$ is halogen, alkyl, alkoxy, CN; Y is $SO_2$, CO, $CH_2$, $—C(CH_3)_2—$, or $—CH(CH_3)—$; Z is $—CH_2—$, $—CH(CH_3)—$, $—C(CH_3)_2—$, $—C(CH_2CH_2)—$, CO, $—(CO)CH_2—$, $—CH_2CH_2—$, or $—CHCH—$; $R_1$ is an optionally substituted alkyl group, an optionally substituted 3-7 membered cycloalkyl or heterocyclyl group, or an optionally substituted aryl or heteroaryl group; $R_2$ is H, halogen, CN, $OCH_3$, $OCF_3$, NHAc, an optionally substituted alkyl group, an optionally substituted amido group, an optionally substituted cycloalkyl, or heterocyclyl group, or an optionally substituted aryl or heteroaryl group.

In a more preferred embodiment of Formula IV, W is O and $R_1$ is an optionally substituted cycloalkyl or heterocyclyl group. Examples of specific preferred cycloalkyl and heterocyclyl groups are shown below wherein $R_{11}$ is attached to W. $R_{12}$ and $R_{13}$ are independently H, $CH_3$, $CF_3$, or F.

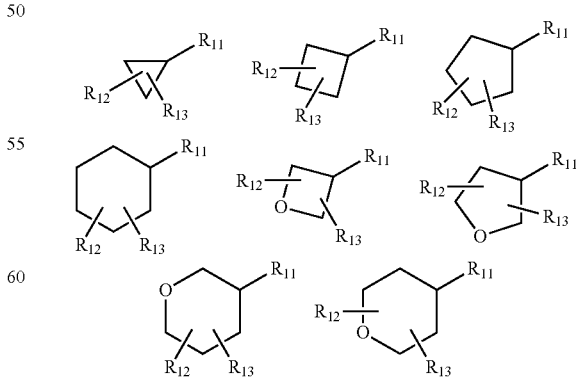

In another more preferred embodiment of Formula IV, W is O and $R_1$ is an optionally substituted aryl or heteroaryl group. Examples of specific preferred aryl and heteroaryl groups are shown below wherein $R_{11}$ is attached to W, $R_{15}$ is H, halogen, alkyl, $CF_3$, $OCH_3$, $OCF_3$, or CN, and $R_{16}$ is H, halogen, alkyl, $CF_3$, $OCH_3$, $OCF_3$, CN, $NHCOR_{14}$, $N(CH_3)COR_{14}$ wherein $R_{14}$ is alkyl, cycloalkyl, aryl or heteroaryl.

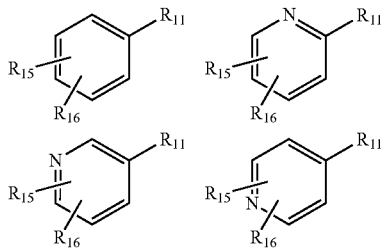

In another more preferred embodiment of Formula IV, W is O and $R_1$ is an optionally substituted fused bicyclic aryl or heteroaryl group. Examples of specific preferred fused bicyclic aryl or heteroaryl groups are shown below wherein $R_{11}$ is attached to W, and $R_{15}$ and $R_{17}$ are independently H, halogen, alkyl, $CF_3$, $OCH_3$, $OCF_3$, or CN.

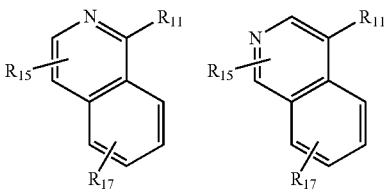

In another more specific preferred embodiment of Formula IV, W is a covalent bond and $R_1$ is an optionally substituted bicyclic amine. Examples of specific preferred bicyclic amines are shown below wherein $R_{11}$ is attached to W, and $R_{15}$ and $R_{17}$ are independently H, halogen, alkyl, $CF_3$, $OCH_3$, $OCF_3$, or CN.

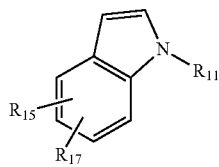

In a fourth preferred embodiment, the central heterocycle is a disubstituted pyrazine comprising an optionally substituted 5,6- or 6,6-bicyclic fused ring system, such as without limitation of Formula V:

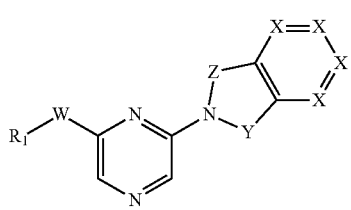

Formula V wherein W is a covalent bond or O; each X independently is CH, $CR_3$ or N wherein $R_3$ is halogen, alkyl, alkoxy, or CN; Y is $SO_2$, CO, $CH_2$, —$C(CH_3)_2$—, or —$CH(CH_3)$—; Z is —$CH_2$—, —$CH(CH_3)$—, —$C(CH_3)_2$—, —$C(CH_2CH_2)$—, CO, —(CO)$CH_2$—, or —$CH_2CH_2$—, —CHCH—; $R_1$ is an optionally substituted alkyl group, an optionally substituted 3-7 membered cycloalkyl or heterocyclyl group, or an optionally substituted aryl or heteroaryl group.

In a more preferred embodiment of Formula V, W is O and $R_1$ is an optionally substituted cycloalkyl or heterocyclyl group. Examples of specific preferred cycloalkyl and heterocyclyl groups are shown below wherein $R_{11}$ is attached to W. $R_{12}$ and $R_{13}$ are independently H, $CH_3$, $CF_3$, or F.

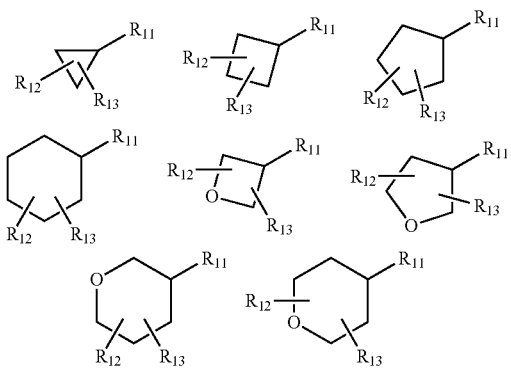

In another more preferred embodiment of Formula V, W is O and $R_1$ is an optionally substituted aryl or heteroaryl group. Examples of specific preferred aryl and heteroaryl groups are shown below wherein $R_{11}$ is attached to W, $R_{15}$ is H, halogen, alkyl, $CF_3$, $OCH_3$, $OCF_3$, or CN, and $R_{16}$ is H, halogen, alkyl, $CF_3$, $OCH_3$, $OCF_3$, CN, $NHCOR_{14}$, or $N(CH_3)COR_{14}$ wherein $R_{14}$ is alkyl, cycloalkyl, aryl or heteroaryl.

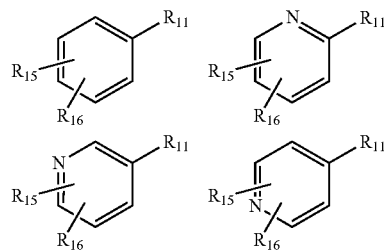

In another more preferred embodiment of Formula V, W is O and $R_1$ is an optionally substituted fused bicyclic aryl or heteroaryl group. Examples of specific preferred fused bicyclic aryl or heteroaryl groups are shown below wherein $R_{11}$ is attached to W, and $R_{15}$ and $R_{17}$ are independently H, halogen, alkyl, $CF_3$, $OCH_3$, $OCF_3$, or CN.

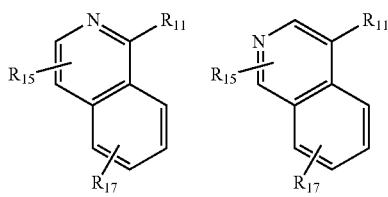

In another more preferred embodiment of Formula V, W is a covalent bond and $R_1$ is an optionally substituted bicyclic amine. Examples of specific preferred bicyclic amines are shown below wherein $R_{11}$ is attached to W, and $R_{15}$ and $R_{17}$ are independently H, halogen, alkyl, $CF_3$, $OCH_3$, $OCF_3$, or CN.

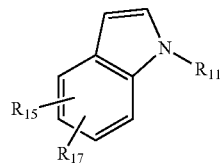

In a fifth preferred embodiment, the central heterocycle is a di- or trisubstituted triazole comprising an optionally substituted 5,6- or 6,6-bicyclic fused ring system, such as without limitation of Formula VI:

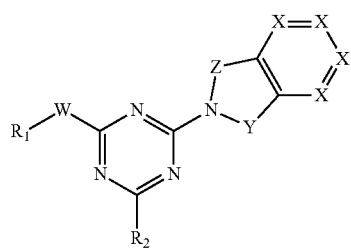

Formula VI wherein W is a covalent bond or O; each X independently is CH, $CR_3$ or N wherein $R_3$ is halogen, alkyl, alkoxy, or CN; Y is $SO_2$, CO, $CH_2$, —$C(CH_3)_2$—, or —$CH(CH_3)$—; Z is —$CH_2$—, —$CH(CH_3)$—, —$C(CH_3)_2$—, —$C(CH_2CH_2)$—, CO, —(CO)$CH_2$—, —$CH_2CH_2$—, or —CHCH—; $R_1$ is an optionally substituted alkyl group, an optionally substituted 3-7 membered cycloalkyl or heterocyclyl group, or an optionally substituted aryl or heteroaryl group; $R_2$ is H, halogen, CN, $OCH_3$, $OCF_3$, NHAc, an optionally substituted alkyl group, an optionally substituted amido group, an optionally substituted cycloalkyl, or heterocyclyl group, or an optionally substituted aryl or heteroaryl group.

In a more preferred embodiment of Formula VI, W is O and $R_1$ is an optionally substituted cycloalkyl or heterocyclyl group. Examples of specific preferred cycloalkyl and heterocyclyl groups are shown below wherein $R_{11}$ is attached to W. $R_{12}$ and $R_{13}$ are independently H, $CH_3$, $CF_3$, or F.

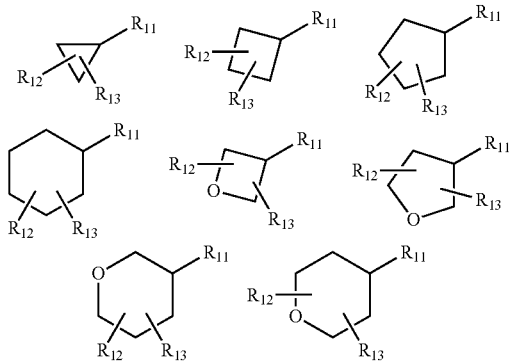

In another more preferred embodiment of Formula VI, W is O and $R_1$ is an optionally substituted aryl or heteroaryl group. Examples of specific preferred aryl and heteroaryl groups are shown below wherein $R_{11}$ is attached to W, $R_{15}$ is H, halogen, alkyl, $CF_3$, $OCH_3$, $OCF_3$, or CN, and $R_{16}$ is H, halogen, alkyl, $CF_3$, $OCH_3$, $OCF_3$, CN, $NHCOR_{14}$, or $N(CH_3)COR_{14}$ wherein $R_{14}$ is alkyl, cycloalkyl, aryl or heteroaryl.

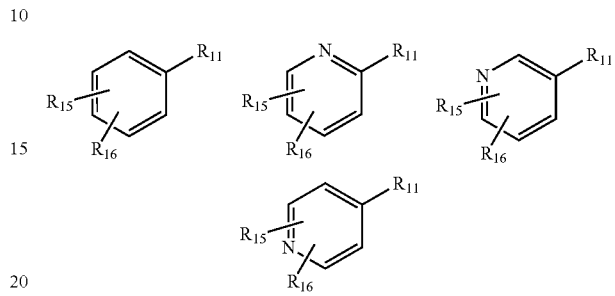

In another more preferred embodiment of Formula VI, W is O and $R_1$ is an optionally substituted fused bicyclic aryl or heteroaryl group. Examples of specific preferred fused bicyclic aryl or heteroaryl groups are shown below wherein $R_{11}$ is attached to W, and $R_{15}$ and $R_{17}$ are independently H, halogen, alkyl, $CF_3$, $OCH_3$, $OCF_3$, or CN.

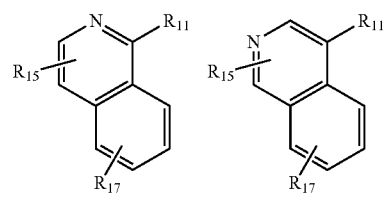

In another more preferred embodiment of Formula VI, W is a covalent bond and $R_1$ is an optionally substituted bicyclic amine. Examples of specific preferred bicyclic amines are shown below wherein $R_{11}$ is attached to W, and $R_{15}$ and $R_{17}$ are independently H, halogen, alkyl, $CF_3$, $OCH_3$, $OCF_3$, or CN.

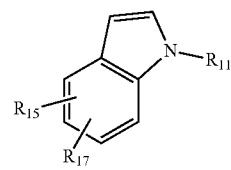

In another aspect, a compound provided herein is selected from:

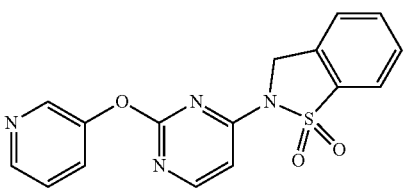

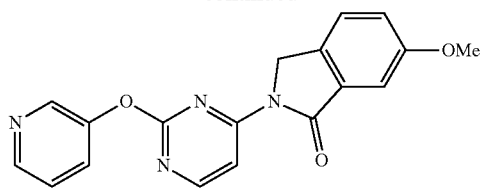
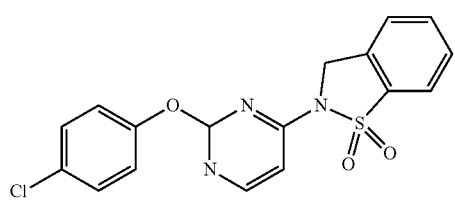
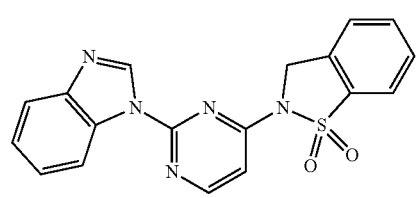
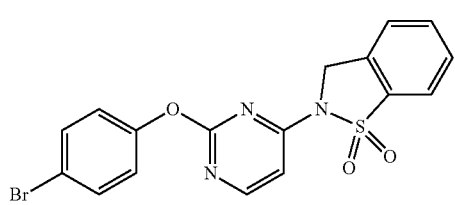
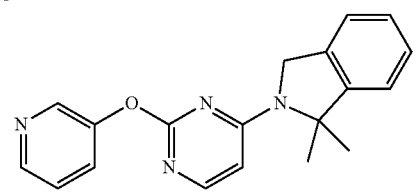
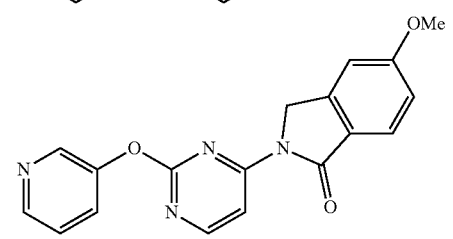
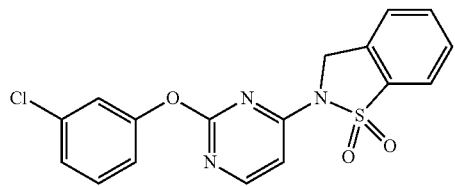
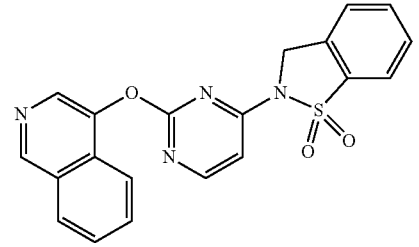
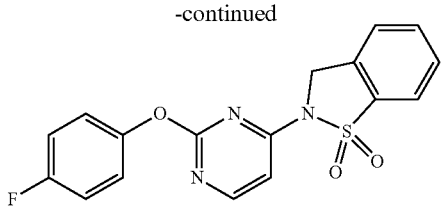
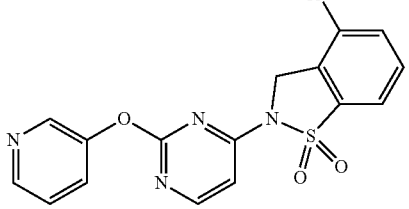
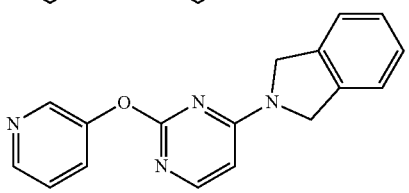
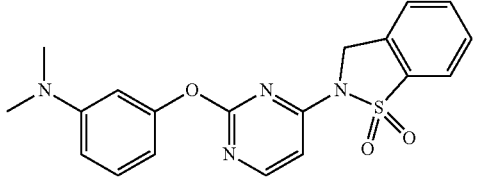
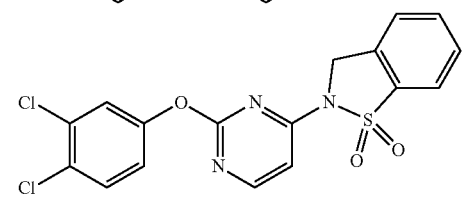
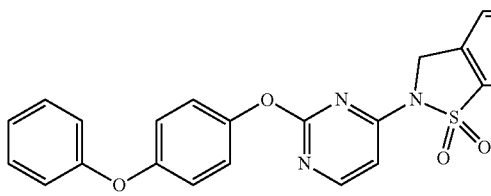
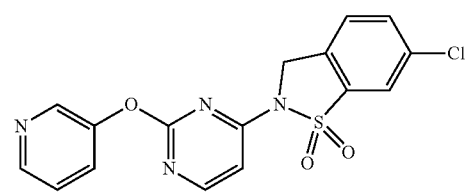
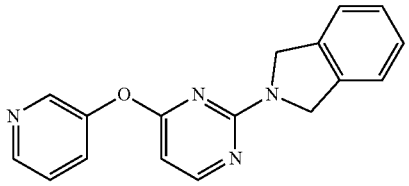
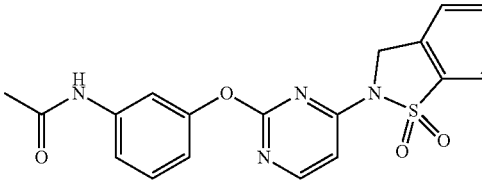

-continued
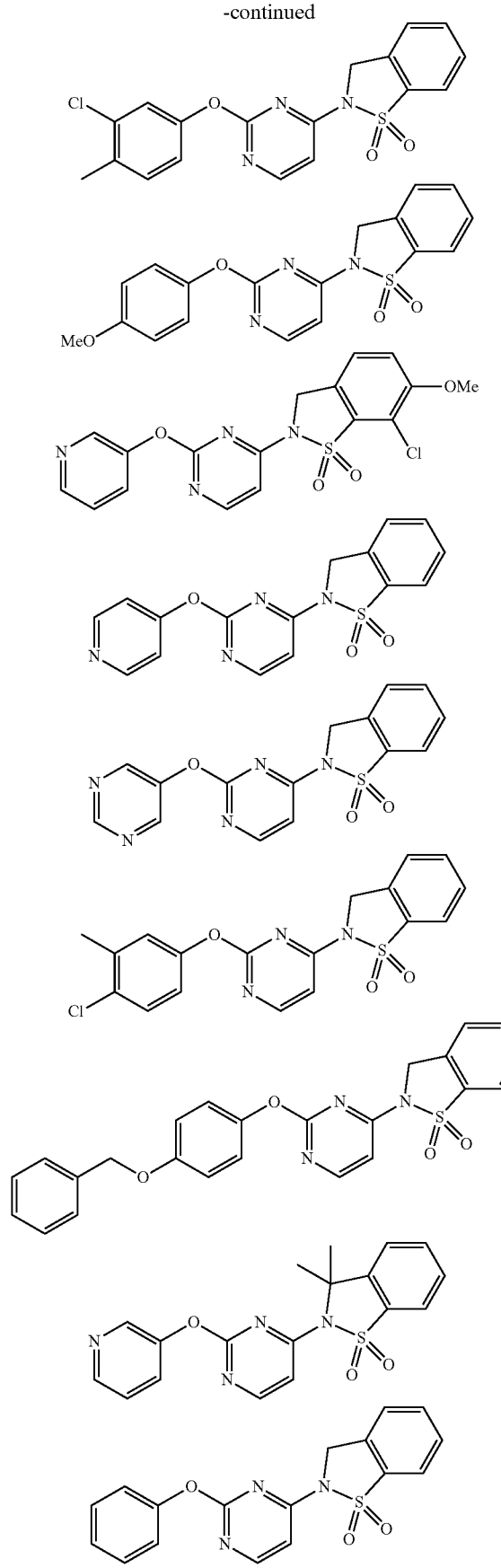
-continued
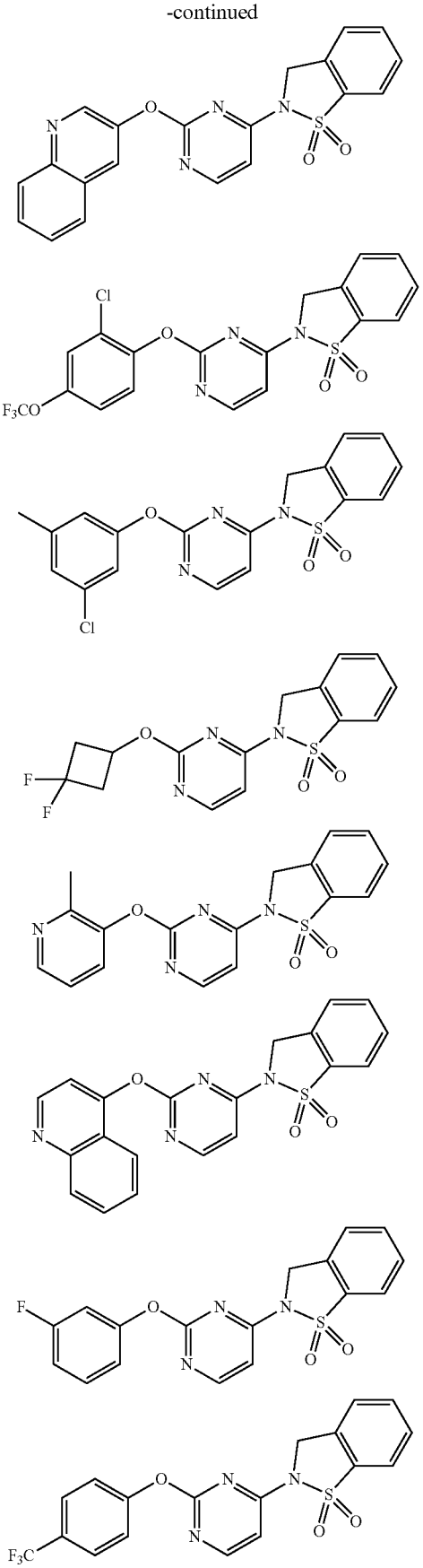

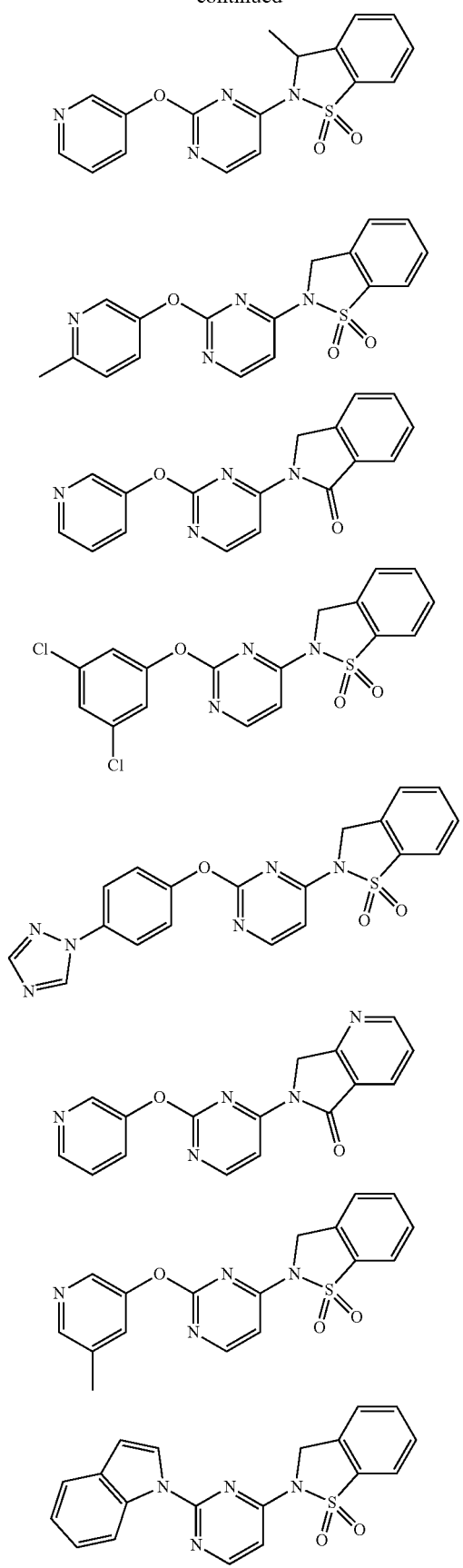
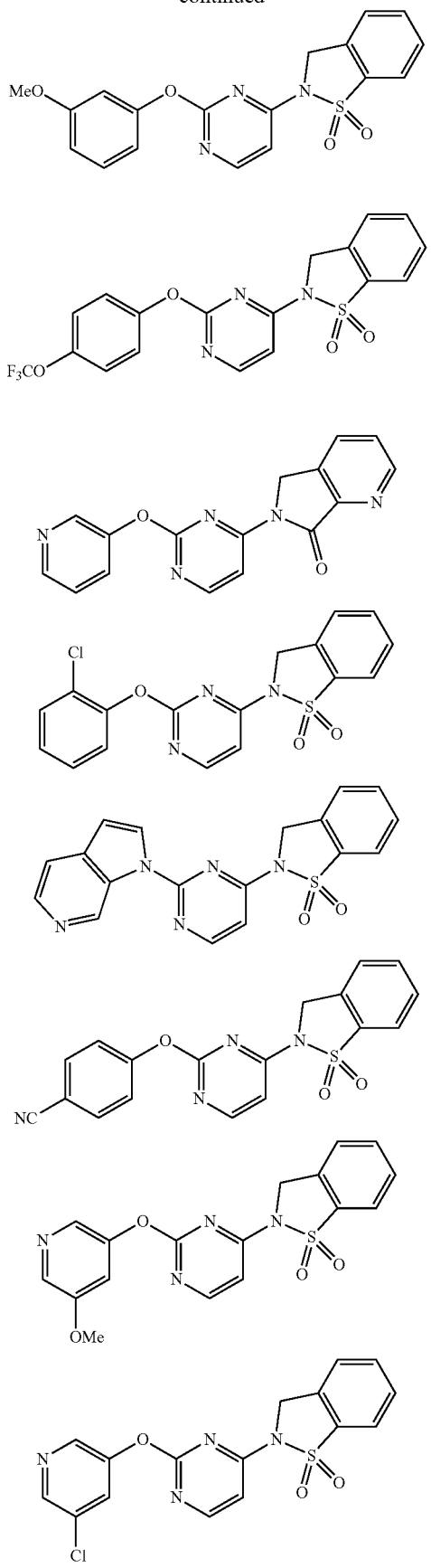

-continued
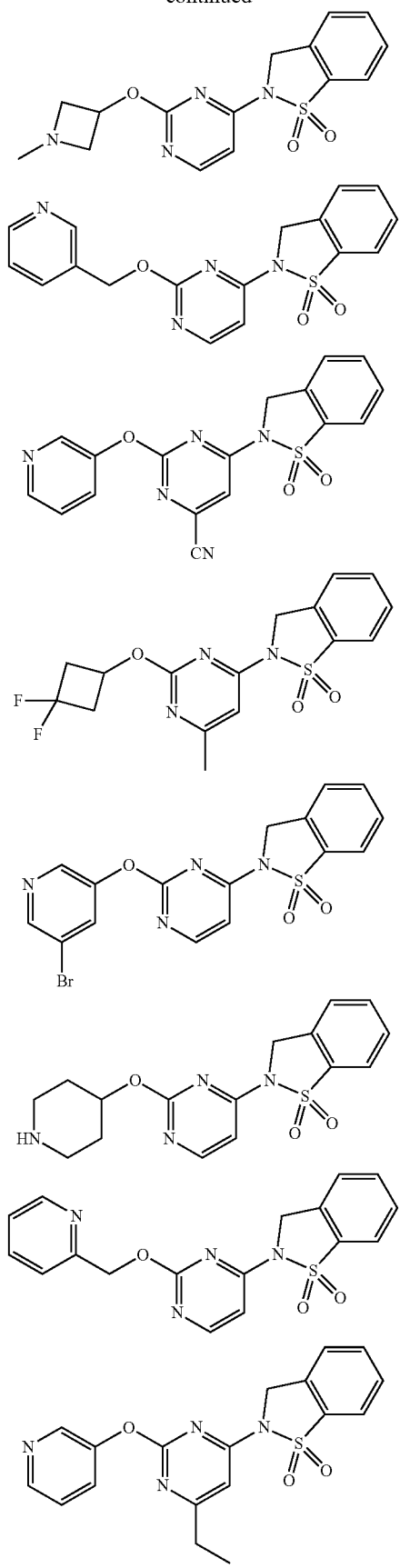
-continued
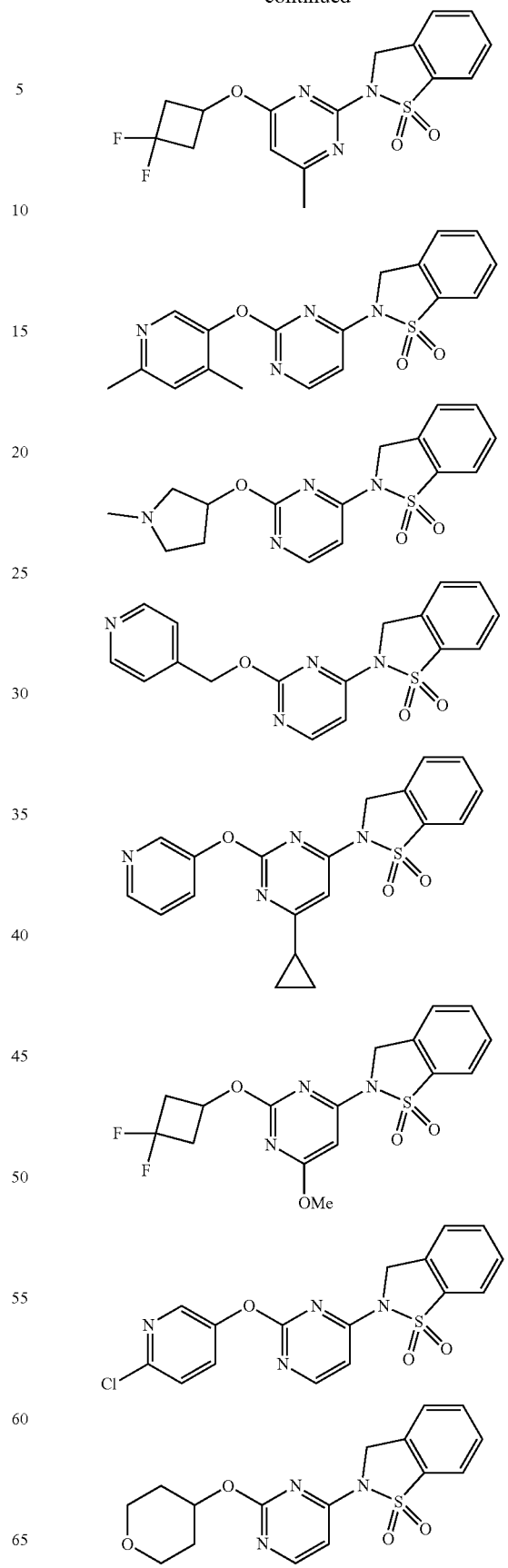

-continued
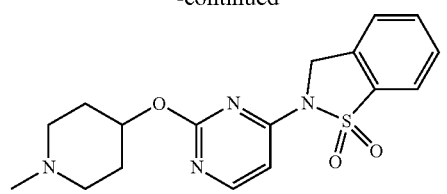
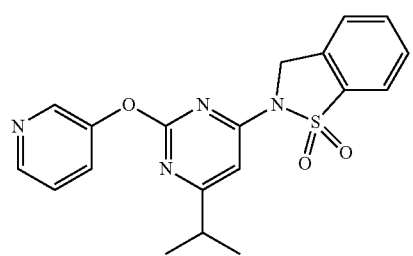
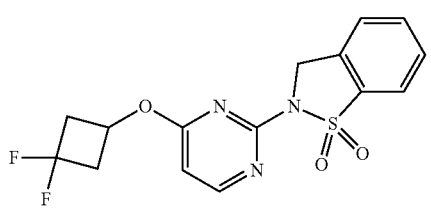
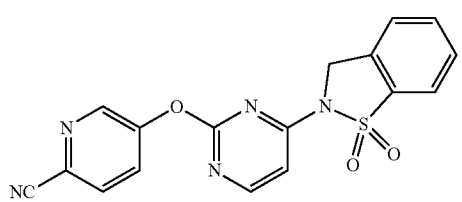
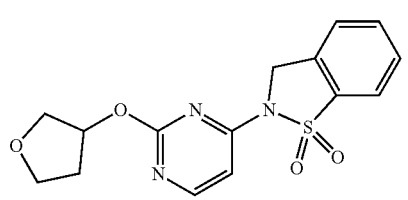
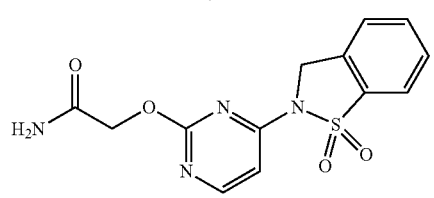
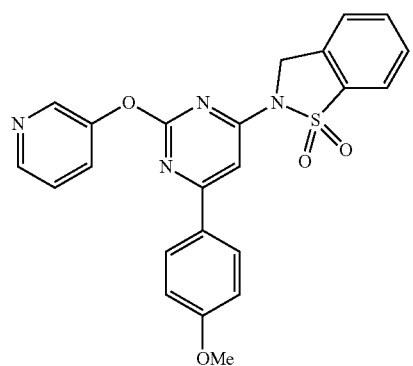
-continued
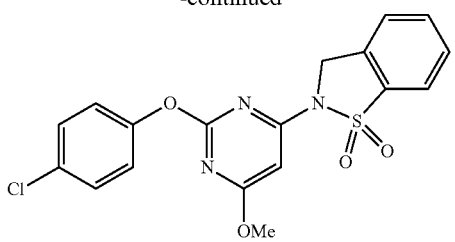
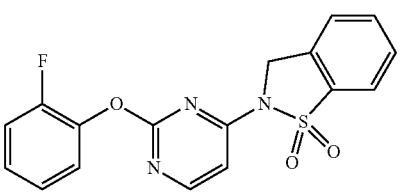
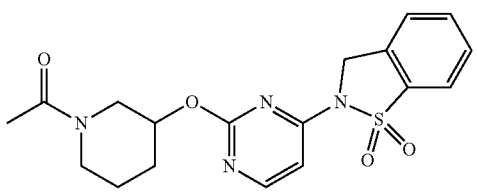
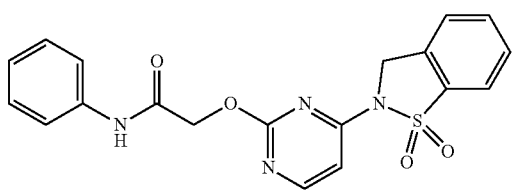
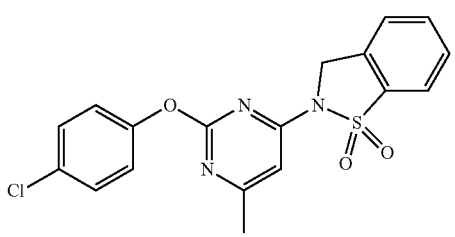
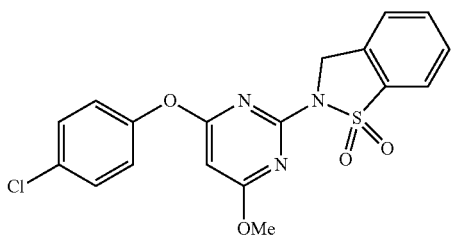
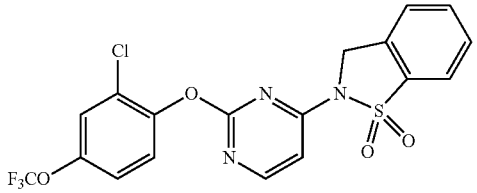
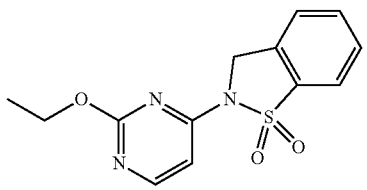

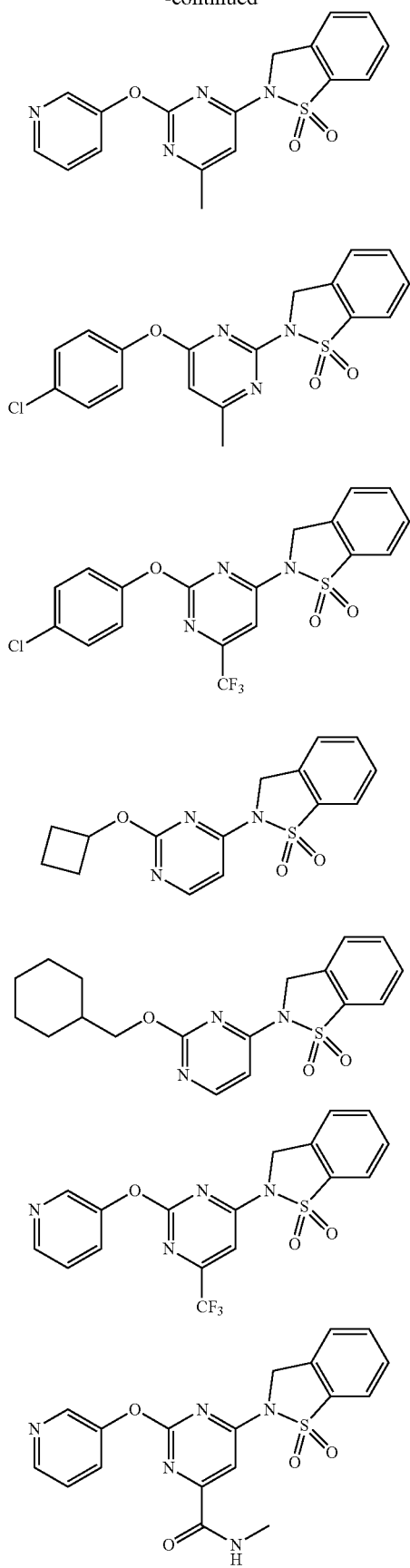
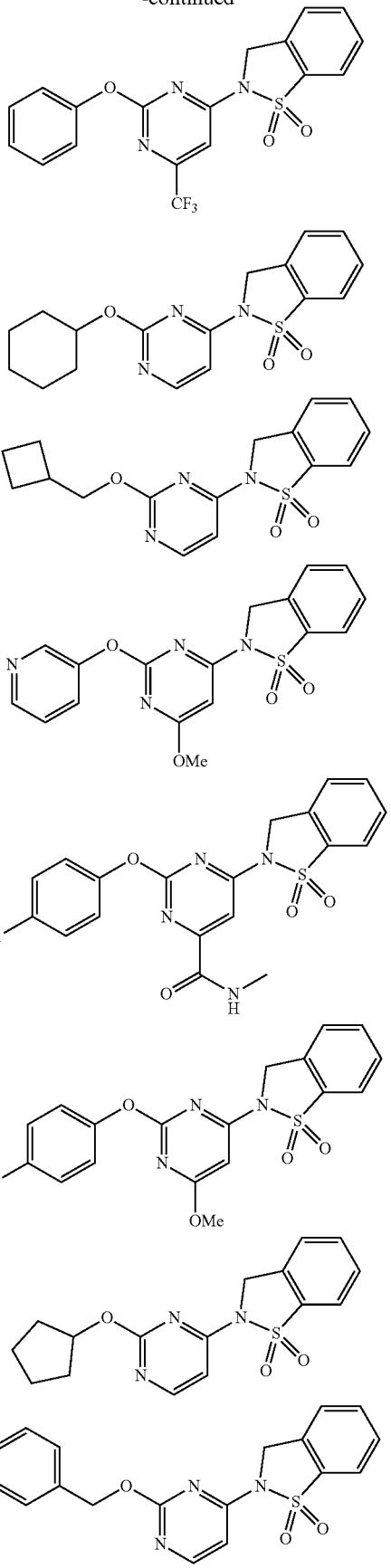

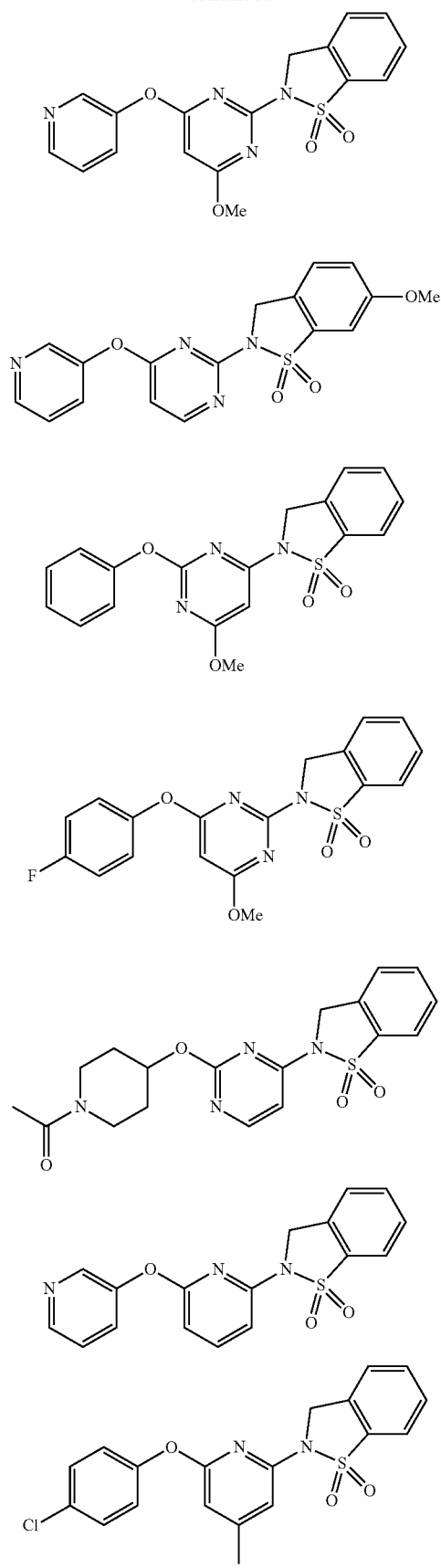
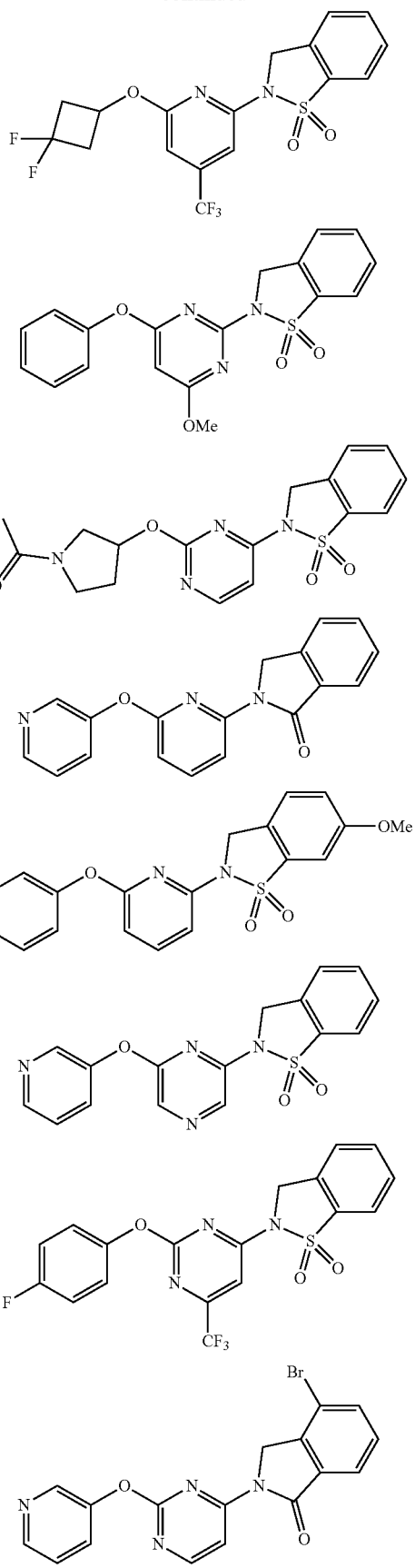

-continued
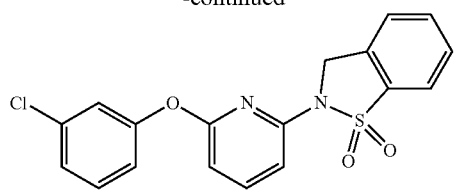
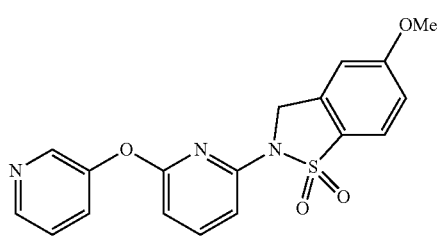
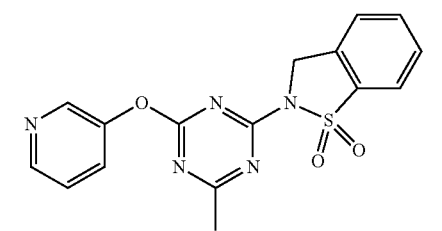
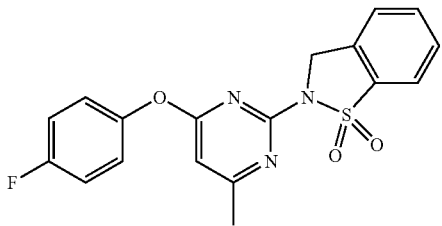
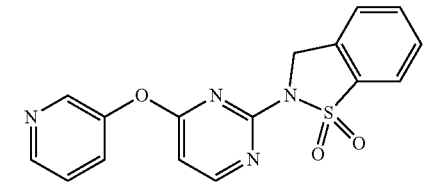
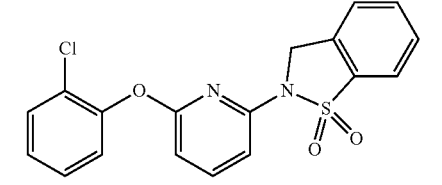
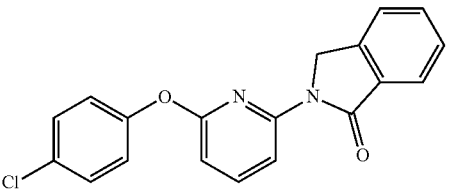
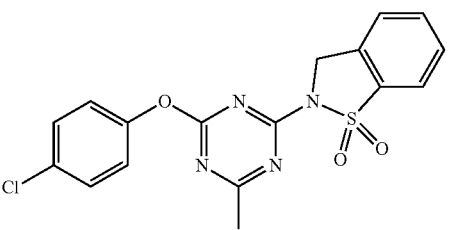
-continued
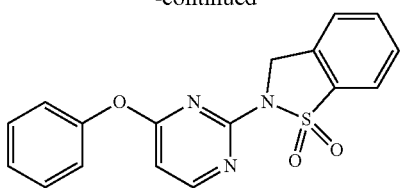
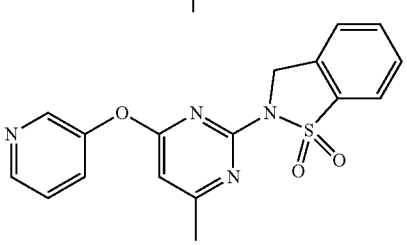
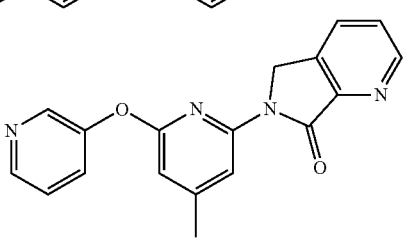
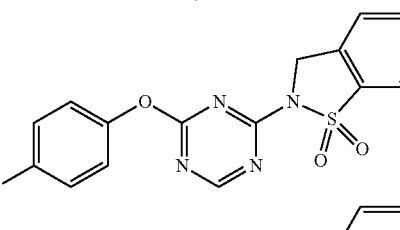
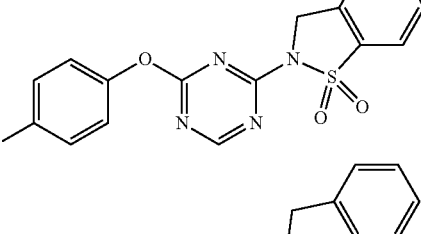
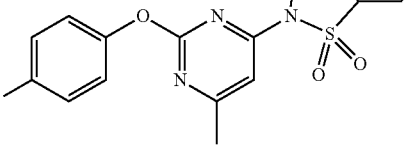
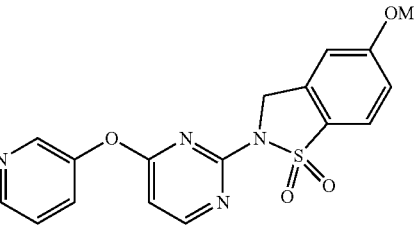

33
-continued
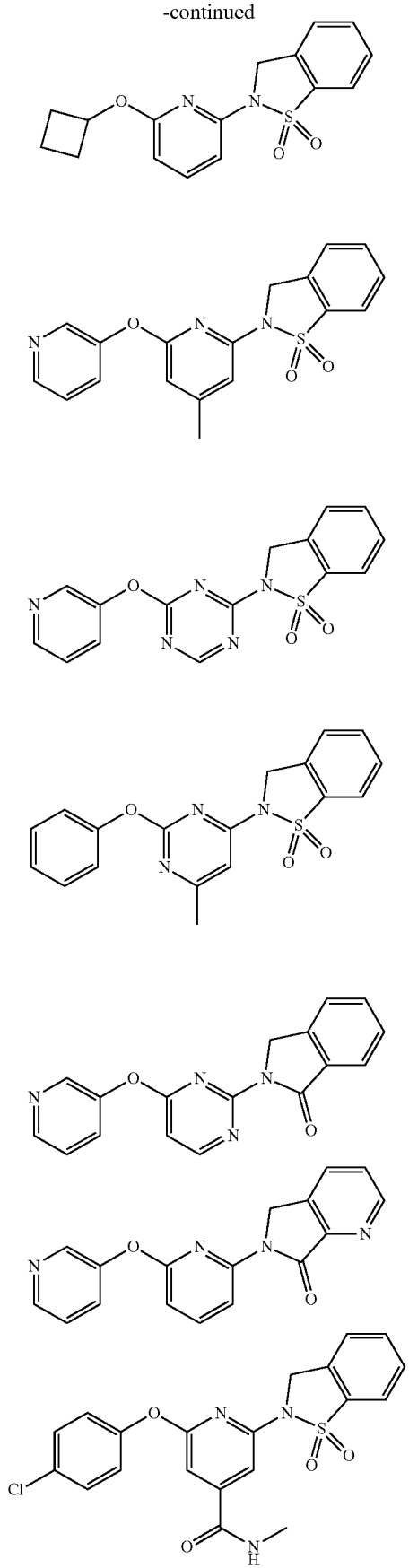
34
-continued
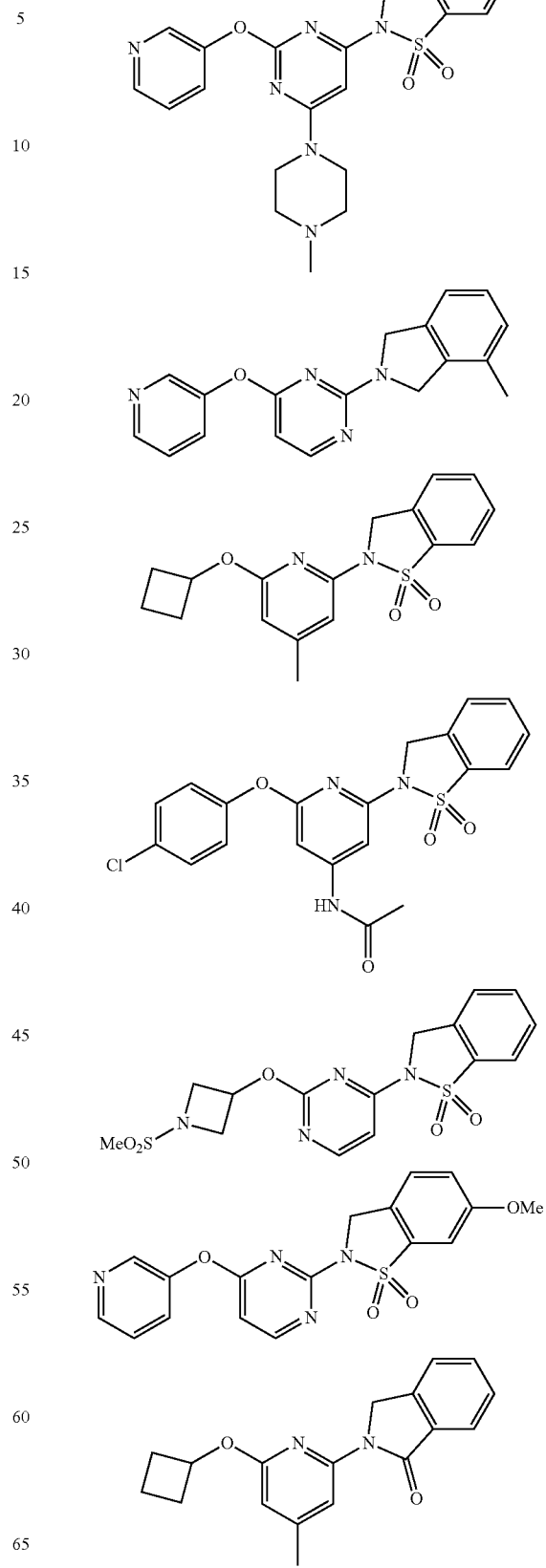

-continued

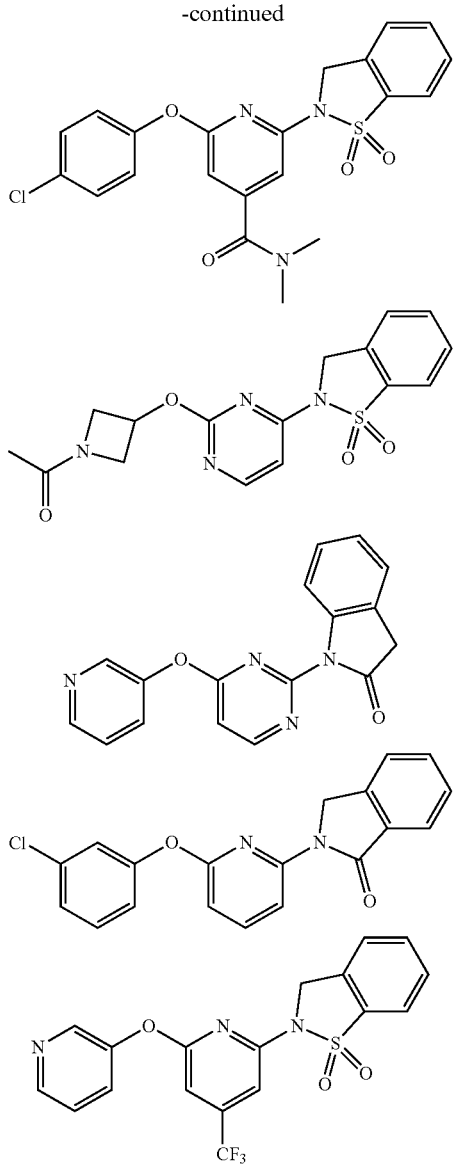

Certain compounds of the present invention are synthesized as schematically described herein below. Other compounds of the present invention can be synthesized by adapting these and other methods exemplified in the Examples section below or methods known to one of skill in the art upon appropriate substitution of starting materials, other reagents, and/or process conditions (i.e., reaction temperatures, times, mole ratios of reactants, solvents, pressures, and the like).

For compounds of the invention that contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of the compounds provided and utilized herein unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In another aspect, the present invention provides compositions comprising a compound of the present invention, and at least one pharmaceutically acceptable excipient, i.e., pharmaceutical formulations. In general, the compounds of the present invention can be formulated for administration to a patient by any of the accepted modes of administration. Thus, the invention provides solid and liquid formulations of the compounds of the invention. Various formulations and drug delivery systems are available in the art. See, e.g., Gennaro, A. R., ed. (1995) *Remington's Pharmaceutical Sciences,* 18th ed., Mack Publishing Co.

Typically, compounds of the present invention will be administered as pharmaceutical compositions by one of the following routes: oral, systemic (e.g., transdermal, intranasal or by suppository), or parenteral (e.g., intramuscular, intravenous or subcutaneous) administration. Compositions can take the form of tablets, pills, capsules, semisolids, powders, sustained release formulations, solutions, suspensions, elixirs, aerosols, or any other appropriate compositions.

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-)encapsulating, entrapping, or lyophilization processes. As noted above, the compositions of the present invention can include one or more physiologically acceptable inactive ingredients that facilitate processing of active molecules into preparations for pharmaceutical use.

Pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. In some embodiments, the compounds of the present invention are formulated accordingly.

The compositions are comprised of in general, a compound of the present invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of the present invention based on the total formulation, with the balance being one or more suitable pharmaceutical excipients. Generally, the compound is present at a level of about 1-80 wt %.

In another aspect, the invention provides a method of producing a therapeutic effect of GPR120 by contacting a therapeutically effective amount of a compound or a composition of the present invention with the GPR120 in need thereof. In one embodiment, the therapeutic effect is produced in a cell. In another embodiment, the contacting is performed in vitro or in vivo.

In another aspect, provided herein is a method of treating Type 2 diabetes in a subject in need thereof comprising administering to the subject a therapeutically effective amount of a compound or a composition of the present invention. In one embodiment, the subject is a human.

All technical and patent publications cited herein are incorporated herein by reference in their entirety.

The invention having been described in summary and in detail is illustrated and not limited by the examples below. Examples 1-146 illustrate specific compounds of the invention and methods for their synthesis. Examples 147 and 148 illustrate methods whereby the ability of compounds of the invention to activate the GPR120 receptor can be measured in biological assays.

SYNTHESIS EXAMPLES

Example 1

Synthesis of Compound 1

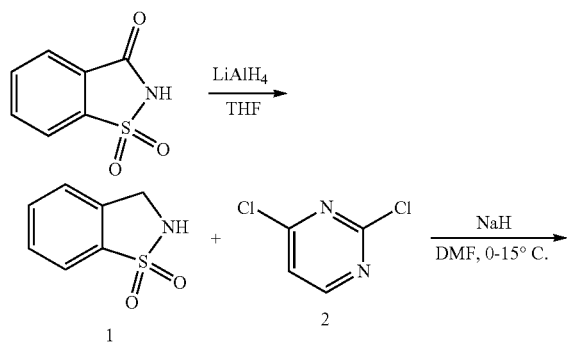

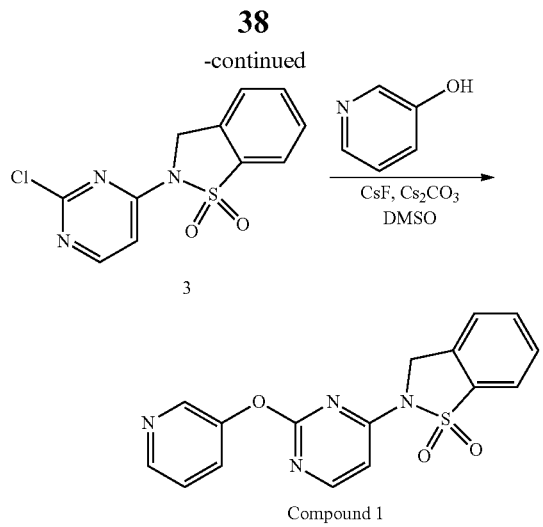

Compound 1

Step 1.

Saccharin (10.0 g, 54.6 mmol) was slowly added to solution of LiAlH$_4$ (2.24 g, 59.0 mmol) in 300 mL of THF at 0° C. The reaction mixture was stirred for 3 h at 15° C. under an inert atmosphere. Upon completion, EtOAc (100 mL) was slowly added followed by addition of 10% H$_2$SO$_4$ (100 mL). The organic layer was separated and washed with 100 mL of 5% sodium carbonate solution, dried over anhydrous sodium sulfate, filtered, and concentrated to give 1 (4.4 g, 97%).

Step 2.

To a solution of 1 (97.0 mg, 0.57 mmol) in DMF (4 mL) was added NaH (13.9 mg, 0.58 mmol) at 0° C. The mixture was stirred at 0° C. for 30 minutes. Dichloropyrimidine 2 (100 mg, 0.48 mmol, 1.0 eq) was added, the solution was allowed to warm to 15° C. and stirred for 15 hours. The resulting mixture was poured into ice water (w/w=1/1, 20 mL) and stirred for 10 minutes. The aqueous phase was extracted with EtOAc (30 mL) and the combined organic phase was washed with brine (20 mL), dried with anhydrous Na$_2$SO$_4$, filtered, and concentrated in vacuo to afford 3 (120 mg, 72%).

Step 3.

A solution of 3 (200 mg, 0.71 mmol), pyridin-3-ol (81 g, 852 mmol), CsF (215 mg, 1.42 mmol) and Cs$_2$CO$_3$ (462 mg, 1.42 mmol) in DMSO (3 mL) was degassed and then heated to 80° C. for 16 hours under an inert atmosphere. Upon consumption of starting material the reaction mixture was poured into water (50 mL). The mixture was extracted with EtOAc (60 mL). The organic phase was washed with brine (30 mL), dried over anhydrous sodium sulfate, and concentrated in vacuo. The resulting material was purified by preparative HPLC to afford 70 mg (29%) of Compound 1. $^1$H NMR (DMSO-d$_6$, 400 MHz) δ 8.56 (d, 1H), 8.52-8.46 (m, 2H), 8.06 (d, 1H), 7.88-7.82 (m, 1H), 7.81-7.68 (m, 3H), 7.51 (dd, 1H), 7.09 (d, 1H), 5.18 (s, 2H); LCMS (ESI+): m/z 341 (M+H).

Example 2

Synthesis of Compound 2

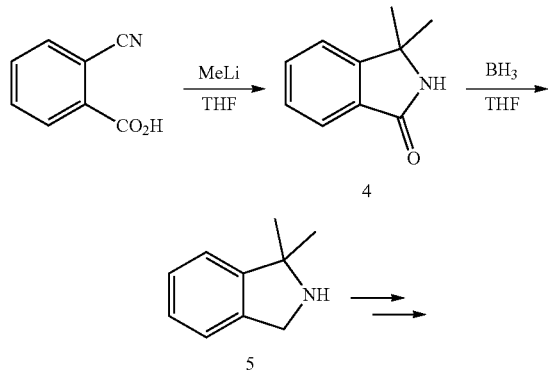

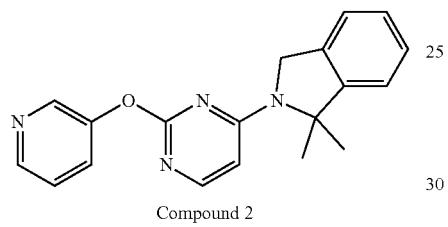

Compound 2

Step 1.

To a solution 2-cyanobenzoic acid (1.50 g, 10.2 mmol) in THF (15 mL) was added MeLi (1M, 204 mL) drop wise at −78° C. The resulting mixture was stirred for 2 h at −78° C., warmed to 30° C., and stirred for an additional 18 h. Upon completion, water (300 mL) was added and the mixture was extracted with EtOAc (300 mL). The organic phase was washed with brine (100 mL), dried with $Na_2SO_4$, and concentrated under reduced pressure. Purification by silica gel column chromatography (petroleum ether:EtOAc=1:1) resulted in 4 (400 mg, 22%).

Step. 2

$BH_3$·THF (1M, 5.7 mL) was added to a solution of 3,3-dimethylphthalimidine (230 mg, 1.43 mmol) in THF (6 mL) drop wise under inert atmosphere and the resulting mixture was stirred at 80° C. for 16 h. Upon completion, MeOH (4 mL) was added and the reaction mixture was allowed to stir for 5 h. Concentration under reduced pressure and purification by prep-TLC (silica-gel, petroleum ether: EtOAc=3:1) resulted in 5.

From 5, Compound 2 was synthesized in a manner similar to Compound 1. $^1$H NMR (DMSO-$d_6$, 400 MHz) δ 8.79 (s, 1H), 8.67-8.66 (d, 1H), 8.27-8.25 (d, 1H), 8.08-8.06 (d, 1H), 7.77-7.74 (m, 1H), 7.30-7.28 (m, 1H), 6.60-6.58 (d, 1H), 4.85 (s, 2H), 1.34 (s, 6H); LCMS (ESI): m/z 319.1 (M+H).

Example 3

Synthesis of Compound 3

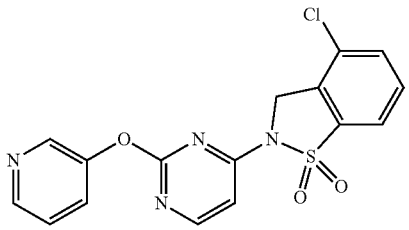 [SMILES: O=S1(=O)c2cccc(Cl)c2CN1c1ccnc(Oc2cccnc2)n1]

Compound 3 was synthesized in a manner similar to Compound 1. LCMS (ESI): m/z 375.0 (M+H).

Example 4

Synthesis of Compound 4

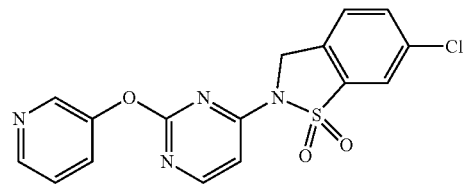 [SMILES: O=S1(=O)c2cc(Cl)ccc2CN1c1ccnc(Oc2cccnc2)n1]

Compound 4 was synthesized in a manner similar to Compound 1. LCMS (ESI): m/z 375.1 (M+H).

Example 5

Synthesis of Compound 5

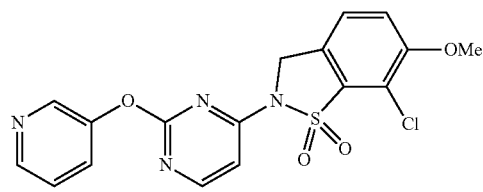 [SMILES: COc1ccc2c(c1Cl)S(=O)(=O)N(c1ccnc(Oc3cccnc3)n1)C2]

Compound 5 was synthesized in a manner similar to Compound 1. $^1$H NMR (DMSO-$d_6$, 400 MHz) δ 8.55-8.50 (m, 4H), 7.79-7.77 (d, 1H), 7.67 (s, 2H), 7.53-7.51 (d, 1H), 7.08-7.07 (d, 1H), 5.7 (s, 2H), 3.98 (s, 3H); LCMS (ESI): m/z 405.0 (M+H).

Example 6

Synthesis of Compound 6

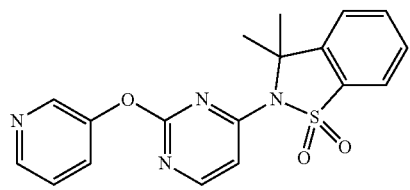 [SMILES: CC1(C)c2ccccc2S(=O)(=O)N1c1ccnc(Oc2cccnc2)n1]

Compound 6 was synthesized in a manner similar to Compound 1. $^1$H NMR (DMSO-d$_6$, 400 MHz) δ 8.87 (s, 1H), 8.70-8.69 (d, 1H), 8.59-8.57 (d, 1H), 8.18-8.16 (d, 1H), 8.05-8.03 (d, 1H), 7.88-7.82 (m, 3H), 7.72-7.71 (d, 1H), 7.41-7.40 (d, 1H), 1.64 (s, 6H); LCMS (ESI): m/z 369.1 (M+H).

Example 7

Synthesis of Compound 7

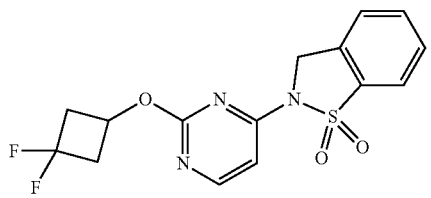 [SMILES: O=S1(=O)c2ccccc2CN1c1ccnc(OC2CC(F)(F)C2)n1]

Compound 7 was synthesized in a manner similar to Compound 1. $^1$H NMR (Methanol-d$_4$, 400 MHz) δ 8.42 (d, J=5.52 Hz, 1H), 7.92 (d, J=7.78 Hz, 1H), 7.86-7.79 (m, 1H), 7.75-7.65 (m, 2H), 7.03 (d, J=5.77 Hz, 1H), 5.16 (s, 2H), 4.91-4.88 (m, 1H), 3.27-3.18 (m, 2H), 2.93-2.86 (m, 2H); LCMS (ESI): m/z 354.0 (M+H).

Example 8

Synthesis of Compound 8

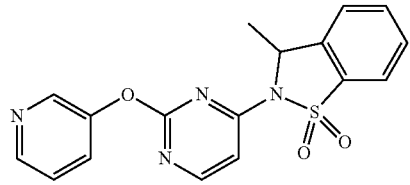 [SMILES: CC1c2ccccc2S(=O)(=O)N1c1ccnc(Oc2cccnc2)n1]

Compound 8 was synthesized in a manner similar to Compound 1 $^1$H NMR (DMSO-d$_6$, 400 MHz) δ 8.93-8.92 (d, 1H), 8.71-8.70 (d, 1H), 8.57-8.56 (d, 1H), 8.30-8.29 (d, 1H), 8.06-8.04 (d, 1H), 7.89-7.85 (m, 2H), 7.80-7.78 (d, 1H), 7.72-7.70 (m, 1H), 7.22-7.20 (d, 1H), 5.68-5.64 (m, 1H), 1.57-1.55 (d, 3H); LCMS (ESI): m/z 355.0 (M+H).

Example 9

Synthesis of Compound 9

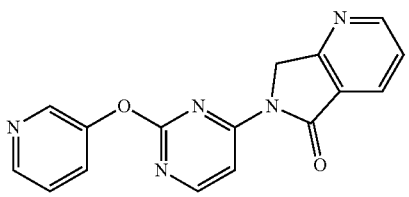 [SMILES: O=C1c2cccnc2CN1c1ccnc(Oc2cccnc2)n1]

Compound 9 was synthesized in a manner similar to Compound 1 $^1$H NMR (DMSO-d$_6$, 400 MHz) δ 9.09-9.08 (d, 1H), 8.90-8.89 (d, 1H), 8.80-8.79 (d, 1H), 8.63-8.62 (d, 1H), 8.48 (s, 1H), 8.30-8.28 (m, 2H), 8.08-8.06 (m, 1H), 7.64-7.62 (m, 1H), 4.97 (s, 2H); LCMS (ESI): m/z 306.1 (M+H).

Example 10

Synthesis of Compound 10

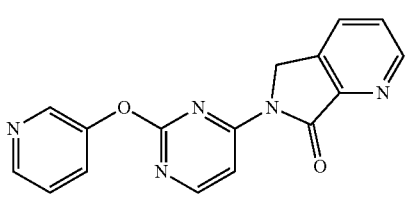 [SMILES: O=C1c2ncccc2CN1c1ccnc(Oc2cccnc2)n1]

Compound 10 was synthesized in a manner similar to Compound 1. $^1$H NMR (DMSO-d$_6$, 400 MHz) δ 8.82-8.81 (d, 1H), 8.60-8.57 (m, 2H), 8.53-8.52 (d, 1H), 8.30-8.29 (d, 1H), 8.21-8.19 (d, 1H), 7.82-7.81 (d, 1H), 7.72-7.69 (m, 1H), 7.58-7.56 (m, 1H), 4.98 (s, 2H); LCMS (ESI): m/z 306.1 (M+H).

Example 11

Synthesis of Compound 11

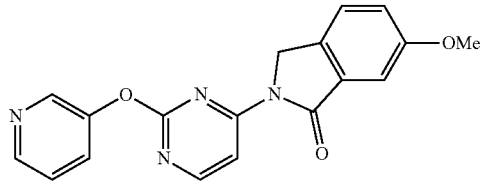 [SMILES: COc1ccc2c(c1)C(=O)N(c1ccnc(Oc3cccnc3)n1)C2]

Compound 11 was synthesized in a manner similar to Compound 1. $^1$H NMR (DMSO-d$_6$, 400 MHz) δ 8.78-8.65 (m, 2H), 8.53 (d, J=4.52 Hz, 1H), 8.07-7.99 (d, J=7.53 Hz, 1H), 7.65-7.49 (m, 2H), 7.32-7.23 (m, 2H), 6.96 (d, J=5.52 Hz, 1H), 4.87 (s, 2H), 3.85 (s, 3H); LCMS (ESI): m/z 335.1 (M+H).

Example 12

Synthesis of Compound 12

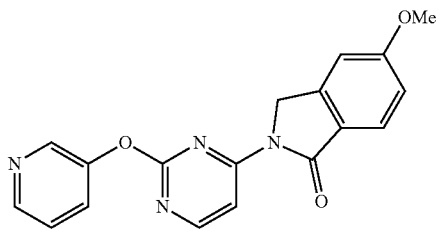 [SMILES: COc1ccc2c(c1)CN(c1ccnc(Oc3cccnc3)n1)C2=O]

Compound 12 was synthesized in a manner similar to Compound 1. $^1$H NMR (DMSO-d$_6$, 400 MHz) δ 8.75-8.63 (m, 2H), 8.58-8.42 (m, 1H), 8.07-7.92 (m, 1H), 7.70 (d, J=8.53 Hz, 1H), 7.55 (dd, J=8.41, 4.64 Hz, 1H), 7.23 (s, 1H), 7.14-7.04 (m, 1H), 6.93 (d, J=5.77 Hz, 1H), 4.87 (s, 2H), 3.93-3.80 (m, 3H); LCMS (ESI): m/z 335.0 (M+H).

Examples 13 and 14

Synthesis of Compounds 13 and 14

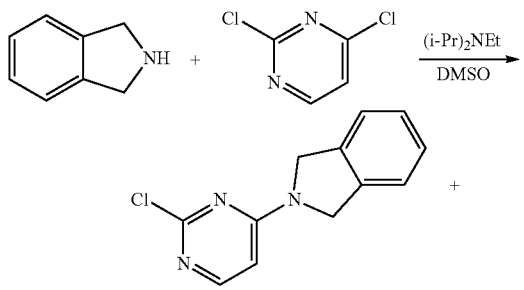

Compound 13

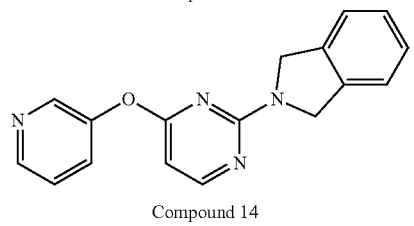

Compound 14

Step 1.

Isoindoline (175 mg, 1.47 mmol), and diisopropylethylamine (260 mg, 2.01 mmol) were dissolved in DMSO (4 mL). The resulting mixture was warmed up to 30° C., and 1,4-dichloropyrimidine (199 mg, 1.34 mmol) was added. Upon completion, water (30 mL) was added and the resulting mixture was extracted with EtOAc (60 mL). The organic phase was washed with brine, filtered, and concentrated under reduced pressure to yield a mixture of 6 and 6A (440 mg), which was submitted to the next step without further purification.

Step 2.

A mixture of 6 and 6A (240 mg, 0.31 mmol), pyridyl-3-ol (48 mg, 0.51 mmol), Cs$_2$CO$_3$ (202 mg, 0.62 mmol), and CsF (94 mg, 0.62 mmol) in DMSO (5 mL) was stirred at 120° C. for 2 hours. Upon completion, water (30 mL) was added and the resulting mixture was extracted with EtOAc (60 mL). The organic phase was washed with brine, filtered and concentrated under reduced pressure. The regioisomers were purified and separated by prep-HPLC to give Compound 13 (20 mg, 21%) and Compound 14 (9 mg, 9%), both as white solids. Compound 13. $^1$H NMR (DMSO-d$_6$, 400 MHz) δ 8.595-8.59 (d, 1H), 8.50-8.49 (d, 1H), 8.10-8.08 (d, 1H), 7.84-7.82 (d, 1H), 7.58 (m, 1H), 7.57-7.37 (m, 2H), 7.32-7.30 (m, 2H), 6.50-6.48 (d, 1H), 4.78-4.70 (d, 4H); LCMS (ESI): m/z: 291.2 (M+H). Compound 14. $^1$H NMR (DMSO-d$_6$, 400 MHz) δ 8.667-8.661 (d, 1H), 8.56-8.55 (d, 1H), 8.37-8.36 (d, 1H), 7.93-7.90 (d, 1H), 7.64-7.60 (m, 1H), 7.35-7.27 (m, 4H), 6.42-6.40 (d, 1H), 4.79 (s, 2H), 4.50 (s, 2H); LCMS (ESI): m/z 291.2 (M+H).

Example 15

Synthesis of Compound 15

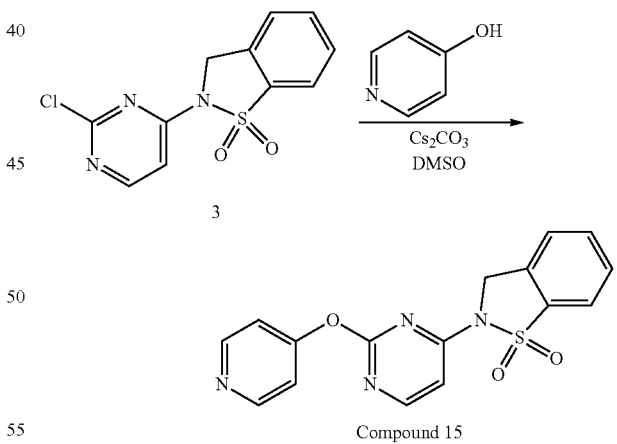

Compound 15

A mixture of 3 (40 mg, 0.14 mmol), pyridin-4-ol (16 mg, 0.170 mmol), and Cs$_2$CO$_3$ (92 mg, 0.28 mmol) in DMF (2 mL) was stirred at 45° C. for 1.5 hours. Upon completion, the mixture was filtered and concentrated under reduced pressure. Purification by prep-HPLC (0.04% HCl/CH$_3$CN/H$_2$O system) resulted in 10 mg (21%) of Compound 15 as white solid. $^1$H NMR (DMSO-d$_6$, 400 MHz) δ 8.85-8.83 (d, 2H), 8.75-8.74 (d, 1H), 8.08-8.06 (d, 1H), 7.89-7.85 (m, 1H), 7.77-7.70 (m, 2H), 7.23-7.19 (m, 1H), 6.37-6.35 (d, 2H), 5.33 (s, 2H); LCMS (ESI): m/z 341.0 (M+H).

Example 16

Synthesis of Compound 16

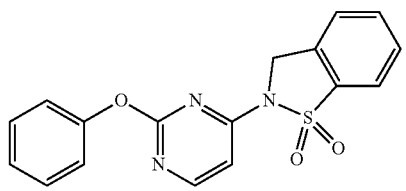 [SMILES: O=S1(=O)c2ccccc2CN1c1ccnc(Oc2ccccc2)n1]

Compound 16 was synthesized in a manner similar to Compound 15. $^1$H NMR: (DMSO-d$_6$, 400 MHz) δ 8.45-8.44 (d, 1H), 8.04-8.03 (d, 1H), 7.83-7.73 (m, 1H), 7.71-7.67 (m, 2H), 7.44-7.40 (m, 2H), 7.24-7.22 (m, 3H), 7.06-7.05 (d, 1H), 5.15 (s, 2H); LCMS (ESI): m/z 340.0 (M+H).

Example 17

Synthesis of Compound 17

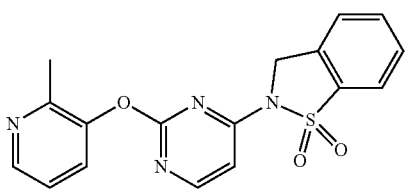 [SMILES: Cc1ncccc1Oc1nccc(N2Cc3ccccc3S2(=O)=O)n1]

Compound 17 was synthesized in a manner similar to Compound 15. $^1$H NMR (DMSO-d$_6$, 400 MHz) δ 8.53-8.52 (d, 1H), 8.50-8.49 (d, 1H), 8.04-8.02 (d, 1H), 7.85-7.81 (t, 1H), 7.72-7.69 (m, 2H), 7.67-7.59 (t, 1H), 7.09-7.07 (d, 1H), 5.16 (s, 2H), 2.43 (s 3H); LCMS (ESI): m/z 355 (M+H).

Example 18

Synthesis of Compound 18

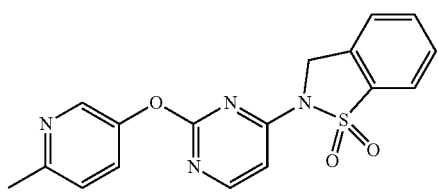 [SMILES: Cc1ccc(Oc2nccc(N3Cc4ccccc4S3(=O)=O)n2)cn1]

Compound 18 was synthesized in a manner similar to Compound 15. $^1$H NMR (DMSO-d$_6$, 400 MHz) δ 9.02 (d, 1H), 8.55-8.54 (d, 1H), 8.51 (d, 1H), 8.01-7.99 (d, 1H), 7.88-7.87 (d, 1H), 7.84-7.82 (t, 1H), 7.72-7.68 (m, 2H), 7.13-7.12 (d, 1H), 5.09 (s, 2H), 2.83 (s, 3H); LCMS (ESI): m/z 355 (M+H).

Example 19

Synthesis of Compound 19

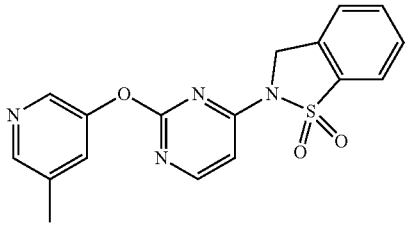 [SMILES: Cc1cncc(Oc2nccc(N3Cc4ccccc4S3(=O)=O)n2)c1]

Compound 19 was synthesized in a manner similar to Compound 15. $^1$H NMR (DMSO-d$_6$, 400 MHz) δ 8.79 (s, 1H), 8.60 (s, 1H), 8.55-8.53 (d, 1H), 8.23 (s, 1H), 8.04-8.02 (d, 1H), 7.84-7.82 (t, 1H), 7.73-7.67 (m, 2H), 7.10-7.09 (d, 1H), 5.17 (s, 2H), 2.45 (s, 3H); LCMS (ESI): m/z 355 (M+H).

Example 20

Synthesis of Compound 20

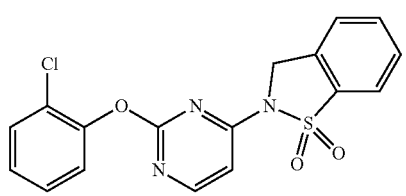

Compound 20 was synthesized in a manner similar to Compound 15. $^1$H NMR (DMSO-d$_6$, 400 MHz) δ 8.44-8.43 (d, 1H), 8.05-8.03 (d, 1H), 7.83-7.81 (t, 1H), 7.73-7.69 (m, 2H), 7.59-7.57 (d, 1H), 7.42-7.40 (m, 2H), 7.33-7.71 (m, 1H), 7.08-7.07 (d, 1H), 5.17 (s, 2H); LCMS (ESI): m/z 374 (M+H).

Example 21

Synthesis of Compound 21

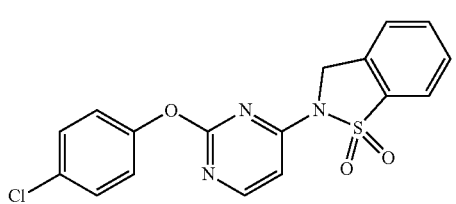 [SMILES: O=S1(=O)c2ccccc2CN1c1ccnc(Oc2ccc(Cl)cc2)n1]

Compound 21 was synthesized in a manner similar to Compound 15. $^1$H NMR (DMSO-d$_6$, 400 MHz) δ 8.48-8.47 (d, 1H), 8.08-8.04 (d, 1H), 7.84-7.82 (t, 1H), 7.75-7.68 (m, 2H), 7.49-7.47 (d, 2H), 7.32-7.30 (d, 1H), 7.10-7.08 (d, 1H), 5.16 (s, 2H); LCMS (ESI): m/z 374 (M+H).

Example 22

Synthesis of Compound 22

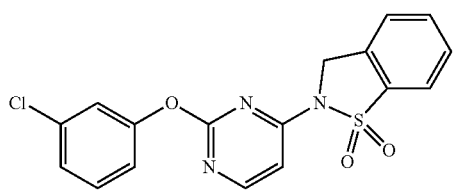 [SMILES: O=S1(=O)c2ccccc2CN1c1ccnc(Oc2cccc(Cl)c2)n1]

Compound 22 was synthesized in a manner similar to Compound 15. ¹H NMR (DMSO-d$_6$, 400 MHz) δ 8.49-8.48 (d, 1H), 8.07-8.05 (d, 1H), 7.85-7.75 (m, 1H), 7.73-7.70 (m, 2H), 7.47-7.43 (m, 2H), 7.35 (d, 1H), 7.27 (d, 1H), 7.09-7.08 (d, 1H), 5.18 (s, 2H); LCMS (ESI): m/z 374.0 (M+H).

Example 23

Synthesis of Compound 23

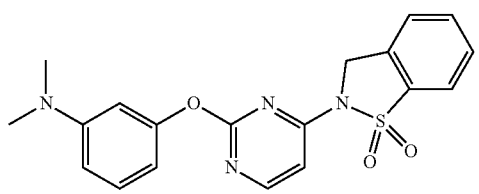 [SMILES: CN(C)c1cccc(Oc2nccc(N3Cc4ccccc4S3(=O)=O)n2)c1]

Compound 23 was synthesized in a manner similar to Compound 15. ¹H NMR (DMSO-d$_6$, 400 MHz) δ 8.49-8.48 (d, 1H), 8.06-8.04 (d, 1H), 7.84-7.82 (m, 1H), 7.75-7.68 (m, 2H), 7.41-7.39 (m, 1H), 7.14-7.06 (m, 3H), 6.93 (bs, 1H), 5.17 (s, 2H), 3.01 (s, 6H); LCMS (ESI): m/z 383.0 (M+H).

Example 24

Synthesis of Compound 24

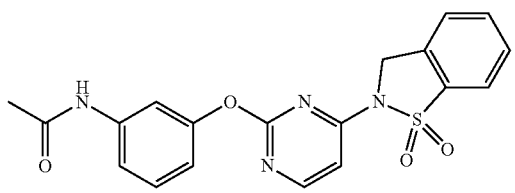 [SMILES: CC(=O)Nc1cccc(Oc2nccc(N3Cc4ccccc4S3(=O)=O)n2)c1]

Compound 24 was synthesized in a manner similar to Compound 15. ¹H NMR (DMSO-d$_6$, 400 MHz) δ 10.06 (s, 1H), 8.47-8.46 (d, 1H), 8.07-8.05 (d, 1H), 7.87-7.83 (m, 1H), 7.75-7.71 (m, 2H), 7.55 (s, 1H), 7.37-7.33 (m, 2H), 7.09-7.08 (d, 1H), 6.91-6.90 (d, 1H), 5.19 (s, 2H), 2.04 (s, 3H); LCMS (ESI): m/z 397.0 (M+H).

Example 25

Synthesis of Compound 25

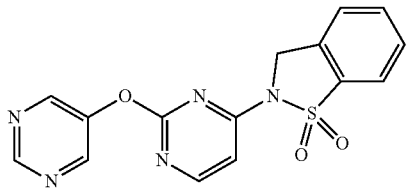 [SMILES: O=S1(=O)c2ccccc2CN1c1ccnc(Oc2cncnc2)n1]

Compound 25 was synthesized in a manner similar to Compound 15. ¹H NMR (DMSO-d$_6$, 400 MHz) δ 9.10 (s, 1H), 8.91 (s, 2H), 8.54-8.52 (d, 1H), 8.06-8.04 (d, 1H), 7.86-7.82 (m, 1H), 7.74-7.68 (m, 2H), 7.12-7.10 (d, 1H), 5.17 (s, 2H); LCMS (ESI): m/z 342.0 (M+H).

Example 26

Synthesis of Compound 26

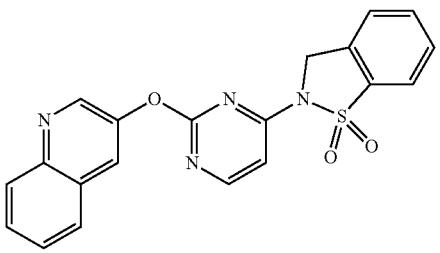 [SMILES: O=S1(=O)c2ccccc2CN1c1ccnc(Oc2cnc3ccccc3c2)n1]

Compound 26 was synthesized in a manner similar to Compound 15. ¹H NMR (DMSO-d$_6$, 400 MHz) δ 8.91-8.90 (d, 1H), 8.52-8.50 (d, 1H), 8.34-8.33 (d, 1H), 8.09-7.99 (m, 3H), 7.84-7.65 (m, 4H), 7.12-7.11 (d, 1H), 5.19 (s, 2H); LCMS (ESI): m/z 391.0 (M+H).

Example 27

Synthesis of Compound 27

Compound 27 was synthesized in a manner similar to Compound 15. ¹H NMR (DMSO-d$_6$, 400 MHz) δ 8.89-8.87 (d, 1H), 8.57-8.55 (d, 1H), 8.28-8.26 (d, 1H), 8.23-8.21 (d, 1H), 8.11-8.09 (d, 1H), 7.87 (m, 1H), 7.79 (m, 1H), 7.73-

7.68 (m, 2H), 7.47 (m, 1H), 7.42-7.40 (d, 1H), 6.31-6.29 (d, 1H), 5.32 (s, 2H); LCMS (ESI): m/z 391.0 (M+H).

Example 28

Synthesis of Compound 28

Compound 28 was synthesized in a manner similar to Compound 15. ¹H NMR (DMSO-d$_6$, 400 MHz) δ 8.71 (s, 1H), 8.59-8.55 (m, 2H), 8.27-8.27 (d, 1H), 7.87-7.85 (m, 1H), 7.76-7.71 (m, 2H), 7.64 (d, 1H), 4.99 (s, 2H); LCMS (ESI): m/z 305.0 (M+H).

Example 29

Synthesis of Compound 29

Compound 29 was synthesized in a manner similar to Compound 15. ¹H NMR (DMSO-d$_6$, 400 MHz) δ 8.91-8.89 (d, 1H), 8.71-8.69 (d, 1H), 8.27 (d, 1H), 8.05-8.03 (d, 1H), 7.85-7.83 (d, 1H), 7.78-7.72 (m, 2H), 7.64-7.62 (d, 1H), 7.32 (m, 1H), 7.24-7.22 (d, 1H), 7.00-6.99 (d, 1H), 6.80-6.79 (d, 1H), 5.28 (s, 2H); LCMS (ESI): m/z 363.0 (M+H).

Example 30

Synthesis of Compound 30

Compound 30 was synthesized in a manner similar to Compound 15. ¹H NMR (DMSO-d$_6$, 400 MHz) δ 9.32 (s, 1H), 9.23-9.21 (d, 1H), 8.83-8.81 (d, 2H), 8.06-8.04 (d, 1H), 7.75-7.68 (m, 2H), 7.25-7.17 (m, 3H); LCMS (ESI): m/z 364.0 (M+H).

Example 31

Synthesis of Compound 31

Compound 31 was synthesized in a manner similar to Compound 15. ¹H NMR (DMSO-d$_6$, 400 MHz) δ 9.14 (s, 1H), 8.77-8.72 (m, 2H), 8.09-8.07 (d, 1H), 7.83-7.81 (d, 1H), 7.73-7.68 (m, 3H), 7.35-7.13 (d, 1H), 5.33 (s, 2H); LCMS (ESI): m/z 364.0 (M+H).

Example 32

Synthesis of Compound 32

Compound 32 was synthesized in a manner similar to Compound 15. ¹H NMR (DMSO-d$_6$, 400 MHz) δ 9.42 (s, 1H), 8.62 (s, 1H), 8.44-8.42 (d, 1H), 8.35-8.33 (d, 1H), 8.04 (s, 1H), 7.90-7.83 (m, 4H), 7.75-7.71 (m, 2H), 7.11-7.10 (d, 1H), 7.47 (m, 1H), 5.20 (s, 2H); LCMS (ESI): m/z 391.0 (M+H).

Example 33

Synthesis of Compound 33

Compound 33 was synthesized in a manner similar to Compound 15. ¹H NMR (DMSO-d$_6$, 400 MHz) δ 8.44-8.42 (d, 1H), 7.90-7.88 (d, 1H), 7.79-7.77 (m, 1H), 7.67-7.66 (m, 2H), 7.59-7.57 (d, 1H), 7.51-7.50 (d, 1H), 7.24-7.21 (m, 2H), 5.03 (s, 2H); LCMS (ESI): m/z 407.9 (M+H).

Example 34

Synthesis of Compound 34

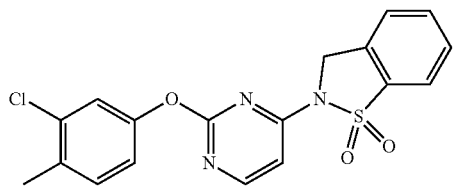 [SMILES: Cc1ccc(Oc2nccc(N3Cc4ccccc4S3(=O)=O)n2)cc1Cl]

Compound 34 was synthesized in a manner similar to Compound 15. $^1$H NMR (DMSO-d$_6$, 400 MHz) δ 8.46-8.44 (d, 1H), 8.05-8.03 (d, 1H), 7.83-7.81 (m, 1H), 7.73-7.69 (m, 2H), 7.40-7.37 (d, 2H), 7.16-7.13 (m, 1H), 7.06-7.05 (d, 1H), 5.16 (s, 2H), 2.32 (s, 3H); LCMS (ESI): m/z 388.0 (M+H).

Example 35

Synthesis of Compound 35

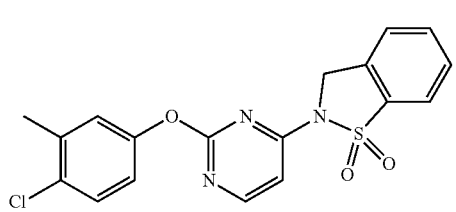 [SMILES: Cc1cc(Oc2nccc(N3Cc4ccccc4S3(=O)=O)n2)ccc1Cl]

Compound 35 was synthesized in a manner similar to Compound 15. $^1$H NMR (DMSO-d$_6$, 400 MHz) δ 8.46-8.45 (d, 1H), 8.05-8.03 (d, 1H), 7.83-7.81 (m, 1H), 7.74-7.68 (m, 2H), 7.45-7.42 (d, 1H), 7.28 (s, 1H), 7.13-7.04 (d, 2H), 5.15 (s, 2H), 2.32 (s, 3H); LCMS (ESI): m/z 388.0 (M+H).

Example 36

Synthesis of Compound 36

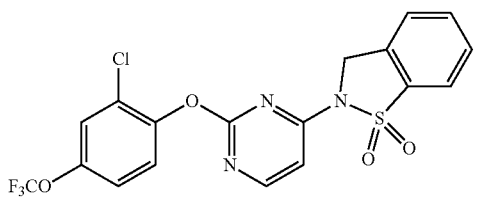 [SMILES: O=S1(=O)c2ccccc2CN1c1ccnc(Oc2ccc(OC(F)(F)F)cc2Cl)n1]

Compound 36 was synthesized in a manner similar to Compound 15. $^1$H NMR (DMSO-d$_6$, 400 MHz) δ 8.51 (d, J=5.77 Hz, 1H), 8.09 (d, J=7.78 Hz, 1H), 7.92-7.84 (m, 1H), 7.79-7.66 (m, 4H), 7.41 (d, J=8.53 Hz, 1H), 7.12 (d, J=5.77 Hz, 1H), 5.20 (s, 2H); LCMS (ESI): m/z 458.0 (M+H).

Example 37

Synthesis of Compound 37

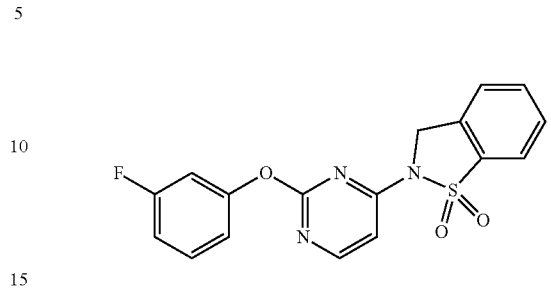

Compound 37 was synthesized in a manner similar to Compound 15. $^1$H NMR (DMSO-d$_6$, 400 MHz) δ 8.51-8.49 (d, 1H), 8.08-8.06 (d, 1H), 7.88-7.86 (d, 1H), 7.76-7.71 (m, 2H), 7.49-7.47 (d, 1H) 7.27-7.24 (d, 1H), 7.14-7.09 (m, 3H), 5.18 (s, 2H); LCMS (ESI): m/z: 358.0 (M+H).

Example 38

Synthesis of Compound 38

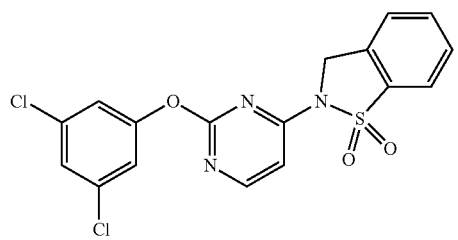 [SMILES: O=S1(=O)c2ccccc2CN1c1ccnc(Oc2cc(Cl)cc(Cl)c2)n1]

Compound 38 was synthesized in a manner similar to Compound 15. $^1$H NMR (DMSO-d$_6$, 400 MHz) δ 5.19 (s, 2H), 7.10 (d, 1H), 7.45-7.58 (m, 3H), 7.67-7.79 (m, 2H), 7.81-7.90 (m, 1H), 8.07 (d, 1H), 8.52 (d, 1H); LCMS (ESI): m/z 409.9 (M+H).

Example 39

Synthesis of Compound 39

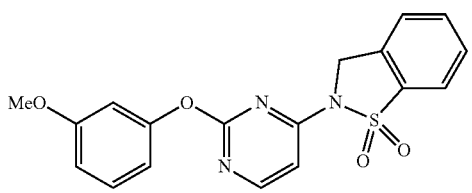 [SMILES: COc1cccc(Oc2nccc(N3Cc4ccccc4S3(=O)=O)n2)c1]

Compound 39 was synthesized in a manner similar to Compound 15. $^1$H NMR (DMSO-d$_6$, 400 MHz) δ 8.49 (d, 1H), 8.09 (d, 1H), 7.91-7.83 (m, 1H), 7.80-7.68 (m, 2H), 7.35 (t, 1H), 7.09 (d, 1H), 6.91-6.80 (m, 3H), 5.20 (s, 2H), 3.78 (s, 3H); LCMS (ESI): m/z 370.0 (M+H).

Example 40

Synthesis of Compound 40

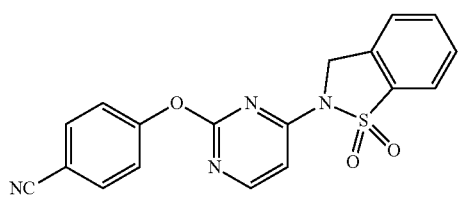 [SMILES: N#Cc1ccc(Oc2nccc(N3Cc4ccccc4S3(=O)=O)n2)cc1]

Compound 40 was synthesized in a manner similar to Compound 15. $^1$H NMR (DMSO-d$_6$, 400 MHz) δ 8.53 (d, 1H), 8.08 (d, 1H), 7.96 (d, 2H), 7.90-7.83 (m, 1H), 7.80-7.68 (m, 2H), 7.14 (d, 1H), 5.19 (s, 2H); LCMS (ESI): m/z 365.0 (M+H).

Example 41

Synthesis of Compound 41

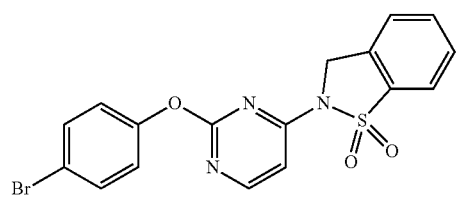

Compound 41 was synthesized in a manner similar to Compound 15. $^1$H NMR (DMSO-d$_6$, 400 MHz) δ 8.50 (d, 1H), 8.09 (d, 1H), 7.82-7.91 (m, 1H), 7.69-7.80 (m, 2H), 7.64 (d, 2H), 7.28 (d, 2H), 7.10 (d, 1H), 5.19 (s, 2H); LCMS (ESI): m/z 419.9 (M+H).

Example 42

Synthesis of Compound 42

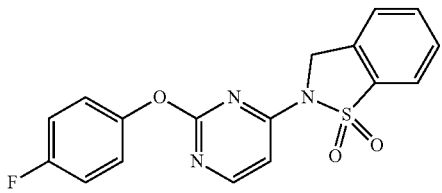 [SMILES: O=S1(=O)c2ccccc2CN1c1ccnc(Oc2ccc(F)cc2)n1]

Compound 42 was synthesized in a manner similar to Compound 15. $^1$H NMR (DMSO-d$_6$, 400 MHz) δ 8.49 (d, 1H), 8.08 (d, 1H), 7.90-7.82 (m, 1H), 7.79-7.67 (m, 2H), 7.38-7.23 (m, 4H), 7.09 (d, 1H), 5.19 (s, 2H); LCMS (ESI): m/z 358.0 (M+H).

Example 43

Synthesis of Compound 43

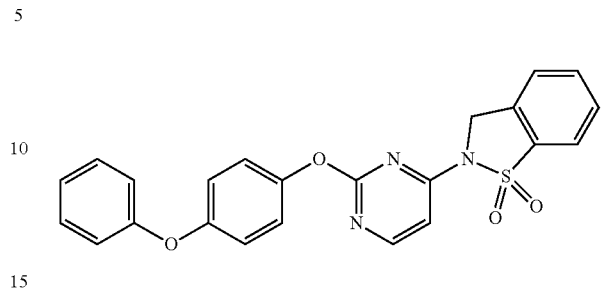

Compound 43 was synthesized in a manner similar to Compound 15. $^1$H NMR (DMSO-d$_6$, 400 MHz) δ 8.50 (d, J=5.27 Hz, 1H), 8.08 (d, J=7.78 Hz, 1H), 7.91-7.82 (m, 1H), 7.79-7.63 (m, 2H), 7.43 (t, J=7.53 Hz, 2H), 7.30 (d, J=8.53 Hz, 2H), 7.16 (t, J=7.28 Hz, 1H), 7.12-7.01 (m, 5H), 5.20 (s, 2H); LCMS (ESI): m/z 432.0 (M+H).

Example 44

Synthesis of Compound 44

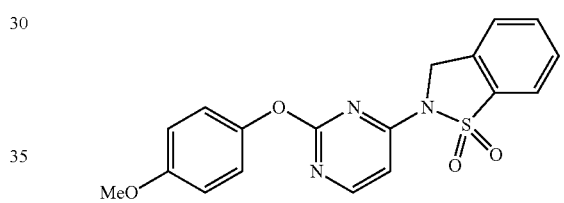

Compound 44 was synthesized in a manner similar to Compound 15. $^1$H NMR (DMSO-d$_6$, 400 MHz) δ 8.46 (d, J=5.27 Hz, 1H), 8.08 (d, J=7.78 Hz, 1H), 7.91-7.82 (m, 1H), 7.80-7.60 (m, 2H), 7.19 (d, J=8.53 Hz, 2H), 7.07 (d, J=5.52 Hz, 1H), 6.99 (d, J=8.53 Hz, 2H), 5.19 (s, 2H), 3.79 (s, 3H); LCMS (ESI): m/z 370.0 (M+H).

Example 45

Synthesis of Compound 45

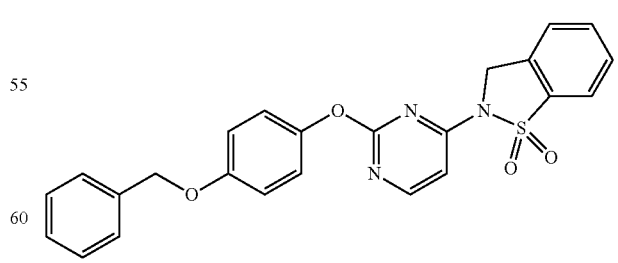

Compound 45 was synthesized in a manner similar to Compound 15. $^1$H NMR (DMSO-d$_6$, 400 MHz) δ 8.45-8.44 (d, 1H), 8.08-8.06 (d, 1H), 7.84 (m, 1H), 7.76-7.71 (m, 2H), 7.49-7.47 (m, 2H), 7.43 (m, 2H), 7.41-7.39 (m, 1H), 7.19-

7.17 (m, 2H), 7.07-7.05 (m, 3H), 5.18 (s, 2H), 5.13 (s, 2H); LCMS (ESI): m/z 446.1 (M+H).

Example 46

Synthesis of Compound 46

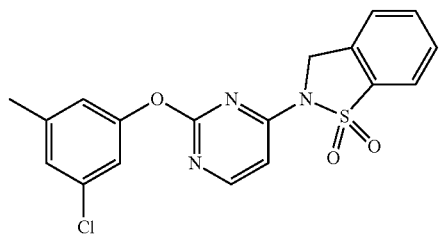 [SMILES: Cc1cc(Cl)cc(Oc2nccc(N3Cc4ccccc4S3(=O)=O)n2)c1]

Compound 46 was synthesized in a manner similar to Compound 15. $^1$H NMR (DMSO-d$_6$, 400 MHz) δ 8.51 (d, J=5.52 Hz, 1H), 8.09 (d, J=7.78 Hz, 1H), 7.93-7.83 (m, 1H), 7.80-7.61 (m, 2H), 7.22 (d, J=12.80 Hz, 2H), 7.13-6.95 (m, 2H), 5.21 (s, 2H), 2.35 (s, 3H); LCMS (ESI): m/z 388.0 (M+H).

Example 47

Synthesis of Compound 47

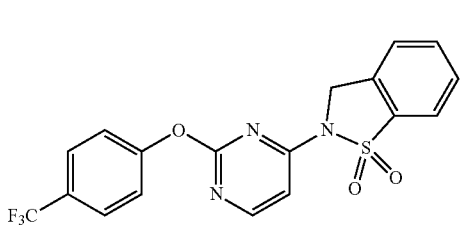 [SMILES: O=S1(=O)c2ccccc2CN1c1ccnc(Oc2ccc(C(F)(F)F)cc2)n1]

Compound 47 was synthesized in a manner similar to Compound 15. $^1$H NMR (DMSO-d$_6$, 400 MHz) δ 8.50 (d, J=5.73 Hz, 1H), 8.06 (d, J=7.94 Hz, 1H), 7.91-7.79 (m, 3H), 7.76-7.67 (m, 2H), 7.51 (d, J=8.82 Hz, 2H), 7.11 (d, J=5.73 Hz, 1H), 5.19 (s, 2H); LCMS (ESI): m/z 408.0 (M+H).

Example 48

Synthesis of Compound 48

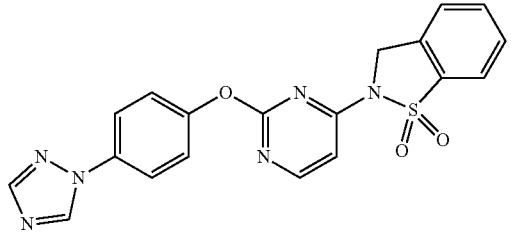 [SMILES: O=S1(=O)c2ccccc2CN1c1ccnc(Oc2ccc(-n3cncn3)cc2)n1]

Compound 48 was synthesized in a manner similar to Compound 15. $^1$H NMR (DMSO-d$_6$, 400 MHz) δ 9.30 (s, 1H), 8.50 (d, J=5.73 Hz, 1H), 8.25 (s, 1H), 8.06 (d, J=7.50 Hz, 1H), 7.92 (d, J=8.82 Hz, 2H), 7.87-7.81 (m, 1H), 7.76-7.63 (m, 2H), 7.47 (d, J=9.26 Hz, 2H), 7.09 (d, J=5.73 Hz, 1H), 5.18 (s, 2H); LCMS (ESI): m/z 407.0 (M+H).

Example 49

Synthesis of Compound 49

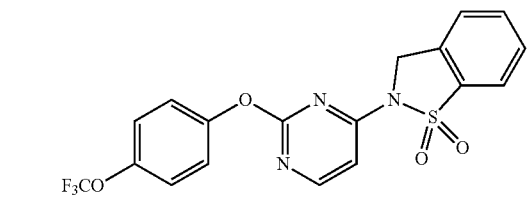 [SMILES: O=S1(=O)c2ccccc2CN1c1ccnc(Oc2ccc(OC(F)(F)F)cc2)n1]

Compound 49 was synthesized in a manner similar to Compound 15. $^1$H NMR (DMSO-d$_6$, 400 MHz) δ 8.50-8.48 (d, 1H), 8.09-8.07 (d, 1H), 7.86-7.84 (d, 1H), 7.76-7.70 (m, 2H), 7.47-7.40 (m, 4H), 7.10-7.09 (m, 1H), 5.19 (s, 2H); LCMS (ESI): m/z 424.0 (M+H).

Example 50

Synthesis of Compound 50

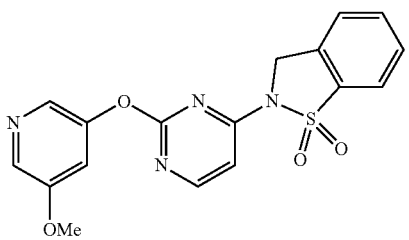 [SMILES: COc1cncc(Oc2nccc(N3Cc4ccccc4S3(=O)=O)n2)c1]

Compound 50 was synthesized in a manner similar to Compound 15. $^1$H NMR (DMSO-d$_6$, 400 MHz) δ 8.55-8.53 (d, 1H), 8.37 (m, 2H), 8.08-8.06 (d, 1H), 7.88-7.84 (t, 1H), 7.76-7.69 (m, 3H), 7.11-7.09 (m, 1H), 5.19 (s, 2H), 3.89 (s, 3H); LCMS (ESI): m/z 371.0 (M+H).

Example 51

Synthesis of Compound 51

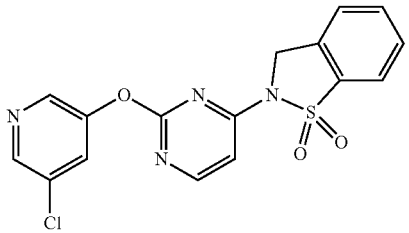 [SMILES: O=S1(=O)c2ccccc2CN1c1ccnc(Oc2cncc(Cl)c2)n1]

Compound 51 was synthesized in a manner similar to Compound 15. $^1$H NMR (DMSO-d$_6$, 400 MHz) δ 8.59-8.57 (m, 2H), 8.54-8.52 (m, 1H), 8.12 (s, 1H), 8.08-8.06 (d, 1H), 7.86-7.84 (m, 1H), 7.76-7.71 (m, 2H), 7.12-7.10 (d, 1H), 5.19 (s, 2H); LCMS (ESI): m/z 375.0 (M+H).

Example 52

Synthesis of Compound 52

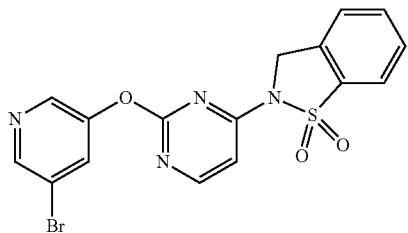 [SMILES: O=S1(=O)c2ccccc2CN1c1ccnc(Oc2cncc(Br)c2)n1]

Compound 52 was synthesized in a manner similar to Compound 15. ¹H NMR (DMSO-d$_6$, 400 MHz) δ 8.65-8.62 (m, 2H), 8.54-8.52 (d, 1H), 8.23 (s, 1H), 8.08-8.06 (d, 1H), 7.86-7.84 (m, 1H), 7.76-7.71 (m, 2H), 7.11-7.10 (d, 1H), 5.19 (s, 2H); LCMS (ESI): m/z 419.0 (M+H).

Example 53

Synthesis of Compound 53

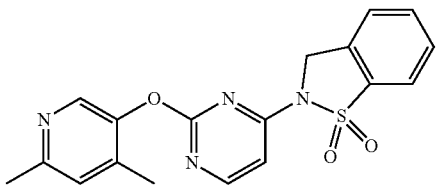 [SMILES: Cc1cc(C)c(Oc2nccc(N3Cc4ccccc4S3(=O)=O)n2)cn1]

Compound 53 was synthesized in a manner similar to Compound 15. ¹H NMR (DMSO-d$_6$, 400 MHz) δ 8.72 (s, 1H); 8.50 (d, 1H), 8.03 (d, 1H), 7.87-7.80 (m, 1H), 7.77-7.66 (m, 3H), 7.10 (d, 1H), 5.18 (s, 2H), 2.66 (s, 3H), 2.28 (s, 3H); LCMS (ESI): m/z 369.1 (M+H).

Example 54

Synthesis of Compound 54

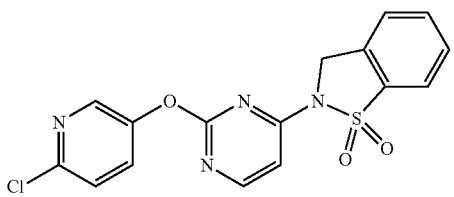 [SMILES: O=S1(=O)c2ccccc2CN1c1ccnc(Oc2ccc(Cl)nc2)n1]

Compound 54 was synthesized in a manner similar to Compound 15. ¹H NMR (DMSO-d$_6$, 400 MHz) δ 8.53-8.51 (d, 1H), 8.46-8.45 (d, 1H), 8.08-8.06 (d, 1H), 7.91-7.90 (d, 1H), 7.86 (m, 1H), 7.76-7.71 (m, 2H), 7.64-7.62 (d, 1H), 7.12-7.10 (d, 1H), 5.18 (s, 2H); LCMS (ESI): m/z 375.0 (M+H).

Example 55

Synthesis of Compound 55

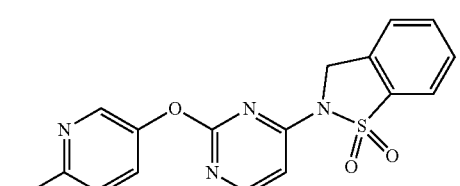

Compound 55 was synthesized in a manner similar to Compound 15. ¹H NMR (DMSO-d$_6$, 400 MHz) δ 8.83 (d, 1H), 8.56 (d, 1H), 8.23-8.17 (m, 1H), 8.14-8.05 (m, 2H), 7.91-7.83 (m, 1H), 7.79-7.68 (m, 2H), 7.15 (d, 1H), 5.19 (s, 2H); LCMS (ESI): m/z 366.0 (M+H).

Example 56

Synthesis of Compound 56

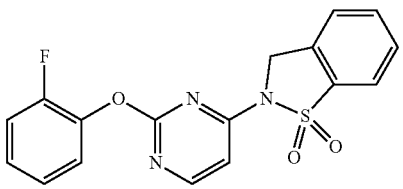

Compound 56 was synthesized in a manner similar to Compound 15. ¹H NMR (DMSO-d$_6$, 400 MHz) δ 8.48 (d, 1H), 8.07 (d, 1H), 7.90-7.81 (m, 1H), 7.79-7.67 (m, 2H), 7.48-7.22 (m, 4H), 7.10 (d, 1H), 5.20 (bs, 2H); LCMS (ESI): m/z 358.0 (M+H).

Example 57

Synthesis of Compound 57

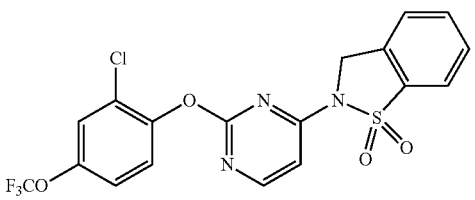 [SMILES: O=S1(=O)c2ccccc2CN1c1ccnc(Oc2ccc(OC(F)(F)F)cc2Cl)n1]

Compound 57 was synthesized in a manner similar to Compound 15. ¹H NMR (DMSO-d$_6$, 400 MHz) δ 8.48 (d, J=5.73 Hz, 1H), 8.06 (d, J=7.94 Hz, 1H), 7.91-7.81 (m, 1H), 7.80-7.67 (m, 3H), 7.60 (d, J=9.26 Hz, 1H), 7.52-7.43 (m, 1H), 7.15-7.06 (m, 1H), 5.27-5.14 (m, 2H); LCMS (ESI): m/z 458.0 (M+H).

Example 58

Synthesis of Compound 58

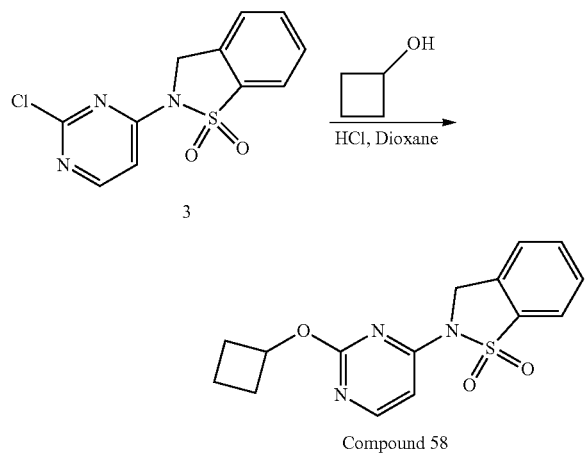

A mixture of 3 (30 mg, 0.11 mmol) and cyclobutanol (230 mg, 3.2 mmol) in HCl/dioxane (4M, 1.5 mL) was heated to 100° C. for 16 hours. Upon completion, the reaction mixture was concentrated under reduced pressure. Purification by prep-HPLC (0.04% HCl/CH$_3$CN/H$_2$O system) resulted in Compound 58 (1.6 mg, 5%) as a white solid. $^1$H NMR (DMSO-d$_6$, 400 MHz) δ ppm 8.45 (d, J=5.73 Hz, 1H), 8.02 (d, J=7.94 Hz, 1H), 7.86-7.79 (m, 1H), 7.76-7.65 (m, 2H), 6.89 (d, J=5.73 Hz, 1H), 5.16 (s, 2H), 5.14-5.05 (m, 1H), 2.15-2.01 (m, 2H), 1.78 (q, J=10.14 Hz, 1H), 1.70-1.55 (m, 1H); LCMS (ESI): m/z 318 (M+H).

Example 59

Synthesis of Compound 59

Compound 59 was synthesized in a manner similar to Compound 58. $^1$H NMR (DMSO-d$_6$, 400 MHz) δ 8.47-8.46 (d, 1H), 8.05-8.03 (d, 1H), 7.86-7.82 (m, 1H), 7.75-7.68 (m, 2H), 6.88-6.87 (d, 1H), 5.17 (s, 2H), 4.99-4.95 (m, 1H), 2.01-1.90 (m, 2H), 1.75-1.73 (m, 2H), 1.54-1.29 (m, 6H); LCMS (ESI): m/z 346 (M+H).

Example 60

Synthesis of Compound 60

Compound 60 was synthesized in a manner similar to Compound 58. $^1$H NMR (Methanol-d$_4$, 400 MHz) δ 8.27 (d, J=5.73 Hz, 1H), 7.87 (d, J=7.94 Hz, 1H), 7.82-7.74 (m, 1H), 7.72-7.62 (m, 2H), 6.47 (d, J=6.17 Hz, 1H), 5.62-5.50 (m, 1H), 5.19-5.05 (m, 2H), 2.20-2.05 (m, 2H), 1.90-1.74 (m, 4H), 1.73-1.57 (m, 2H); LCMS (ESI): m/z 332.0 (M+H).

Example 61

Synthesis of Compound 61

Compound 61 was synthesized in a manner similar to Compound 58. $^1$H NMR (Methanol-d$_4$, 400 MHz) δ 8.17-8.15 (d, 1H), 7.96-7.94 (d, 1H), 7.88-7.84 (m, 1H), 7.74-7.71 (m, 2H), 6.97 (bs, 1H), 5.27 (s, 2H), 4.47-4.48 (m, 1H), 4.32-4.29 (d, 1H), 4.21-4.16 (m, 1H), 3.89-3.86 (d, 1H), 3.56-3.53 (d, 1H), 3.40 (s, 3H); LCMS (ESI): m/z 333.0 (M+H).

Example 62

Synthesis of Compound 62

Compound 62 was synthesized in a manner similar to Compound 58. $^1$H NMR (DMSO-d$_6$, 400 MHz) δ 8.28-8.26 (d, 1H), 8.04-8.02 (d, 1H), 7.86-7.82 (t, 1H), 7.74-7.68 (m, 2H), 6.63-6.61 (d, 1H), 5.22 (s, 2H), 4.20-4.17 (m, 2H), 3.81-3.77 (m, 1H), 3.51-3.46 (t, 2H), 1.83-1.80 (m, 2H), 1.45-1.39 (m, 2H); LCMS (ESI): m/z 347.0 (M+H).

Example 63

Synthesis of Compound 63

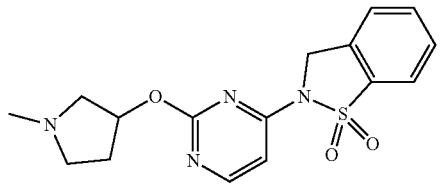 [SMILES: CN1CCC(Oc2nccc(N3Cc4ccccc4S3(=O)=O)n2)C1]

Compound 63 was synthesized in a manner similar to Compound 58. $^1$H NMR (DMSO-$d_6$, 400 MHz) δ 8.51-8.50 (d, 1H), 8.00-7.98 (d, 1H), 7.86-7.81 (m, 1H), 7.75-7.69 (m, 2H), 7.00-6.99 (d, 1H), 5.61-5.55 (m, 1H), 5.19 (s, 2H), 4.08 (m, 1H), 3.67-3.53 (m, 2H), 3.28-3.18 (m, 1H), 2.86 (s, 3H), 2.70-2.66 (m, 1H), 2.31-2.22 (m, 1H); LCMS (ESI): m/z 347.1 (M+H).

Example 64

Synthesis of Compound 64

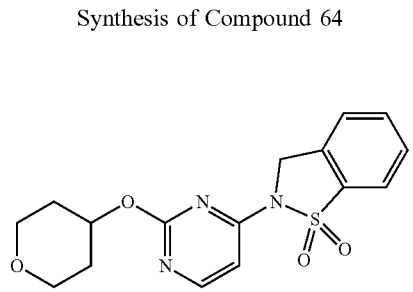

Compound 64 was synthesized in a manner similar to Compound 58. $^1$H NMR (DMSO-$d_6$, 400 MHz) δ 8.47-8.45 (d, 1H), 8.03-8.01 (d, 1H), 7.82-7.80 (d, 1H), 7.72-7.66 (m, 2H), 6.88-6.87 (d, 1H), 5.16 (s, 1H), 5.14-5.10 (m, 1H), 5.0 (s, 2H), 3.88-3.84 (m, 2H), 3.50-3.44 (m, 2H), 2.07-2.05 (m, 2H), 1.70-1.64 (m, 2H); LCMS (ESI): m/z 348.0 (M+H).

Example 65

Synthesis of Compound 65

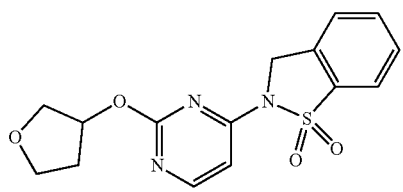 [SMILES: O=S1(=O)c2ccccc2CN1c1ccnc(OC2CCOC2)n1]

Compound 65 was synthesized in a manner similar to Compound 58. $^1$H NMR (Methanol-$d_4$, 400 MHz) δ 7.94-7.92 (d, 1H), 7.86-7.82 (t, 1H), 7.73-7.69 (m, 2H), 7.10-7.09 (d, 1H), 5.69 (s, 1H), 5.19 (s, 1H), 4.14-4.10 (m, 1H), 4.02-3.99 (m, 2H), 3.92-3.91 (m, 1H), 2.45-2.35 (m, 2H), 2.26-2.22 (m, 1H); LCMS (ESI): m/z 334.0 (M+H).

Example 66

Synthesis of Compound 66

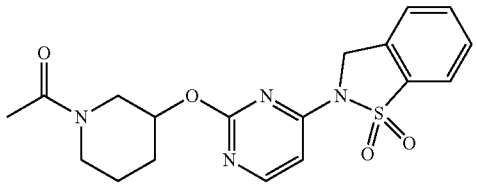 [SMILES: CC(=O)N1CCCC(Oc2nccc(N3Cc4ccccc4S3(=O)=O)n2)C1]

Compound 66 was synthesized in a manner similar to Compound 58. $^1$H NMR (DMSO-$d_6$, 400 MHz) δ 8.26-8.22 (d, 1H), 7.99-7.97 (d, 1H), 7.82-7.80 (d, 1H), 7.73-7.66 (m, 2H), 6.48-6.46 (d, 1H), 5.11 (s, 1H), 4.75 (s, 1H), 3.97-3.92 (m, 1H), 3.88-3.85 (m, 2H), 3.70-3.66 (m, 1H), 1.89 (m, 1H), 1.72 (m, 2H), 1.52 (m, 1H); LCMS (ESI): m/z 389.1 (M+H).

Example 67

Synthesis of Compound 67

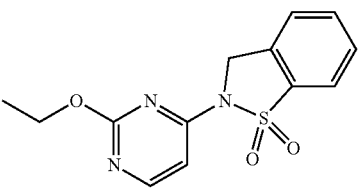 [SMILES: CCOc1nccc(N2Cc3ccccc3S2(=O)=O)n1]

Compound 67 was synthesized in a manner similar to Compound 58. $^1$H NMR (Methanol-$d_4$, 400 MHz) δ 8.42 (bs, 1H), 7.93 (d, J=7.94 Hz, 1H), 7.86-7.79 (m, 1H), 7.75-7.61 (m, 2H), 7.09 (d, J=6.17 Hz, 1H) 5.28-5.12 (m, 2H), 4.56 (q, J=7.06 Hz, 2H), 1.52-1.41 (m, 3H); LCMS (ESI): m/z 292.0 (M+H).

Example 68

Synthesis of Compound 68

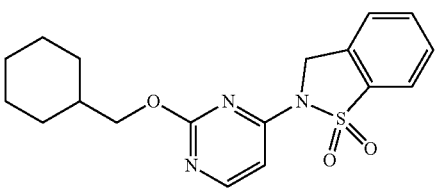 [SMILES: O=S1(=O)c2ccccc2CN1c1ccnc(OCC2CCCCC2)n1]

Compound 68 was synthesized in a manner similar to Compound 58. 1H NMR (DMSO-$d_6$, 400 MHz) δ 8.49 (d, J=5.77 Hz, 1H), 8.06 (d, J=7.78 Hz, 1H), 7.91-7.81 (m, 1H), 7.78-7.66 (m, 2H), 6.95 (d, J=5.77 Hz, 1H), 5.21 (s, 2H), 4.33 (d, J=7.03 Hz, 2H), 2.78 (q, J=7.40 Hz, 1H), 2.15-2.01 (m, 2H), 1.96-1.76 (m, 4H); LCMS (ESI): m/z 360.1 (M+H).

Example 69

Synthesis of Compound 69

Compound 69 was synthesized in a manner similar to Compound 58. $^1$H NMR (Methanol-$d_4$, 400 MHz) δ 8.40 (d, J=6.17 Hz, 1H), 7.93 (d, J=7.94 Hz, 1H), 7.78-7.86 (m, 1H), 7.74-7.65 (m, 2H), 7.13-7.02 (m, 1H), 5.20 (s, 2H), 4.36-4.27 (m, 2H), 1.96-1.64 (m, 6H), 1.40-1.05 (m, 5H); LCMS (ESI): m/z 332.1 (M+H).

Example 70

Synthesis of Compound 70

A mixture of 3 (30 mg, 0.11 mmol), benzyl alcohol (17 mg, 0.16 mmol), potassium carbonate (29 mg, 0.21 mmol), and cesium fluoride (33 mg, 0.21 mmol) in DIVIF (2 mL) was stirred at 65° C. for 10 hours under an inert atmosphere. Upon completion, the reaction mixture was filtered and concentrated under reduced pressure. Purification by prep-HPLC (0.04% HCl/CH$_3$CN/H$_2$O system) resulted in Compound 70 (2 mg, 5%). $^1$H NMR (DMSO-$d_6$, 400 MHz) δ 8.51-8.49 (d, 1H), 7.84-7.83 (d, 1H), 7.75-7.70 (m, 2H), 7.50-7.49 (d, 2H), 7.39-7.35 (m, 2H), 7.33-6.98 (m, 1H), 5.43 (s, 2H), 5.20 (s, 2H); LCMS (ESI): m/z 354.0 (M+H).

Example 71

Synthesis of Compound 71

Compound 71 was synthesized in a manner similar to Compound 70. $^1$H NMR (DMSO-$d_6$, 400 MHz) δ 9.94-9.91 (d, 2H), 9.08-9.04 (d, 1H), 8.88-8.06 (d, 1H), 8.40-8.38 (d, 1H), 8.17-8.15 (d, 1H), 7.93-7.91 (d, 1H), 7.82-7.70 (d, 1H), 7.76-7.64 (d, 1H), 6.16-6.13 (t, 1H), 5.48 (s, 2H), 4.90-4.89 (d, 2H); LCMS (ESI): m/z 355.0 (M+H).

Example 72

Synthesis of Compound 72

Compound 72 was synthesized in a manner similar to Compound 70. $^1$H NMR (Methanol-$d_4$, 400 MHz) δ 8.85-8.83 (d, 2H), 8.63-8.60 (d, 1H), 8.61-8.50 (d, 1H), 8.24-8.03 (m, 1H), 7.89-7.87 (d, 1H), 7.71-7.69 (m, 1H), 7.03-7.01 (d, 1H), 5.87 (s, 2H), 5.17-5.11 (d, 2H); LCMS (ESI): m/z 355.0 (M+H).

Example 73

Synthesis of Compound 73

Compound 73 was synthesized in a manner similar to Compound 70. $^1$H NMR (DMSO-$d_6$, 400 MHz) δ 8.83-8.82 (d, 2H), 8.48-8.47 (d, 1H), 8.18-8.16 (d, 2H), 7.88-7.79 (m, 2H), 7.70-7.68 (d, 2H), 7.00-6.99 (d, 1H), 5.82 (s, 2H), 5.09 (s, 2H); LCMS (ESI): m/z 355.0 (M+H).

Example 74

Synthesis of Compound 74

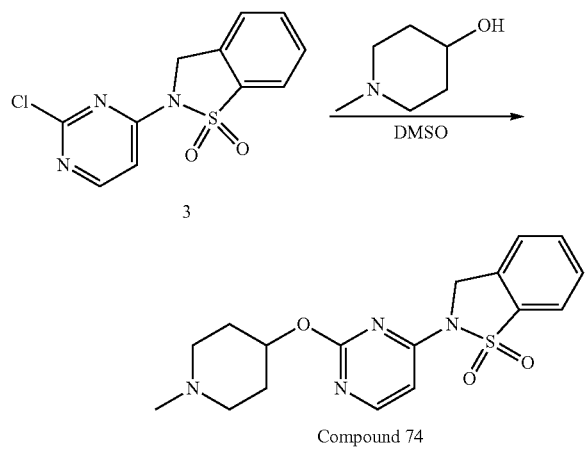

A mixture of 3 (30 mg, 0.11 mmol) and 1-methylpiperidin-4-ol (182 mg, 1.59 mmol) in DMSO (1.0 mL) was stirred at 50° C. for 2 hours. Purification by prep-HPLC (0.04% HCl/CH₃CN/H₂O system) resulted in Compound 74 (12 mg, 32%) as a white solid. $^1$H NMR (DMSO-d$_6$, 400 MHz) δ 8.51-8.50 (d, 1H), 7.95-7.92 (m, 1H), 7.86-7.84 (m, 1H), 7.75-7.66 (m, 2H), 7.11-7.06 (m, 1H), 5.22 (s, 2H), 4.77-4.74 (m, 1H), 3.69-3.66 (d, 1H), 3.51-3.48 (d, 1H), 3.38-3.34 (m, 2H), 2.95 (s, 3H), 2.65-2.63 (d, 1H), 2.50-2.46 (d, 1H), 2.28-2.21 (m, 1H), 2.11-2.04 (m, 1H); LCMS (ESI): m/z 361.0 (M+H).

Example 75

Synthesis of Compound 75

Step 1.

A mixture of 3 (200 mg, 0.71 mmol), methyl-2-hydroxyacetate (192 mg, 2.13 mmol), CsF (216 mg, 1.42 mmol) and potassium carbonate (196 mg, 1.42 mmol) in DMF (3 mL) was stirred at 120° C. for 4 hours under an inert atmosphere. The resulting mixture was filtered and purification with pre-HPLC (0.075% TFA/CH₃CN/H₂O system) resulted in 7 (60 mg, 25%).

Step 2.

To a solution of 7 (30 mg, 0.09 mmol) in MeOH (2 mL) was added NH₃.H₂O (9.4 mg, 0.27 mmol). The mixture was stirred at 60° C. for 2 hours. Upon completion, the reaction mixture was concentrated under reduced pressure and purification by prep-HPLC (0.04% HCl/CH₃CN/H₂O system) resulted in Compound 75 (2.5 mg, 8.5%) as a white solid. $^1$H NMR (DMSO-d$_6$, 400 MHz) δ 8.48 (d, 1H), 8.05 (d, 1H), 7.85 (d, 1H), 7.76-7.72 (t, 2H), 7.51 (s, 1H), 7.20 (d, 1H), 6.99 (d, 1H), 5.19 (s, 2H), 4.75 (s, 2H); LCMS (ESI): m/z 321.0 (M+H).

Example 76

Synthesis of Compound 76

Compound 76 was synthesized in a manner similar to Compound 75. $^1$H NMR (DMSO-d$_6$, 400 MHz) δ 10.23 (s, 1H), 8.50-8.48 (d, 1H), 8.06-8.04 (d, 1H), 7.84-7.82 (t, 1H), 7.70-7.65 (dd, 2H), 7.62-7.60 (d, 2H), 7.33-7.29 (t, 2H), 7.07-7.05 (t, 1H), 7.05-6.99 (d, 1H), 5.16 (s, 2H), 4.98 (s, 2H); LCMS (ESI): m/z 397 (M+H).

Example 77

Synthesis of Compound 77

-continued

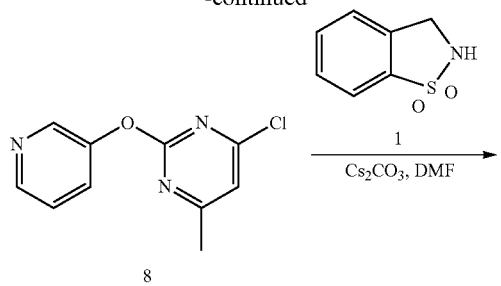

8

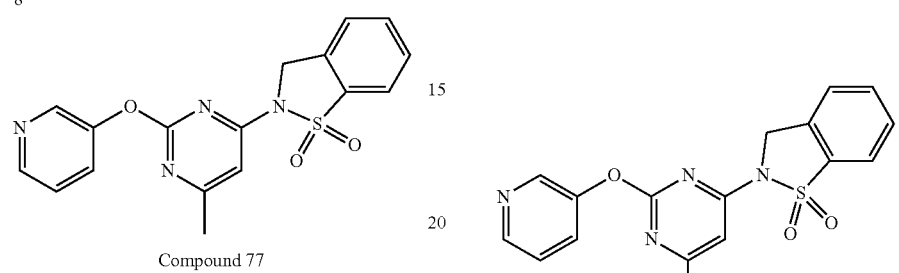

Compound 77

Step 1.

To a solution of 6-methyl-2,4-dichloropyrimidine (120 mg, 0.74 mmol) and pyridin-3-ol (70 mg, 0.74 mmol) in anhydrous DMF (4 mL) was added potassium carbonate (204 mg, 1.47 mmol) and the resulting mixture heated to 50° C. for 2 hours. Upon completion, the reaction mixture was poured into water (10 mL) and extracted with ethyl acetate (60 mL). The combined organic layer was washed with water (150 mL), saturated brine (80 mL), and dried over anhydrous sodium sulfate. Filtration and concentration under reduced pressure resulted in 8 (150 mg), which was submitted to the next step without further purification.

Step 2.

To a solution of 8 (150 mg, 0.54 mmol) and 1 (92 mg, 0.54 mmol) in anhydrous DMF (4 mL) was added cesium carbonate (353 mg, 1.08 mmol), and the resulting mixture was stirred at 40° C. for 2 hours. Upon completion, the reaction mixture was poured into water (10 mL) and extracted with ethyl acetate (60 mL). The combined organic layer was washed with saturated brine, dried over anhydrous sodium sulfate, filtered and concentrated under reduced pressure. Purification by prep-HPLC (0.04% HCl/CH$_3$CN/H$_2$O system) resulted in Compound 77 (3.9 mg, 9.0%) as a white solid. $^1$H NMR (DMSO-d$_6$, 400 MHz) δ 8.78 (d, 1H), 8.61 (d, 1H), 8.10-8.03 (m, 2H), 7.84 (d, 1H), 7.76-7.71 (m, 3H), 6.99 (s, 1H), 5.14 (s, 2H), 2.40 (s, 3H); LCMS (ESI): m/z 355.0 (M+H).

Example 78

Synthesis of Compound 78

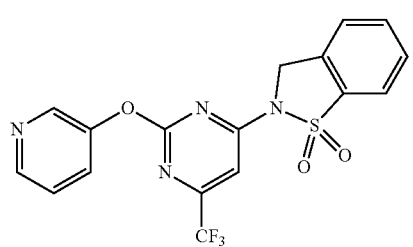 [SMILES: O=S1(=O)c2ccccc2CN1c1cc(C(F)(F)F)nc(Oc2cccnc2)n1]

Compound 78 was synthesized in a manner similar to Compound 77, $^1$H NMR (DMSO-d$_6$, 400 MHz) δ 9.14 (s, 1H), 8.80 (s, 1H), 8.63-8.61 (d, 1H), 8.17-8.15 (m, 1H), 7.89-7.80 (m, 2H), 7.70-7.67 (m, 2H), 7.43 (s, 1H), 5.15 (s, 2H); LCMS (ESI): m/z 409.0 (M+H).

Examples 79 and 80

Synthesis of Compounds 79 and 80

Compound 79

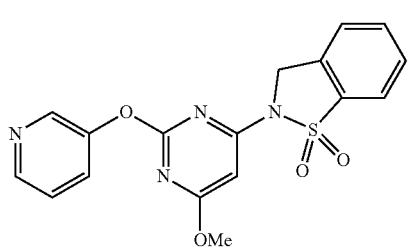 [SMILES: N#Cc1cc(N2Cc3ccccc3S2(=O)=O)nc(Oc2cccnc2)n1]

Compound 80

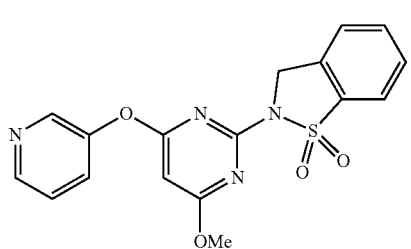

Compound 79 and Compound 80 were synthesized in a manner similar to Compound 77. Separation of isomers (~1:1 ratio) was achieved by prep-HPLC (0.04% HCl/CH$_3$CN/H$_2$O system). Compound 79. $^1$H NMR (DMSO-d$_6$, 400 MHz) δ 9.19 (s, 1H), 8.76-8.75 (d, 1H), 8.63-8.61 (d, 1H), 8.15-8.13 (m, 1H), 7.85-7.78 (m, 2H), 7.69-7.65 (m, 2H), 6.35 (s, 1H), 5.01 (s, 2H), 4.01 (s, 3H); LCMS (ESI): m/z 371.0 (M+H). Compound 80. $^1$H NMR (DMSO-d$_6$, 400 MHz) δ 9.20-9.19 (d, 1H), 8.75-8.73 (d, 1H), 8.58-8.57 (d, 1H), 8.14-8.11 (m, 1H), 7.83-7.77 (m, 2H), 7.68-7.64 (m, 2H), 6.28 (s, 1H), 5.11 (s, 2H), 4.10 (s, 3H); LCMS (ESI): m/z 371.0 (M+H).

Example 81

Synthesis of Compound 81

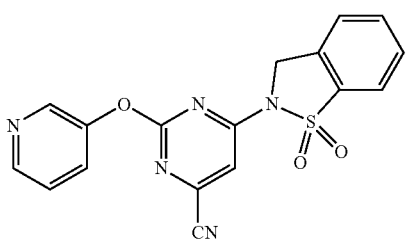

Compound 81 was synthesized in a manner similar to Compound 77. $^1$H NMR (DMSO-d$_6$, 400 MHz) δ 8.61 (s, 2H), 8.10-8.08 (d, 1H), 7.95-7.93 (d, 1H), 7.87-7.85 (d, 1H), 7.75-7.71 (m, 2H), 7.65 (m, 2H), 5.24 (s, 2H); LCMS (ESI): m/z 366 (M+H).

Example 82

Synthesis of Compound 82

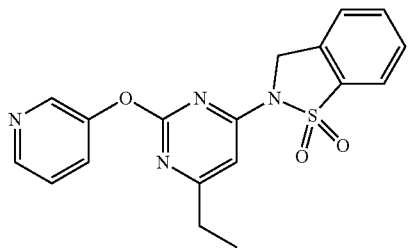 [SMILES: CCc1cc(N2Cc3ccccc3S2(=O)=O)nc(Oc2cccnc2)n1]

Compound 82 was synthesized in a manner similar to Compound 77. $^1$H NMR (DMSO-d$_6$, 400 MHz) δ 8.74 (bs, 1H); 8.58 (d, 1H), 8.09-7.98 (m, 2H), 7.89-7.82 (m, 1H), 7.72 (dd, 3H), 6.97 (s, 1H), 5.16 (s, 2H), 2.68 (q, 2H), 1.18 (t, 3H); LCMS (ESI): m/z 369.0 (M+H).

Example 83

Synthesis of Compound 83

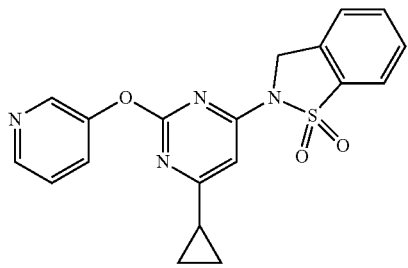 [SMILES: O=S1(=O)c2ccccc2CN1c1cc(C2CC2)nc(Oc2cccnc2)n1]

Compound 83 was synthesized in a manner similar to Compound 77. $^1$H NMR (Methanol-d$_4$, 400 MHz) δ 9.19 (d, J=1.76 Hz, 1H), 8.78 (d, J=5.73 Hz, 1H), 8.67 (dd, J=8.60, 1.54 Hz, 1H), 8.20 (dd, J=8.82, 5.73 Hz, 1H), 7.91-7.78 (m, 2H), 7.68 (dt, J=7.61, 3.47 Hz, 2H), 7.00 (s, 1H), 5.16-5.04 (m, 2H), 2.21-2.12 (m, 1H), 1.18-1.11 (m, 4H); LCMS (ESI): m/z 381.0 (M+H).

Example 84

Synthesis of Compound 84

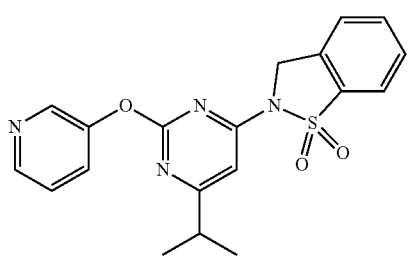 [SMILES: CC(C)c1cc(N2Cc3ccccc3S2(=O)=O)nc(Oc2cccnc2)n1]

Compound 84 was synthesized in a manner similar to Compound 77. $^1$H NMR (DMSO-d$_6$, 400 MHz) δ 8.92 (bs, 1H); 8.69 (d, 1H), 8.28 (d, 1H), 8.04 (d, 1H), 7.85 (t, 2H), 7.76-7.66 (m, 2H), 6.96 (s, 1H), 5.18 (s, 2H), 2.96 (m, 1H), 1.20 (d, 6H); LCMS (ESI): m/z 383.1 (M+H).

Example 85

Synthesis of Compound 85

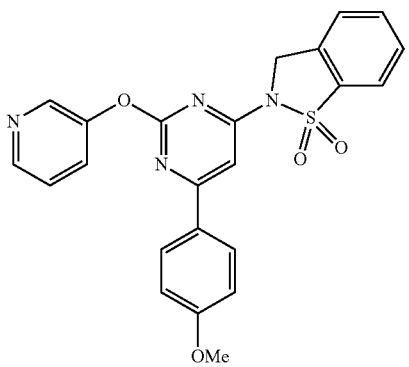 [SMILES: COc1ccc(-c2cc(N3Cc4ccccc4S3(=O)=O)nc(Oc3cccnc3)n2)cc1]

Compound 85 was synthesized in a manner similar to Compound 77. $^1$H NMR (DMSO-d$_6$, 400 MHz) δ 8.96 (s, 1H), 8.72-8.71 (d, 1H), 8.31 (s, 1H), 8.06-8.02 (m, 3H), 7.88-7.84 (t, 2H), 7.75-7.72 (m, 2H), 7.42 (s, 1H), 7.10-7.08 (d, 2H), 5.29 (s, 2H), 3.84 (s, 3H); LCMS (ESI): m/z 447.1 (M+H).

Examples 86 and 87

Synthesis of Compounds 86 and 87

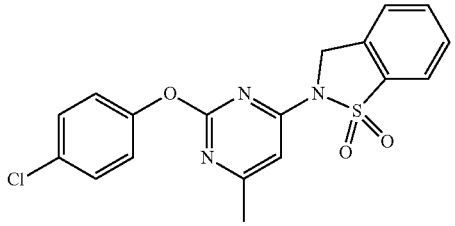

Compounds 86

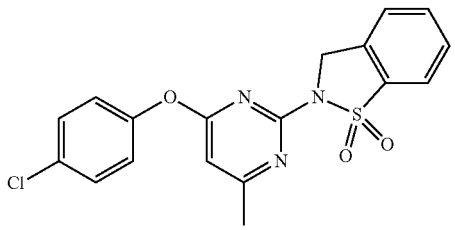

Compounds 87

Compound 86 and Compound 87 were synthesized in a manner similar to Compound 77. Separation of isomers was achieved by prep-HPLC (0.04% HCl/CH$_3$CN/H$_2$O system). Compound 86. $^1$H NMR (DMSO-d$_6$, 400 MHz) δ 8.07-8.05 (d, 1H), 7.84-7.82 (d, 1H), 7.74-7.70 (m, 2H), 7.50-7.48 (d, 2H), 7.32-7.30 (d, 2H), 6.96 (s, 1H), 5.14 (s, 2H), 3.37 (s, 3H); LCMS (ESI): m/z 388.0 (M+H). Compound 87. ¹H NMR (DMSO-d₆, 400 MHz) δ 7.97-7.95 (d, 1H), 7.79-7.77 (d, 1H), 7.73-7.71 (d, 1H), 7.67-7.65 (d, 1H), 7.53-7.51 (d, 2H), 7.39-7.37 (d, 2H), 6.63 (s, 1H), 5.04 (s, 2H), 2.42 (s, 3H); LCMS (ESI): m/z 388.0 (M+H).

Example 88

Synthesis of Compound 88

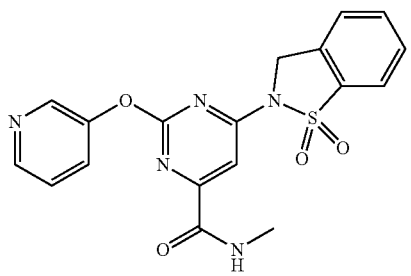 [SMILES: CNC(=O)c1cc(N2Cc3ccccc3S2(=O)=O)nc(Oc2cccnc2)n1]

Compound 88 was synthesized in a manner similar to Compound 77 NMR (DMSO-d₆, 400 MHz) δ 8.98-8.97 (d, 1H), 8.74-8.72 (t, 2H), 8.35-8.33 (d, 1H), 8.09-8.07 (d, 2H), 7.91-7.84 (m, 2H), 7.75-7.71 (t, 2H), 7.60 (s, 1H), 5.21 (s, 1H), 2.82-2.80 (d, 3H); LCMS (ESI): m/z 398.0 (M+H).

Example 89

Synthesis of Compound 89

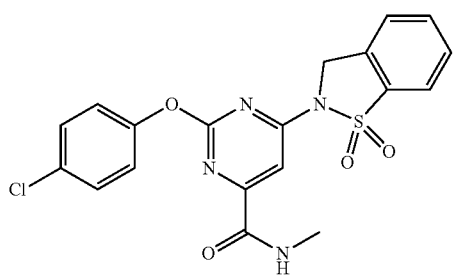 [SMILES: CNC(=O)c1cc(N2Cc3ccccc3S2(=O)=O)nc(Oc2ccc(Cl)cc2)n1]

Compound 89 was synthesized in a manner similar to Compound 77. ¹H NMR (DMSO-d₆, 400 MHz) δ 8.63 (s, 1H), 8.09-8.07 (d, 1H), 7.85-7.83 (d, 1H), 7.76-7.71 (m, 2H), 7.58 (s, 1H), 7.52-7.50 (d, 2H), 7.41-7.39 (d, 2H), 5.16 (s, 1H), 2.82-2.81 (d, 3H); LCMS (ESI): m/z 431.0 (M+H).

Example 90

Synthesis of Compound 90

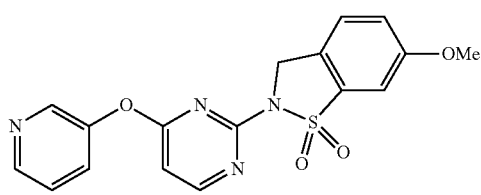 [SMILES: COc1ccc2c(c1)S(=O)(=O)N(c1nccc(Oc3cccnc3)n1)C2]

Compound 90 was synthesized in a manner similar to Compound 77. ¹H NMR (DMSO-d₆, 400 MHz) δ 8.56 (s, 1H), 8.50-8.48 (d, 2H), 7.80-7.78 (d, 1H), 7.64-7.62 (m, 2H), 7.52-7.51 (d, 1H), 7.41-7.39 (d, 1H), 7.08-7.07 (d, 1H), 5.07 (s, 2H), 3.88 (s, 3H); LCMS (ESI): m/z 371.0 (M+H).

Example 91

Synthesis of Compound 91

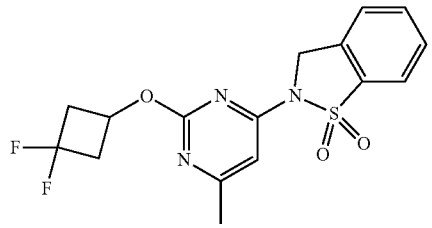 [SMILES: Cc1cc(N2Cc3ccccc3S2(=O)=O)nc(OC2CC(F)(F)C2)n1]

Compound 91 was synthesized in a manner similar to Compound 77 ¹H NMR (Methanol-d₄, 400 MHz) δ 7.98 (d, 1H), 7.93-7.85 (m, 1H), 7.79-7.71 (m, 2H), 7.13 (s, 1H), 5.40 (s, 1H), 5.28 (s, 2H), 3.42-3.33 (m, 2H), 3.03-2.91 (m, 2H), 2.62 (s, 3H); LCMS (ESI): m/z 368.1 (M+H).

Example 92

Synthesis of Compound 92

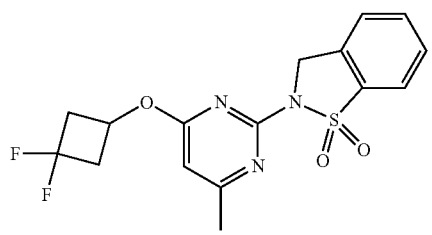 [SMILES: Cc1cc(OC2CC(F)(F)C2)nc(N2Cc3ccccc3S2(=O)=O)n1]

Compound 92 was synthesized in a manner similar to Compound 77. ¹H NMR (Methanol-d₄, 400 MHz) δ 7.89 (d, 1H), 7.81-7.75 (m, 1H), 7.71-7.64 (m, 2H), 6.46 (s, 1H), 5.26-5.16 (m, 1H), 5.12 (s, 2H), 3.29-3.21 (m, 2H), 2.81-2.68 (m, 2H), 2.42 (s, 3H); LCMS (ESI): m/z 368.0 (M+H).

Example 93

Synthesis of Compound 93

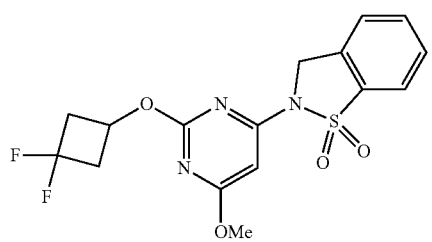 [SMILES: COc1cc(N2Cc3ccccc3S2(=O)=O)nc(OC2CC(F)(F)C2)n1]

Compound 93 was synthesized in a manner similar to Compound 77. ¹H NMR (Methanol-d₄, 400 MHz) δ 7.89 (d, 1H), 7.82-7.76 (m, 1H), 7.72-7.64 (m, 2H), 6.26 (s, 1H), 5.14 (s, 1H), 5.06 (s, 2H), 4.01-3.90 (m, 3H), 3.27-3.17 (m, 2H), 2.83-2.70 (m, 2H); LCMS (ESI): m/z 384.0 (M+H).

Example 94

Synthesis of Compound 94

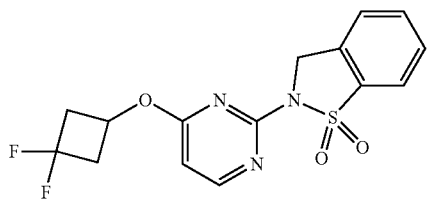 [SMILES: O=S1(=O)c2ccccc2CN1c1nccc(OC2CC(F)(F)C2)n1]

Compound 94 was synthesized in a manner similar to Compound 77. ¹H NMR (DMSO-d₆, 400 MHz) δ 8.39-8.38 (d, 1H), 7.92-7.90 (d, 1H), 7.83-7.79 (t, 1H), 7.72-7.69 (m, 2H), 6.62-6.61 (d, 1H), 6.41-6.20 (m, 1H), 5.15 (s, 2H), 3.28-3.21 (m, 2H), 2.84-2.77 (m, 2H); LCMS (ESI): m/z 354.0 (M+H).

Example 95

Synthesis of Compound 95

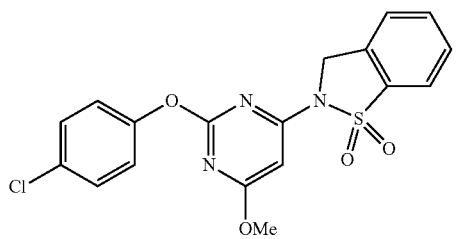 [SMILES: COc1cc(N2Cc3ccccc3S2(=O)=O)nc(Oc2ccc(Cl)cc2)n1]

Compound 95 was synthesized in a manner similar to Compound 77. ¹H NMR (DMSO-d₆ 400 MHz) δ 8.03 (d, J=7.78 Hz, 1H), 7.90-7.80 (m, 1H), 7.77-7.66 (m, 2H), 7.50 (d, J=8.78 Hz, 2H), 7.41-7.30 (m, 2H), 6.41-6.20 (m, 1H), 5.10 (s, 2H), 3.84 (s, 3H); LCMS (ESI): m/z 404.0 (M+H).

Example 96

Synthesis of Compound 96

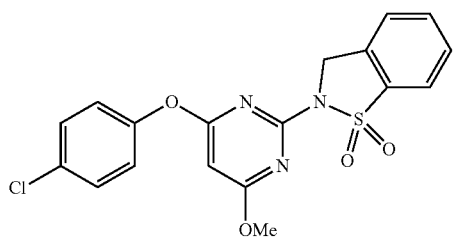 [SMILES: COc1cc(Oc2ccc(Cl)cc2)nc(N2Cc3ccccc3S2(=O)=O)n1]

Compound 96 was synthesized in a manner similar to Compound 77 ¹H NMR (DMSO-d₆, 400 MHz) δ 7.97 (d, J=7.78 Hz, 1H), 7.87-7.78 (m, 1H), 7.76-7.71 (m, 1H), 3.99 (s, 3H), 7.70-7.62 (m, 1H), 7.52 (d, J=8.78 Hz, 2H), 7.36 (d, J=8.78 Hz, 2H), 6.04 (s, 1H), 5.05 (s, 2H); LCMS (ESI): m/z 404.0 (M+H).

Example 97

Synthesis of Compound 97

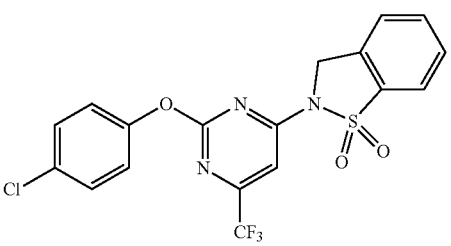 [SMILES: O=S1(=O)c2ccccc2CN1c1cc(C(F)(F)F)nc(Oc2ccc(Cl)cc2)n1]

Compound 97 was synthesized in a manner similar to Compound 77. ¹H NMR (DMSO-d₆, 400 MHz) δ 8.10 (d, 1H), 7.90-7.84 (m, 1H), 7.77-7.69 (m, 2H), 7.53 (d, 2H), 7.40 (d, 2H), 7.34 (s, 1H), 5.26 (s, 2H); LCMS (ESI): m/z 442.1 (M+H).

Example 98

Synthesis of Compound 98

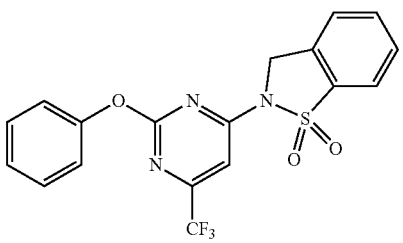 [SMILES: O=S1(=O)c2ccccc2CN1c1cc(C(F)(F)F)nc(Oc2ccccc2)n1]

Compound 98 was synthesized in a manner similar to Compound 77. ¹H NMR (DMSO-d₆, 400 MHz) δ 8.09 (d, 1H), 7.89-7.84 (m, 1H), 7.76-7.71 (m, 2H), 7.50-7.45 (m, 2H), 7.35-7.30 (m, 4H), 5.26 (s, 2H); LCMS (ESI): m/z 408.0 (M+H).

Example 99

Synthesis of Compound 99

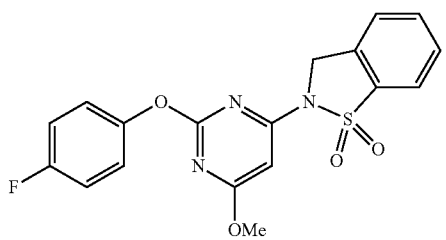 [SMILES: COc1cc(N2Cc3ccccc3S2(=O)=O)nc(Oc2ccc(F)cc2)n1]

Compound 99 was synthesized in a manner similar to Compound 77. ¹H NMR (DMSO-d$_6$, 400 MHz) δ 8.03 (d, J=7.78 Hz, 1H), 7.89-7.80 (m, 1H), 7.75-7.57 (m, 2H), 7.37 (dd, J=8.91, 4.64 Hz, 2H), 7.32-7.21 (m, 2H), 5.09 (s, 2H), 6.31 (s, 1H), 3.90-3.73 (m, 3H); LCMS (ESI): m/z 388.0 (M+H).

Example 100

Synthesis of Compound 100

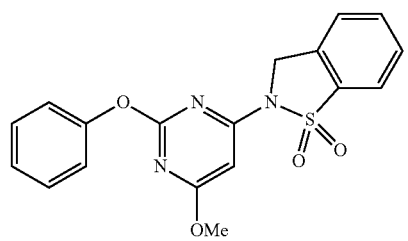 [SMILES: COc1cc(N2Cc3ccccc3S2(=O)=O)nc(Oc2ccccc2)n1]

Compound 100 was synthesized in a manner similar to Compound 77. NMR (DMSO-d$_6$, 400 MHz) δ 8.02 (d, 1H), 7.85-7.80 (m, 1H), 7.70 (d, 2H), 7.47-7.42 (m, 2H), 7.33-7.25 (m, 3H), 6.30 (s, 1H), 5.08 (s, 2H), 3.81 (s, 3H); LCMS (ESI): m/z 370.0 (M+H).

Example 101

Synthesis of Compound 101

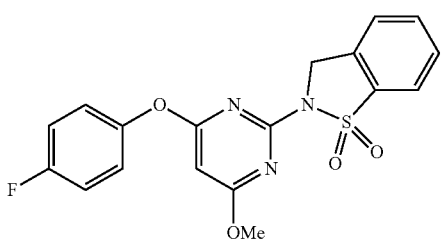

Compound 101 was synthesized in a manner similar to Compound 77. NMR (DMSO-d$_6$, 400 MHz) δ 7.97 (d, J=7.78 Hz, 1H), 7.86-7.77 (m, 1H), 7.75-7.71 (m, 1H), 7.70-7.62 (m, 1H), 7.40-7.25 (m, 4H), 5.95 (s, 1H), 5.11-4.97 (m, 2H), 3.98 (s, 3H); LCMS (ESI): m/z 388.0 (M+H).

Example 102

Synthesis of Compound 102

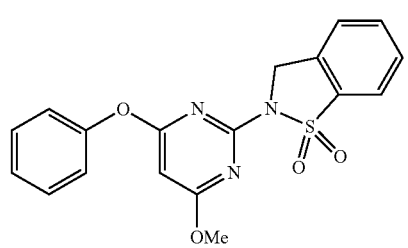 [SMILES: COc1cc(Oc2ccccc2)nc(N2Cc3ccccc3S2(=O)=O)n1]

Compound 102 was synthesized in a manner similar to Compound 77. ¹H NMR (DMSO-d$_6$, 400 MHz) δ 7.96 (d, 1H), 7.82-7.76 (m, 1H), 7.73-7.64 (m, 2H), 7.50-7.45 (m, 2H), 7.33-7.28 (m, 3H), 5.86 (s, 1H), 5.05 (s, 2H), 3.96 (s, 3H); LCMS (ESI): m/z 370.1 (M+H).

Example 103

Synthesis of Compound 103

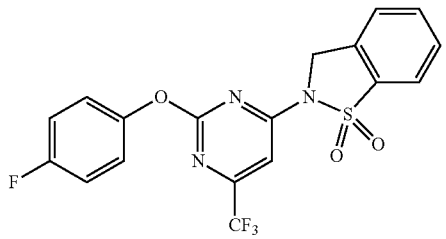 [SMILES: O=S1(=O)c2ccccc2CN1c1cc(C(F)(F)F)nc(Oc2ccc(F)cc2)n1]

Compound 103 was synthesized in a manner similar to Compound 77. ¹H NMR (DMSO-d$_6$, 400 MHz) δ 8.09 (d, 1H), 7.89-7.84 (m, 1H), 7.76-7.70 (m, 2H), 7.41-7.37 (m, 2H), 7.34-7.31 (m, 2H), 7.30-7.27 (m, 1H), 5.25 (s, 2H); LCMS (ESI): m/z 426.0 (M+H).

Example 104

Synthesis of Compound 104

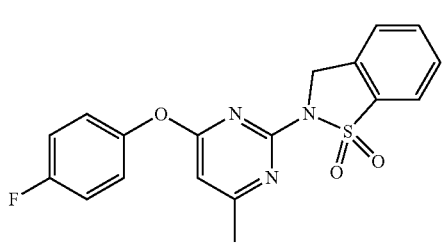 [SMILES: Cc1cc(Oc2ccc(F)cc2)nc(N2Cc3ccccc3S2(=O)=O)n1]

Compound 104 was synthesized in a manner similar to Compound 77. ¹H NMR (DMSO-d$_6$, 400 MHz) δ 7.95 (d, 1H), 7.81-7.76 (m, 1H), 7.73-7.74 (m, 1H), 7.68-7.63 (m, 1H), 7.40-7.35 (m, 2H), 7.33-7.27 (m, 2H), 6.58 (s, 1H), 5.04 (s, 2H), 2.42 (s, 3H); LCMS (ESI): m/z 372.1 (M+H).

Example 105

Synthesis of Compound 105

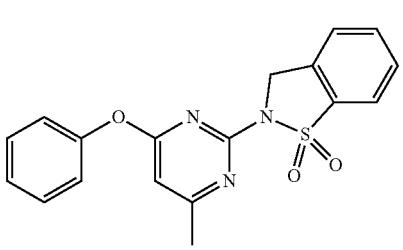 [SMILES: Cc1cc(Oc2ccccc2)nc(N2Cc3ccccc3S2(=O)=O)n1]

Compound 105 was synthesized in a manner similar to Compound 77. ¹H NMR (DMSO-d₆, 400 MHz) δ 7.95 (d, 1H), 7.82-7.76 (m, 1H), 7.73-7.64 (m, 2H), 7.51-7.46 (m, 2H), 7.35-7.30 (m, 3H), 6.51 (s, 1H), 5.05 (s, 2H), 2.41 (s, 3H); LCMS (ESI): m/z 354.0 (M+H).

Example 106

Synthesis of Compound 106

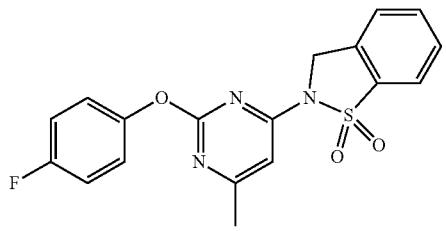 [SMILES: Cc1cc(N2Cc3ccccc3S2(=O)=O)nc(Oc2ccc(F)cc2)n1]

Compound 106 was synthesized in a manner similar to Compound 77. ¹H NMR (DMSO-d₆, 400 MHz) δ 8.05 (d, 1H), 7.87-7.81 (m, 1H), 7.75-7.68 (m, 2H), 7.33-7.21 (m, 4H), 6.94 (s, 1H), 5.13 (s, 2H), 2.36 (s, 3H); LCMS (ESI): m/z 372.1 (M+H).

Example 107

Synthesis of Compound 107

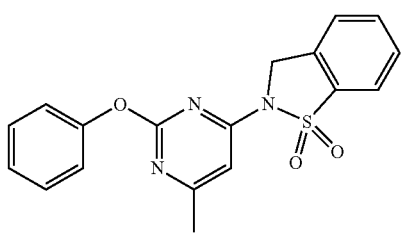 [SMILES: Cc1cc(N2Cc3ccccc3S2(=O)=O)nc(Oc2ccccc2)n1]

Compound 107 was synthesized in a manner similar to Compound 77. ¹H NMR (DMSO-d₆, 400 MHz) δ 8.05 (d, 1H), 7.87-7.81 (m, 1H), 7.75-7.67 (m, 2H), 7.47-7.41 (m, 2H), 7.28-7.23 (m, 3H), 6.95 (s, 1H), 5.14 (s, 2H), 2.36 (s, 3H); LCMS (ESI): m/z 354.0 (M+H).

Example 108

Synthesis of Compound 108

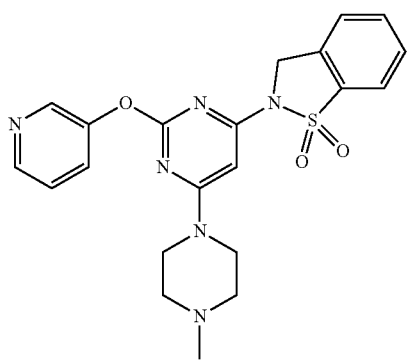 [SMILES: CN1CCN(c2cc(N3Cc4ccccc4S3(=O)=O)nc(Oc3cccnc3)n2)CC1]

Compound 108 was synthesized in a manner similar to Compound 77. ¹H NMR (DMSO-d₆, 400 MHz) δ 8.53 (s, 1H), 8.45 (d, 1H), 7.89 (d, 1H), 7.76 (t, 2H), 7.70-7.59 (m, 2H), 7.47 (dd, 1H), 6.12 (s, 1H), 4.92 (s, 2H), 3.67 (s, 4H), 2.33 (s, 4H), 2.26 (s, 3H); LCMS (ESI): m/z 439.1 (M+H).

Example 109

Synthesis of Compound 109

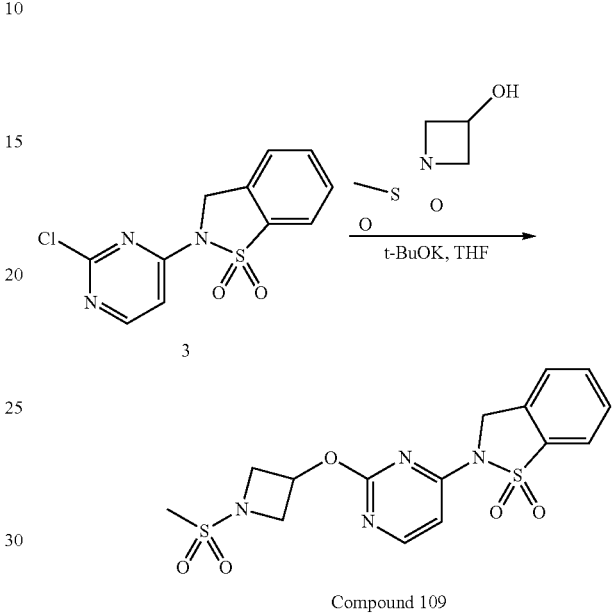

Compound 109

To a solution of 3 (120 mg, 0.43 mmol) and 1-methylsulfonylazetidin-3-ol (77 mg, 0.51 mmol) in THF (2 mL) was added t-BuOK (96 mg, 0.85 mmol) at 0° C. The resulting mixture was stirred at 0° C. for 2 hours. Upon completion, the reaction mixture was quenched by addition NH₄Cl (5 mL) at 0° C. and then extracted with EtOAc (10 mL). The combined organic layers were washed with brine (10 mL), dried over Na₂SO₄, filtered and concentrated under reduced pressure. Purification by HPLC (0.04% HCl/CH₃CN/H₂O system) resulted in Compound 109 (13 mg, 7%) as a white solid. ¹H NMR (DMSO-d₆, 400 MHz) δ 8.53-8.46 (m, 1H), 8.05 (d, J=7.94 Hz, 1H), 7.91-7.82 (m, 1H), 7.77-7.52 (m, 2H), 7.03-6.86 (m, 1H), 5.40-5.25 (m, 1H), 5.23-5.13 (m, 2H), 4.32 (dd, J=9.48, 6.84 Hz, 2H), 4.09-3.96 (m, 2H), 3.06 (s, 3H); LCMS (ESI): m/z 397.0 (M+H).

Example 110

Synthesis of Compound 110

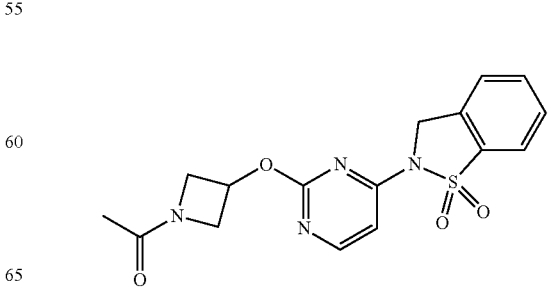

Compound 110 was synthesized in a manner similar to Compound 109. ¹H NMR (Methanol-d₄, 400 MHz) δ 8.45 (d, J=5.77 Hz, 1H), 7.94 (d, J=7.78 Hz, 1H), 7.88-7.81 (m, 1H), 7.75-7.66 (m, 2H), 7.06 (d, J=5.77 Hz, 1H), 5.47 (bs, 1H), 5.17 (s, 2H), 4.75 (t, J=8.28 Hz, 1H), 4.55-4.45 (m, 1H), 4.33 (d, J=7.53 Hz, 1H), 4.07 (d, J=10.54 Hz, 1H), 1.94 (s, 3H); LCMS (ESI): m/z 361.0 (M+H).

Example 111

Synthesis of Compound 111

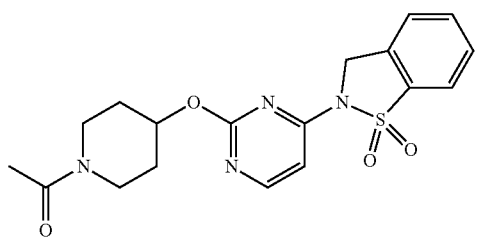 [SMILES: CC(=O)N1CCC(Oc2nccc(N3Cc4ccccc4S3(=O)=O)n2)CC1]

Compound 111 was synthesized in a manner similar to Compound 109. ¹H NMR: (Methanol-d₄, 400 MHz) δ 8.33 (d, J=5.73 Hz, 1H), 7.87 (d, J=7.94 Hz, 1H), 7.82-7.75 (m, 1H), 7.71-7.62 (m, 2H), 6.54 (d, J=5.73 Hz, 1H), 5.43 (dt, J=8.05, 4.13 Hz, 1H), 5.13 (s, 2H), 4.08-3.97 (m, 1H), 3.83 (d, J=13.67 Hz, 1H), 3.58-3.39 (m, 2H), 2.30-2.05 (m, 5H), 1.95-1.62 (m, 1H); LCMS (ESI): m/z 389.1 (M+H).

Example 112

Synthesis of Compound 112

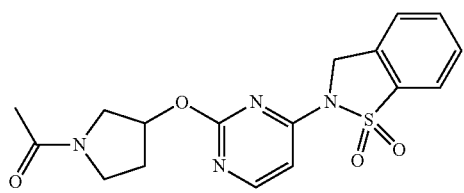 [SMILES: CC(=O)N1CCC(Oc2nccc(N3Cc4ccccc4S3(=O)=O)n2)C1]

Compound 112 was synthesized in a manner similar to Compound 109. ¹H NMR: (Methanol-d₄, 400 MHz) δ 8.42 (t, J=5.29 Hz, 1H), 8.02-7.79 (m, 2H), 7.74-7.63 (m, 2H), 7.04 (dd, J=16.32, 5.73 Hz, 1H), 5.67 (bs, 1H), 5.24-5.11 (m, 2H), 4.02 (dd, J=12.35, 4.41 Hz, 1H), 3.84-3.44 (m, 4H), 2.47-2.25 (m, 2H), 2.14-2.01 (m, 3H); LCMS (ESI): m/z 375.1 (M+H).

Example 113

Synthesis of Compound 113

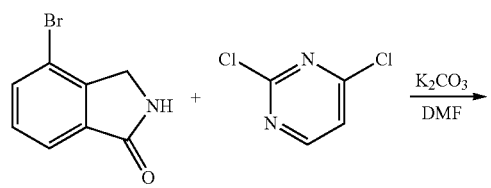

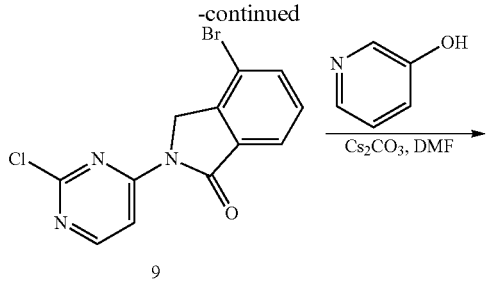

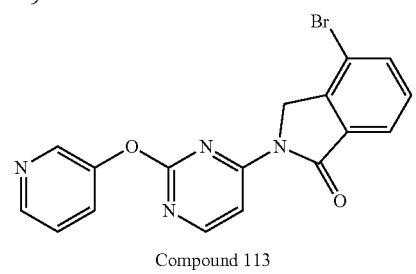

Compound 113

Step 1.

A mixture of 2,4-dichloropyrimidine (116 mg, 0.78 mmol), 4-bromoisoindolin-1-one (150 mg, 0.71 mmol), K₂CO₃ (196 mg, 1.41 mmol) in DMF (3 mL) was degassed and purged with N₂ three times, and then the mixture was stirred at 80° C. for 14 hours under an inert atmosphere. The resulting mixture was filtered and concentrated under reduced pressure. Purification by prep-TLC (SiO₂, petroleum ether/ethyl acetate=3:1) provided 9 (80 mg) as a light yellow solid which was used directly in the next step without further purification.

Step 2.

A mixture of 9 (80 mg, 0.13 mmol), pyridin-3-ol (14.6 mg, 0.15 mmol) and Cs₂CO₃ (83 mg, 0.26 mmol) in DMF (3 mL) was degassed and purged with N₂ three times, and then the mixture was stirred at 50° C. for 1 hour under an inert atmosphere. The reaction mixture was filtered, and then diluted with water (20 mL) and extracted with ethyl acetate (3×20 mL). The combined organic layers were washed with water (3×15 mL) and saturated brine (2×20 mL), dried over anhydrous Na₂SO₄, filtered, and concentrated under reduced pressure to give a residue which was purified by prep-HPLC (HCl, 0.05% HCl-ACN) to afford (13.9 mg, 28%) of Compound 113 as an orange solid. ¹H NMR (DMSO-d₆, 400 MHz) δ 8.89 (s, 1H), 8.69-8.68 (d, 1H), 8.60-8.58 (d, 1H), 8.26-8.24 (m, 2H), 8.00-7.98 (d, 1H), 7.90-7.85 (m, 2H), 7.58-7.54 (m, 1H), 4.88 (s, 2H); LCMS (ESI): m/z 383.0 (M+H).

Example 114

Synthesis of Compound 114

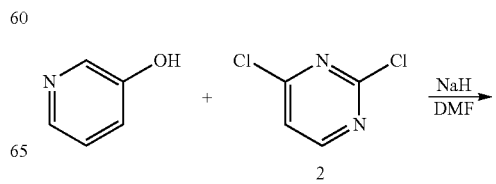

-continued

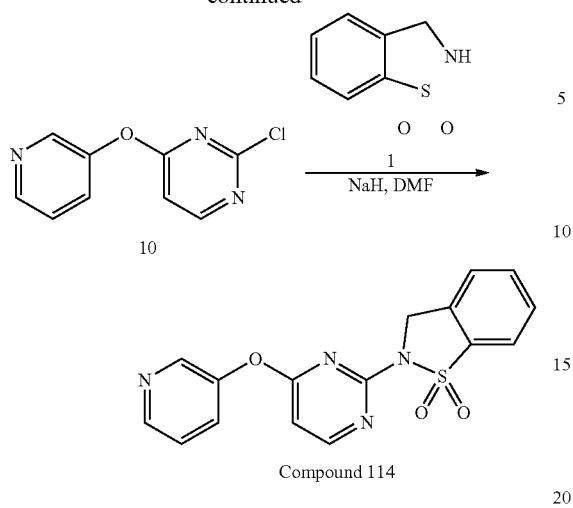

Compound 114

-continued

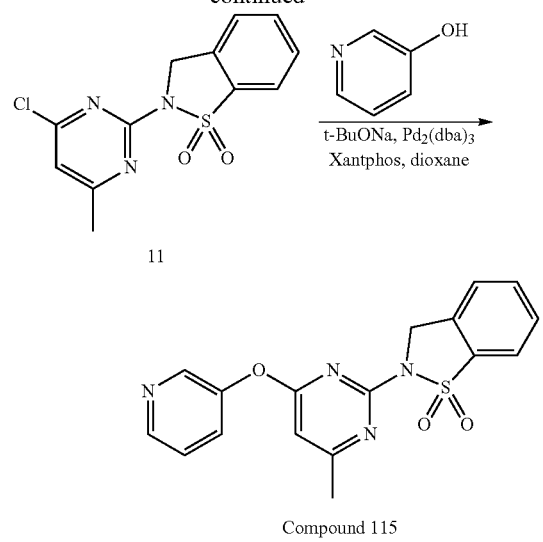

Compound 115

Step 1.

A solution of 3-hydroxypyridine (3.06 g, 32.2 mmol) in DMF (100 mL) was cooled to 0° C., and NaH (773 mg, 32.22 mmol) was added. The mixture was stirred at 0° C. for 30 minutes, warmed to 15° C., and then 2 (4.0 g, 26.9 mmol) was added. The reaction mixture was allowed to stir for another 3 hours. Upon completion, water (100 mL) was added and the resulting mixture was extracted with EtOAc (90 mL). The organic layer was dried over sodium sulfate, filtered, concentrated to give a residue. Purification by silica-gel chromatography (petroleum ether:EtOAc=50:1 to 20:1) resulted in 10 (2.2 g, 37%).

Step 2.

Solution of 1 (97 mg, 0.053 mmol) in DMF (4 mL) was cooled to 0° C. and NaH (13.9 mg, 0.058 mmol) was added. The mixture was stirred at 0° C. for 30 minutes followed by addition of 10 (100 mg, 0.48 mmol). The solution was allowed to stir 15 hours at 0° C. The resulting mixture was poured into water (20 mL) and stirred for 10 minutes. The aqueous phase was extracted with ethyl acetate (30 mL). The combined organic layer was washed with brine (20 mL), dried with anhydrous sodium sulfate, filtered, and concentrated. Purification with prep-HPLC (0.04% $NH_3 \cdot H_2O$/ACN/$H_2O$ system) resulted in Compound 114 (20 mg) as a white solid. $^1$H NMR (DMSO-$d_6$, 400 MHz) δ 8.56 (d, 1H), 8.51-8.46 (m, 2H), 8.06 (d, 1H), 7.88-7.82 (m, 1H), 7.81-7.67 (m, 3H), 7.50 (dd, 8.2 Hz, 1H), 7.09 (d, 1H), 5.17 (s, 2H); LCMS (ESI+): m/z 341 (M+H).

Example 115

Synthesis of Compound 115

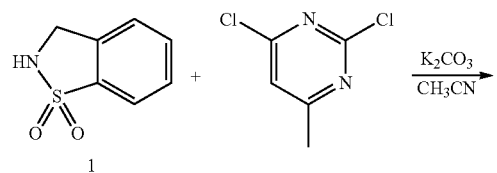

Step 1.

To a mixture of 6-methyl-2,4-dichloropyrimidine (162 mg, 0.994 mmol) and 1 (185 mg, 1.1 mmol) in anhydrous $CH_3CN$ (4 mL) was added $K_2CO_3$ (274 mg, 2 mmol), the mixture was stirred at 80° C. for 3 hrs. Concentration under reduced pressure resulted in 11 (130 mg), which was submitted to the next step without further purification.

Step 2.

To a solution of 11 (130 mg crude material), pyridin-3-ol (26 mg, 0.28 mmol), t-BuONa (45 mg, 0.47 mmol) and Xantphos (13.5 mg, 0.023 mmol) in anhydrous dioxane (3 mL) was added $Pd_2(dba)_3$ (21 mg, 0.023 mmol). The mixture was stirred at 100° C. for 12 hours under inert atmosphere, filtered, and then concentrated under reduced pressure. Purification with prep-HPLC (0.04% HCl/$CH_3CN$/$H_2O$ system) resulted in Compound 115 (3.6 mg, 2.1%) as an HCl salt. $^1$H NMR (DMSO-$d_6$, 400 MHz) δ 8.74 (s, 1H), 8.60 (d, 1H), 7.93 (d, 1H), 7.77 (d, 1H), 7.71-7.65 (m, 4H), 6.79 (m, 1H), 5.03 (s, 2H), 2.46 (s, 3H); LCMS (ESI): m/z 355.0 (M+H).

Example 116

Synthesis of Compound 116

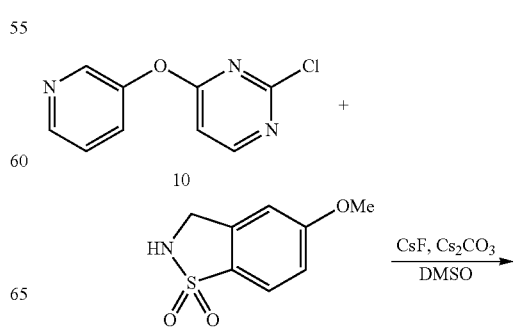

83
-continued

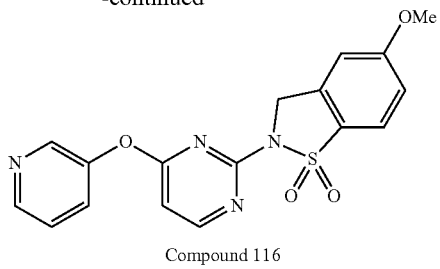

Compound 116

To a mixture of 10 (123 mg, 0.59 mmol), 2,3-dihydro-5-methoxy-1,1-dioxo-1,2-benzisothiazole (96 mg, 0.48 mmol), and CsF (146 mg, 0.96 mmol) in anhydrous DMSO (2 mL) was added cesium carbonate (314 mg, 0.96 mmol). The resulting mixture was degassed and stirred at 80° C. for 3 hours under inert atmosphere. Upon completion, the mixture was filtered. Purification by prep-HPLC (0.04% HCl/CH$_3$CN/H$_2$O system) resulted in Compound 116 (3.5 mg, 1.4%) as the HCl salt. $^1$H NMR (Methanol-d$_4$, 400 MHz) δ 9.08 (s, 1H), 8.74 (d, 1H), 8.53 (d, 1H), 8.10-8.07 (q, 1H), 7.77 (d, 1H), 7.23-7.14 (m, 3H), 5.03 (s, 2H), 3.93 (s, 3H); LCMS (ESI): m/z 371.0 (M+H).

Example 117

Synthesis of Compound 117

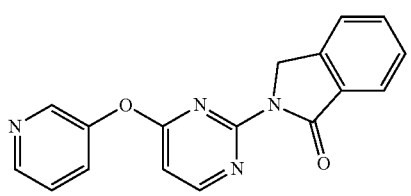 [SMILES: O=C1c2ccccc2CN1c1nccc(Oc2cccnc2)n1]

Compound 117 was synthesized in a manner similar to Compound 116. $^1$H NMR (DMSO-d$_6$, 400 MHz) δ 8.81 (s, 1H), 8.65-8.63 (d, 1H), 8.57-8.56 (d, 1H), 8.29-8.28 (d, 1H), 8.14-8.13 (d, 1H), 7.87-7.85 (d, 1H), 7.78-7.72 (m, 3H), 7.60-7.58 (m, 1H), 4.98 (s, 2H); LCMS (ESI): m/z 305.1 (M+H).

Example 118

Synthesis of Compound 118

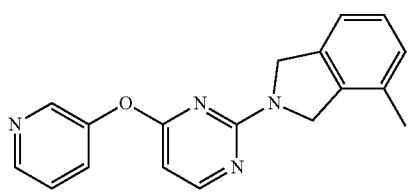 [SMILES: Cc1cccc2c1CN(c1nccc(Oc3cccnc3)n1)C2]

Compound 118 was synthesized in a manner similar to Compound 116. $^1$H NMR (DMSO-d$_6$, 400 MHz) δ 8.86 (s, 1H), 8.68-8.67 (d, 1H), 8.43-8.41 (d, 1H), 8.20-8.18 (t, 1H), 7.83-7.81 (t, 1H), 7.18-7.07 (m, 3H), 6.58-6.55 (m, 1H), 4.85-4.80 (d, 2H), 4.54 (s, 1H), 2.25-2.16 (d, 3H); LCMS (ESI): m/z 305.1 (M+H).

84

Example 119

Synthesis of Compound 119

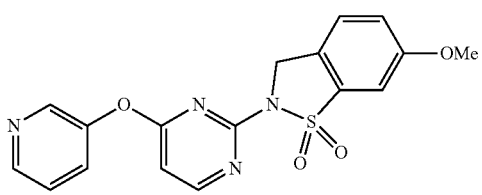 [SMILES: COc1ccc2c(c1)S(=O)(=O)N(c1nccc(Oc3cccnc3)n1)C2]

Compound 119 was synthesized in a manner similar to Compound 116. $^1$H NMR (Methanol-d$_4$, 400 MHz) δ 9.08 (s, 1H), 8.74 (d, 1H), 8.53 (d, 1H), 8.10-8.07 (q, 1H), 7.77 (d, 1H), 7.23-7.14 (m, 3H), 5.03 (s, 2H), 3.93 (s, 3H); LCMS (ESI): m/z 371.0 (M+H).

Example 120

Synthesis of Compound 120

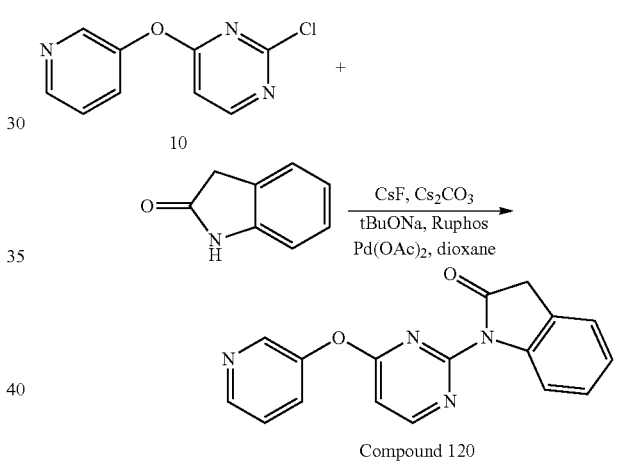

Compound 120

A mixture of 10 (150 mg, 0.72 mmol), 2-oxindole (125 mg, 0.94 mmol), tBuONa (139 mg, 1.44 mmol), Ruphos (67 mg, 0.144 mmol) and Pd(OAc)$_2$ (32 mg, 0.144 mmol) in dioxane (2 mL) was degassed and stirred at 100° C. for 12 hours under an inert atmosphere. Upon completion, the mixture was filtered and concentrated under reduced pressure. Purification by prep-HPLC (0.04% HCl/CH$_3$CN/H$_2$O system) resulted in Compound 120 (1 mg) as a yellow oil. $^1$H NMR (DMSO-d$_6$, 400 MHz) δ 8.68 (s, 2H), 8.25 (d, 1H), 7.93 (d, 1H), 7.69-7.66 (m, 1H), 6.79-6.75 (m, 2H), 6.64 (d, 1H), 6.53 (d, 1H), 6.51 (d, 1H), 6.45 (d, 1H), 3.50 (s, 2H); LCMS (ESI): m/z 305.1 (M+H).

Example 121

Synthesis of Compound 121

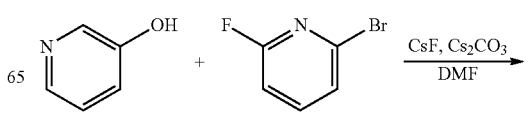

85

-continued

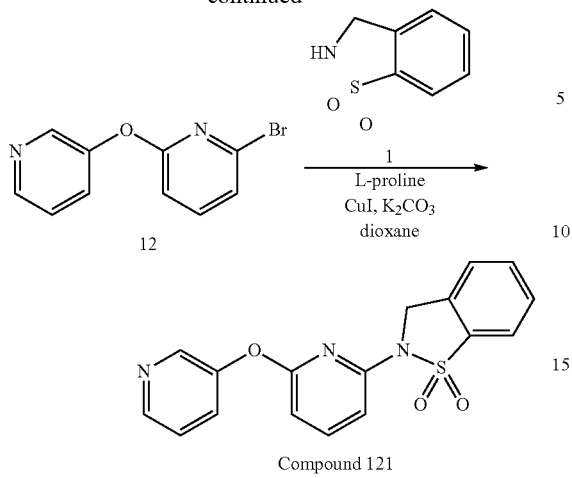

Compound 121

Step 1.
A mixture of 2-bromo-6-fluoropyridine (500 mg, 2.84 mmol), pyridin-3-ol (297 mg, 3.13 mmol), cesium carbonate (1.85 g, 5.68 mmol) and CsF (22 mg, 142 mmol) in DMF (5 mL) was stirred at 120° C. for 2 hours. Upon completion, water (40 mL) was added and the reaction mixture was extracted with EtOAc (90 mL). The organic phase was washed with brine (50 mL), dried with anhydrous MgSO$_4$, filtered, and concentrated under reduced pressure to give 12 (700 mg).

Step 2.
A mixture of 12 (100 mg, 0.40 mmol), 1 (67 mg, 0.40 mmol), potassium carbonate (55 mg, 0.40 mmol), CuI (3.8 mg, 0.019 mmol), and L-proline (2.3 mg, 0.019 mmol) in dioxane (4 mL) was stirred at 110° C. for 16 hours under an inert atmosphere. Upon completion, water (40 mL) was added and the reaction mixture was extracted with EtOAc (90 mL). The organic phase was washed with brine (50 mL) and concentrated under reduced pressure. Purification with prep-HPLC (0.075% TFA/CH$_3$CN/H$_2$O system) resulted in Compound 121 (40 mg, 29%) as yellow solid and TFA salt. $^1$H NMR (DMSO-d$_6$, 400 MHz) δ 8.69-8.68 (d, 1H), 8.53-8.52 (d, 1H), 7.99-7.94 (m, 3H), 7.77 (m, 1H), 7.67-7.62 (m, 3H), 7.07-7.05 (d, 1H), 6.83-6.81 (d, 1H), 4.95 (s, 2H); LCMS (ESI): m/z 340.1 (M+H).

Example 122

Synthesis of Compound 122

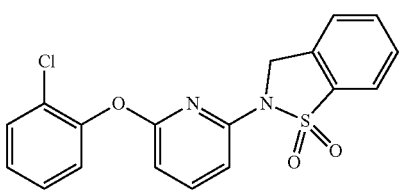 [SMILES: O=S1(=O)c2ccccc2CN1c1cccc(Oc2ccccc2Cl)n1]

Compound 122 was synthesized in a manner similar to Compound 121. $^1$H NMR (DMSO-d$_6$, 400 MHz) δ 8.84 (s, 1H), 8.33-8.31 (d, 1H), 8.04-8.00 (t, 1H), 7.82-7.80 (m, 1H), 7.68-7.64 (m, 1H), 7.56-7.54 (d, 2H), 6.94-6.93 (d, 1H), 4.80 (s, 2H); LCMS (ESI): m/z 304.0 (M+H).

86

Example 123

Synthesis of Compound 123

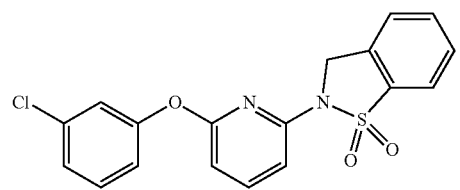

Compound 123 was synthesized in a manner similar to Compound 121. $^1$H NMR (Methanol-d$_4$, 400 MHz) δ 8.20 (s, 1H), 7.90-7.88 (d, 1H), 7.79-7.77 (t, 1H), 7.71-7.67 (m, 2H), 7.58-7.55 (m, 2H), 7.38-7.35 (t, 1H), 7.16-7.15 (d, 1H), 7.04 (s, 1H), 5.15 (s, 2H); LCMS (ESI): m/z 373.0 (M+H).

Example 124

Synthesis of Compound 124

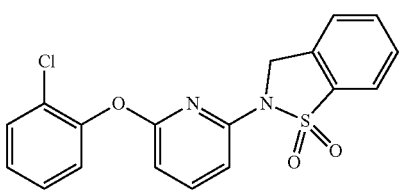 [SMILES: O=S1(=O)c2ccccc2CN1c1cccc(Oc2ccccc2Cl)n1]

Compound 124 was synthesized in a manner similar to Compound 121. $^1$HNMR (DMSO-d$_6$, 400 MHz) δ 8.26-8.25 (d, 1H), 8.02-8.00 (d, 1H), 7.83-7.71 (m, 1H), 7.69-7.61 (m, 4H), 7.43-7.40 (m, 2H), 7.42-7.38 (d, 1H), 7.13-7.11 (d, 1H), 5.17 (s, 2H); LCMS (ESI): m/z 373.0 (M+H).

Example 125

Synthesis of Compound 125

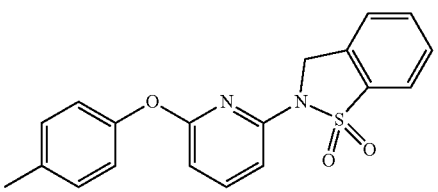 [SMILES: Cc1ccc(Oc2cccc(N3Cc4ccccc4S3(=O)=O)n2)cc1]

Compound 125 was synthesized in a manner similar to Compound 121. $^1$HNMR (DMSO-d$_6$, 400 MHz) δ 8.30 (d, 1H), 7.90 (d, 1H), 7.74 (d, 1H), 7.71-7.69 (m, 3H), 7.45-7.43 (m, 3H), 7.09-7.06 (m, 2H), 5.17 (s, 2H); LCMS (ESI): m/z 373.0 (M+H).

Example 126

Synthesis of Compound 126

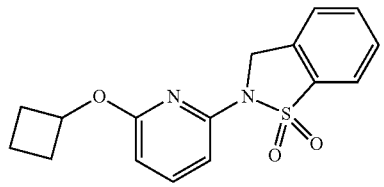 [SMILES: O=S1(=O)c2ccccc2CN1c1cccc(OC2CCC2)n1]

Compound 126 was synthesized in a manner similar to Compound 121. ¹H NMR (Methanol-$d_4$, 400 MHz) δ 7.99-7.98 (d, 1H), 7.87-7.85 (d, 1H), 7.77-7.75 (d, 1H), 7.68-7.65 (m, 2H), 7.42 (m, 1H), 7.38-7.37 (m, 1H), 5.08 (s, 2H), 4.76-4.69 (m, 1H), 2.49-2.47 (m, 2H), 2.17-2.12 (m, 2H), 1.75-1.88 (m, 2H); LCMS (ESI): m/z 317.0 (M+H).

Example 127

Synthesis of Compound 127

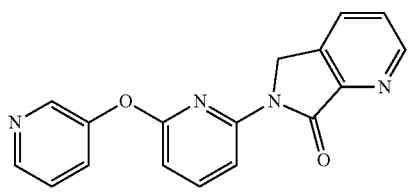

Compound 127 was synthesized in a manner similar to Compound 121. ¹H NMR (Methanol-$d_4$, 400 MHz) δ 9.06 (bs, 1H), 8.90 (d, J=7.94 Hz, 1H), 8.83 (d, J=2.65 Hz, 1H), 8.75 (d, J=9.26 Hz, 1H), 8.69 (d, J=5.29 Hz, 1H), 8.51 (d, J=2.65 Hz, 1H), 8.36 (dd, J=8.82, 1.76 Hz, 1H), 5.44 (s, 2H), 8.27 (dd, J=7.94, 5.73 Hz, 1H), 8.13 (dd, J=8.82, 5.29 Hz, 1H), 7.92 (dd, J=9.04, 2.87 Hz, 1H); LCMS (ESI): m/z 305.0 (M+H).

Example 128

Synthesis of Compound 128

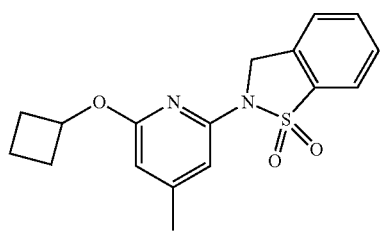 [SMILES: Cc1cc(OC2CCC2)nc(N2Cc3ccccc3S2(=O)=O)c1]

Compound 128 was synthesized in a manner similar to Compound 121. ¹H NMR (Methanol-$d_4$, 400 MHz) δ 7.86-7.84 (d, 1H), 7.78-7.74 (m, 1H), 7.69-7.63 (m, 2H), 6.73 (s, 1H), 6.29 (s, 1H), 5.22-5.15 (m, 1H), 5.05 (s, 2H), 2.54-2.52 (m, 2H), 2.32 (s, 3H), 2.14-2.09 (m, 2H), 1.85-1.71 (m, 2H); LCMS (ESI): m/z 331.1 (M+H).

Example 129

Synthesis of Compound 129

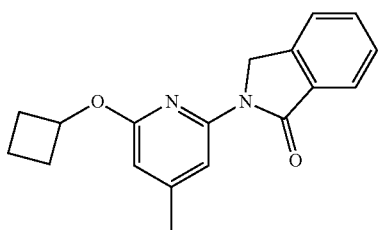 [SMILES: Cc1cc(OC2CCC2)nc(N2Cc3ccccc3C2=O)c1]

Compound 129 was synthesized in a manner similar to Compound 121. ¹H NMR (Methanol-$d_4$, 400 MHz) δ 8.41-8.39 (d, 1H), 8.02-8.01 (d, 1H), 7.87-7.85 (d, 1H), 7.69-7.65 (m, 2H), 7.55-7.53 (m, 1H), 7.43-7.40 (m, 1H), 5.10 (s, 2H), 4.79-4.75 (m, 1H), 2.52-2.49 (m, 2H), 2.19-2.14 (m, 2H), 1.90-1.72 (m, 2H); LCMS (ESI): m/z 281.1 (M+H).

Example 130

Synthesis of Compound 130

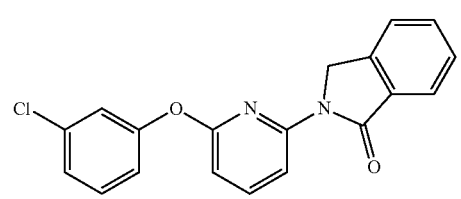 [SMILES: O=C1c2ccccc2CN1c1cccc(Oc2cccc(Cl)c2)n1]

Compound 130 was synthesized in a manner similar to Compound 121. ¹H NMR (Methanol-$d_4$, 400 MHz) δ 8.64-8.61 (d, 1H), 8.23-8.22 (d, 1H), 7.88-7.86 (d, 1H), 7.70-7.68 (m, 2H), 7.61-7.57 (m, 2H), 7.36-7.34 (m, 1H), 7.17-7.15 (m, 1H), 7.06 (s, 1H), 6.98-6.96 (d, 1H), 5.16 (s, 2H); LCMS (ESI): m/z 337.0 (M+H).

Example 131

Synthesis of Compound 131

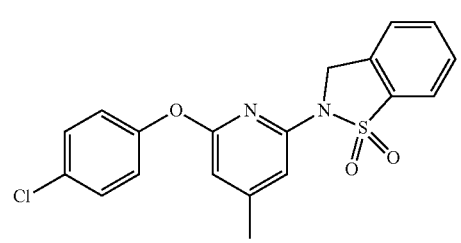 [SMILES: Cc1cc(Oc2ccc(Cl)cc2)nc(N2Cc3ccccc3S2(=O)=O)c1]

Compound 131 was synthesized in a manner similar to Compound 121. ¹H NMR (Methanol-$d_4$, 400 MHz) δ 7.86-7.84 (d, 1H), 7.75-7.73 (m, 1H), 7.64-7.60 (m, 2H), 7.41-7.38 (m, 2H), 7.20-7.17 (m, 2H), 7.04 (s, 1H), 6.54 (s, 1H), 4.87 (s, 2H), 2.40 (s, 3H); LCMS (ESI): m/z 387.0 (M+H).

Example 132

Synthesis of Compound 132

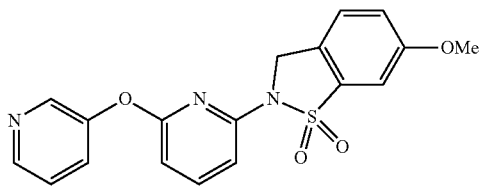

Compound 132 was synthesized in a manner similar to Compound 121. $^1$H NMR (DMSO-$d_6$, 400 MHz) 8.70 (s, 1H), 8.58 (d, J=4.85 Hz, 1H), 8.37 (d, J=2.65 Hz, 1H), 8.20-8.12 (m, 1H), 7.98 (dd, J=8.82, 5.29 Hz, 1H), 7.78 (dd, J=9.04, 2.87 Hz, 1H), 7.63-7.53 (m, 2=H), 7.41 (d, J=2.65 Hz, 1H), 7.36 (dd, J=8.60, 2.43 Hz, 1H), 5.08 (s, 2H). 3.92 (s, 1H); LCMS (ESI): m/z 370.0 (M+H).

Example 133

Synthesis of Compound 133

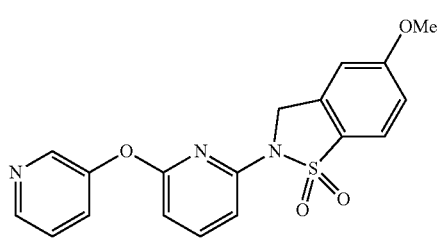 [SMILES: COc1ccc2c(c1)CN(c1cccc(Oc3cccnc3)n1)S2(=O)=O]

Compound 133 was synthesized in a manner similar to Compound 121. $^1$H NMR (DMSO-$d_6$, 400 MHz) δ 8.45-8.33 (m, 3H), 7.94-7.92 (d, 1H), 7.77-7.74 (dd, 1H), 7.49-7.45 (m, 3H), 7.42 (s, 2H), 7.28-7.22 (dd, 1H), 5.11 (s, 1H), 3.90 (s, 3H); LCMS (ESI): m/z 370.0 (M+H).

Example 134

Synthesis of Compound 134

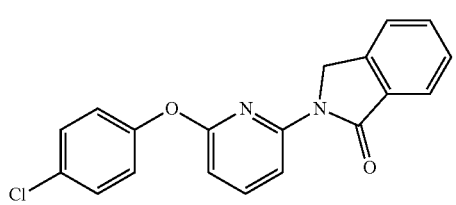 [SMILES: O=C1c2ccccc2CN1c1cccc(Oc2ccc(Cl)cc2)n1]

Compound 134 was synthesized in a manner similar to Compound 121. $^1$H NMR (DMSO-$d_6$, 400 MHz) δ 8.59-8.57 (d, 1H), 8.29 (s, 1H), 7.83-7.81 (d, 1H), 7.68-7.60 (m, 3H), 7.56-7.55 (d, 1H), 7.46-7.44 (d, 2H), 7.09-7.07 (d, 2H), 5.10 (s, 1H); LCMS (ESI): m/z 337.0 (M+H).

Example 135

Synthesis of Compound 135

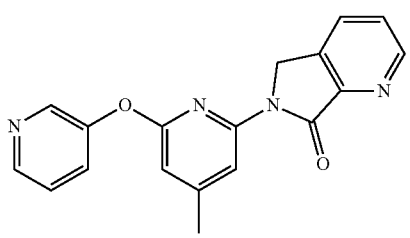 [SMILES: Cc1cc(Oc2cccnc2)nc(N2Cc3cccnc3C2=O)c1]

Compound 135 was synthesized in a manner similar to Compound 121. $^1$H NMR (DMSO-$d_6$, 400 MHz) δ 8.91 (s, 1H), 8.78-8.77 (d, 1H), 8.69-8.68 (d, 1H), 8.23 (s, 2H), 8.13-8.11 (d, 1H), 7.89-7.86 (m, 1H), 7.66-7.63 (m, 1H), 6.86 (s, 1H), 4.80 (s, 2H), 2.45 (s, 3H); LCMS (ESI): m/z 319.1 (M+H).

Example 136

Synthesis of Compound 136

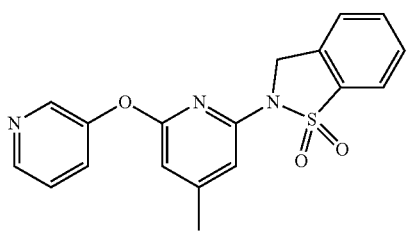

Compound 136 was synthesized in a manner similar to Compound 121. $^1$H NMR (DMSO-$d_6$, 400 MHz)) δ 8.87 (s, 1H), 8.65 (s, 1H), 8.20-8.19 (d, 1H), 7.97-7.95 (d, 1H), 7.81-7.78 (m, 2H), 7.68-7.65 (m, 2H), 6.92 (s, 1H), 6.75 (s, 1H), 4.97 (s, 2H), 2.41 (s, 3H); LCMS (ESI): m/z 354.0 (M+H).

Example 137

Synthesis of Compound 137

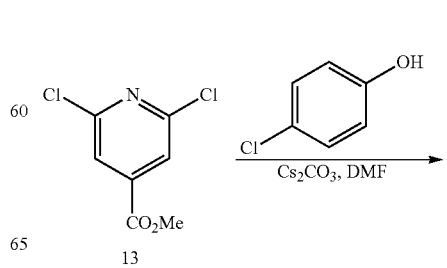

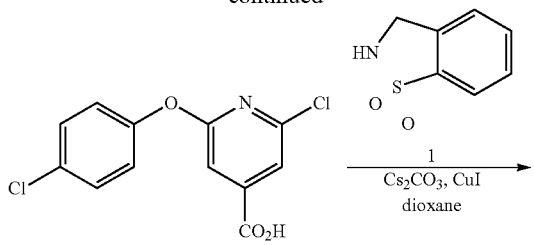

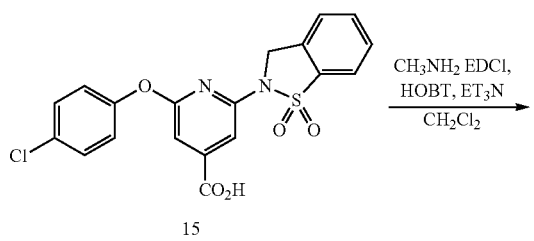

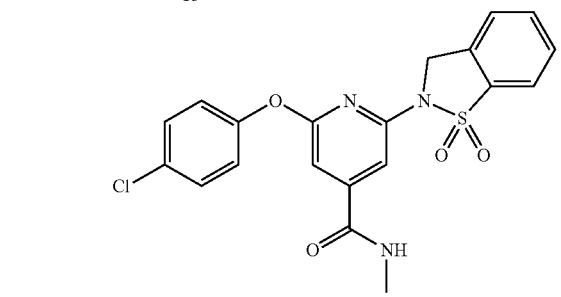

Compound 137

Step 1.

A mixture of 13 (500 mg, 2.43 mmol), 4-chlorophenol (312 mg, 2.43 mmol), Cs$_2$CO$_3$ (1.58 g, 4.85 mmol) and CsF (369 mg, 2.43 mmol) in DMF (30 mL) was degassed and purged with N$_2$ (3×). The mixture was stirred at 100° C. for 12 h, then cooled and poured into water (100 mL). The solution was extracted with ethyl acetate (3×40 mL) and the organic layer was washed with saturated brine (80 mL), dried over anhydrous sodium sulfate, filtered and concentrated. The crude material was purified by prep-TLC (petroleum ether:ethyl acetate=1:1) to provide 14 (380 mg) as a light yellow solid.

Step 2.

A mixture of 14 (200 mg, 0.70 mmol), 1 (143 mg, 0.84 mmol), Cs$_2$CO$_3$ (459 mg, 1.41 mmol), CuI (40 mg, 0.21 mmol) and 2-(dimethylamino)acetic acid hydrochloride (30 mg, 0.21 mmol) in dioxane (2 mL) was degassed and purged with N$_2$ (3×). The mixture was stirred at 100° C. for 12 h under N$_2$ atmosphere. The reaction mixture was diluted with ethyl acetate (50 mL), adjusted to pH=7 with 2N HCl, and separated. The aqueous layer was extracted with ethyl acetate (2×40 mL) and the combined organic layer was washed with saturated brine (80 mL), dried over anhydrous sodium sulfate, filtered and concentrated to give 15 (230 mg) as a light yellow solid.

Step 3.

A mixture of compound 15 (210 mg, 0.50 mmol), methylamine hydrochloride (41 mg, 0.60 mmol), EDCI (126 mg, 0.65 mmol), HOBt (89 mg, 0.65 mmol) and Et$_3$N (102 mg, 1.01 mmol) in CH$_2$Cl$_2$ (30 mL) was degassed and purged with N$_2$ (3×). The mixture was stirred at 15° C. for 12 h. The solution was extracted with water (30 mL) and saturated brine (30 mL), dried over anhydrous sodium sulfate, filtered and concentrated. The crude was purified by prep-HPLC to give Compound 137 (1045 mg, 44%) as a white solid. $^1$H NMR (DMSO-d$_6$, 400 MHz) δ 8.81 (d, 1H), 8.01 (d, 1H), 7.83-7.77 (m, 1H), 7.74-7.65 (m, 2H), 7.49 (d, 2H), 7.42 (s, 1H), 7.33 (d, 2H), 7.06 (s, 1H), 5.04 (s, 2H), 2.81 (d, 3H); LCMS (ESI): m/z 430.0 (M+H).

Example 138

Synthesis of Compound 138

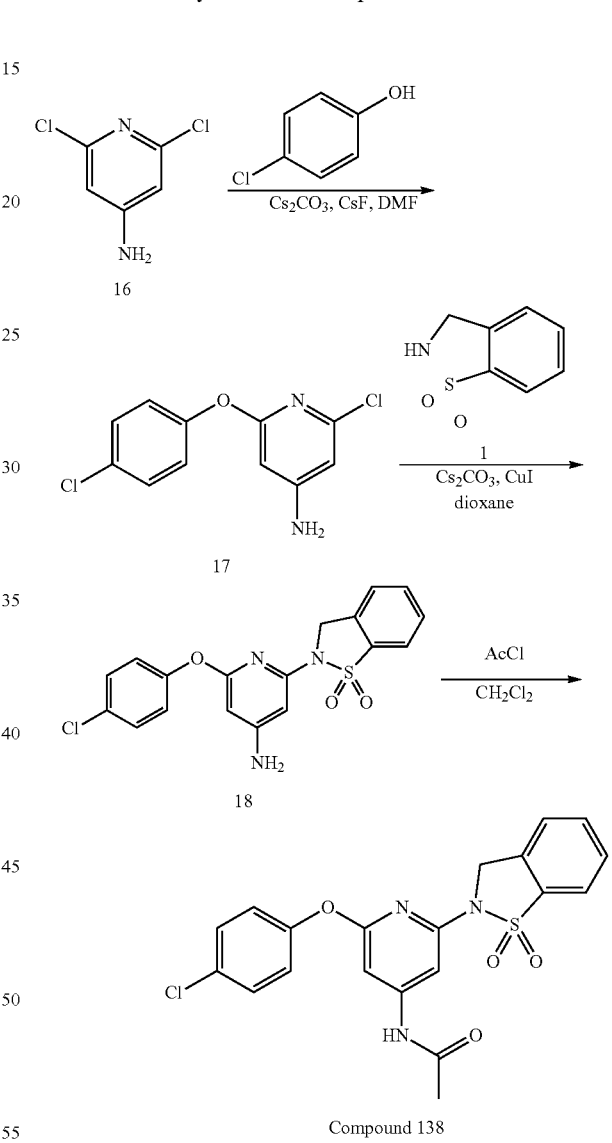

Compound 138

Step 1.

A mixture of compound 16 (500 mg, 3.07 mmol), 4-chlorophenol (394 mg, 3.07 mmol), Cs$_2$CO$_3$ (2.00 g, 6.14 mmol) and CsF (466 mg, 3.07 mmol) in DMF (8 mL) was degassed and purged with N$_2$ (3×). The mixture was stirred at 100° C. for 12 h and then poured into water (80 mL). The solution was extracted with ethyl acetate (3×40 mL) and the organic layer was washed with saturated brine, dried over anhydrous sodium sulfate, filtered and concentrated to give 17 (650 mg) as a dark brown oil.

Step 2.

A mixture of compound 17 (300 mg, 1.18 mmol), 1 (240 mg, 1.42 mmol), $Cs_2CO_3$ (769 mg, 2.36 mmol), CuI (67 mg, 0.35 mmol) and 2-(dimethylamino)acetic acid hydrochloride (49 mg, 0.354 mmol) in dioxane (20 mL) was degassed and purged with $N_2$ for (3×). The mixture was stirred at 100° C. for 12 hrs, filtered, and then diluted with ethyl acetate (50 mL). The solution was washed with saturated brine (50 mL), dried over anhydrous sodium sulfate, filtered, and concentrated to give 18 as a dark brown oil which was used without further purification.

Step 3.

To a solution of 18 (520 mg, 1.34 mmol) and $Et_3N$ (271 mg, 2.68 mmol) in $CH_2Cl_2$ (30 mL) at 0° C. was added dropwise acetyl chloride (116 mg, 1.47 mmol). The mixture was stirred at 15° C. for 2 h and then quenched with saturated brine (50 mL). The organic layer was dried over anhydrous sodium sulfate, filtered and concentrated. The crude material was purified by prep-HPLC to give Compound 138 (73 mg, 12.14%) as a white solid. $^1$H NMR (DMSO-$d_6$, 400 MHz) δ 10.58 (s, 1H), 8.06-7.97 (m, 1H), 7.83-7.77 (m, 1H), 7.74-7.64 (m, 2H), 7.49 (d, 2H), 7.41 (s, 1H), 7.28 (d, 2H), 6.98 (s, 1H), 4.98 (s, 2H), 2.08 (s, 3H); LCMS (ESI): m/z 430.0 (M+H).

Example 139

Synthesis of Compound 139

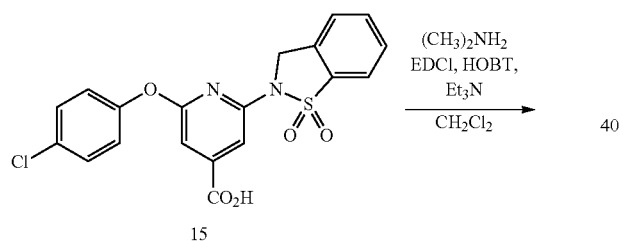

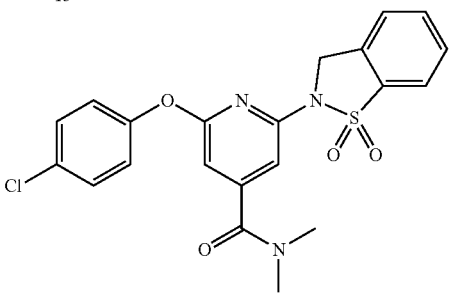

Compound 139

A mixture of 15 (210.00 mg), dimethylamine hydrochloride (49 mg, 0.60 mmol), EDCI (125 mg, 0.65 mmol), HOBt (88 mg, 0.65 umol) and $Et_3N$ (102 mg, 1.01 mmol) in $CH_2Cl_2$ (20 mL) was degassed and purged with $N_2$ (3×). The mixture was stirred at 15° C. for 12 h and then washed with water (30 mL), saturated brine (30 mL), dried over anhydrous sodium sulfate, filtered, and concentrated. The crude material was purified by prep-HPLC to give Compound 139 (13 mg, 6%) as a white solid. $^1$H NMR (DMSO-$d_6$, 400 MHz) δ 8.09 (d, 1H), 7.89-7.84 (m, 1H), 7.77-7.69 (m, 2H), 7.51 (d, 2H), 7.36 (d, 2H), 7.13 (s, 1H), 5.22 (s, 2H), 2.95 (s, 3H), 2.89 (s, 3H); LCMS (ESI): m/z 445.0 (M+H).

Example 140

Synthesis of Compound 140

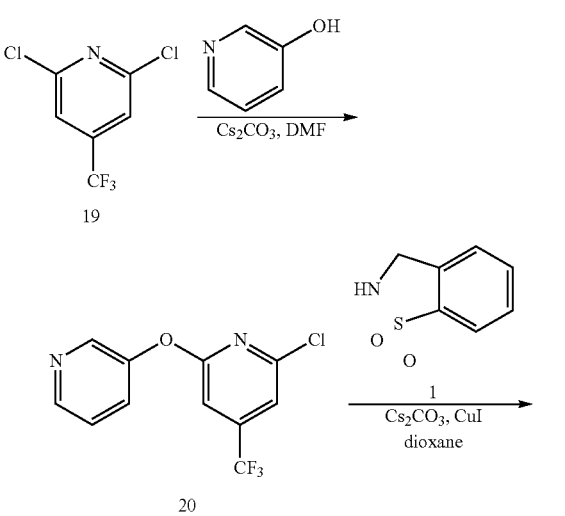

Step 1.

A mixture of 19 (120 mg, 0.56 mmol), pyridin-3-ol (53 mg, 0.56 mmol), $Cs_2CO_3$ (0.36 mg, 1.11 mmol) and CsF (84 mg, 0.56 umol) in DMF (2 mL) was degassed and purged with $N_2$ (3×). The mixture was stirred at 100° C. for 12 h and then poured into water (80 mL). The reaction mixture was extracted with ethyl acetate (3×40 mL) and the organic layer was washed with saturated brine, dried over anhydrous sodium sulfate, filtered, and concentrated to give 20 (160 mg) as a light yellow oil.

Step 2.

A mixture of 20 (160 mg, 0.58 mmol), 1 (99 mg, 0.58 mmol), $Cs_2CO_3$ (380 mg, 1.17 mmol), CuI (33 mg, 0.17 mmol) and 2-(dimethylamino)acetic acid hydrochloride (24 mg, 0.17 mmol) in dioxane (2 mL) was degassed and purged with $N_2$ (3×). The mixture was stirred at 100° C. for 12 h and then filtered and concentrated. The crude material was purified by prep-HPLC to give Compound 140 (27 mg, 10%) as a white solid. $^1$H NMR (DMSO-$d_6$, 400 MHz) δ 8.98 (s,1H), 8.74 (d, 1H), 8.34 (d, 1H), 7.99 (d, 1H), 7.92 (dd, 1H), 7.85-7.79 (m, 1H), 7.71-7.66 (m, 2H), 7.34 (s, 1H), 7.21 (s, 1H), 5.10 (s, 2H); LCMS (ESI): m/z 408.0 (M+H).

Example 141

Synthesis of Compound 141

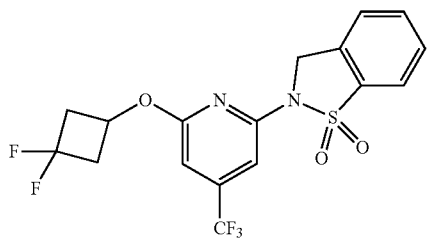 [SMILES: O=S1(=O)c2ccccc2CN1c1cc(C(F)(F)F)cc(OC2CC(F)(F)C2)n1]

Compound 141 was synthesized in a manner similar to Compound 140. $^1$H NMR (DMSO-d$_6$ 400 MHz) δ 8.05 (d, 1H), 7.88-7.82 (m, 1H), 7.77-7.68 (m, 2H), 6.99 (d, 2H), 5.22 (br. s., 2H), 5.14 (br. s., 1H), 2.80 (d, 4H); LCMS (ESI): m/z 421.0 (M+H).

Example 142

Synthesis of Compound 142

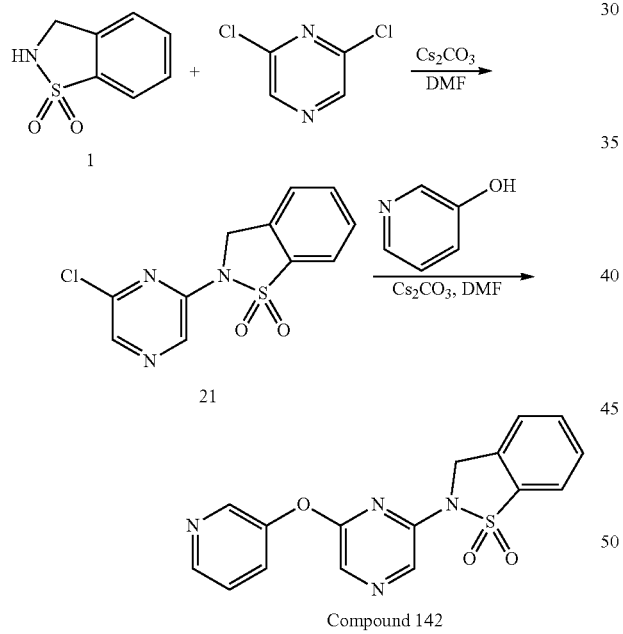

Compound 142

Step 1.

To a mixture of 2,6-dichloropyrazine (193 mg, 1.30 mmol) and 1 (200 mg, 1.18 mmol) in DMF (5 mL), was added Cs$_2$CO$_3$ (770 mg, 2.36 mmol). The resulting mixture was stirred at 100° C. for 5 hours. The mixture was cooled to 25° C. and poured into ice water. The aqueous phase was extracted with ethyl acetate (20 mL). The combined organic phase was washed with saturated brine (20 mL), dried with anhydrous Na$_2$SO$_4$, filtered, and concentrated under reduced pressure. The residue was purified by TLC (petroleum ether/ethyl acetate=2:1) to afford 21 (220 mg, 60%) as yellow solid.

Step. 2

To a mixture of 21 (220 mg, 0.78 mmol) and pyridine-3-ol (74 mg, 0.78 mmol) in DMF (3 mL), was added Cs$_2$CO$_3$ (509 mg, 1.56 mmol) in one portion. The mixture was stirred at 50° C. for 1 hour, cooled to 25° C., and then poured into water (5 mL). The aqueous phase was extracted with ethyl acetate (20 mL). The combined organic phase was washed with saturated brine (20 mL), dried with anhydrous Na$_2$SO$_4$, filtered and concentrated under reduced pressure. The residue was purified by prep-HPLC to afford Compound 142 (22 mg, 13%) as yellow solid. $^1$H NMR (DMSO-d$_6$, 400 MHz) δ 8.95 (s, 1H); 8.71-8.70 (d, 1H), 8.40-8.37 (d, 2H), 8.32-8.30 (d, 1H), 8.01-8.00 (d, 1H), 7.89-7.82 (m, 2H), 7.72-7.70 (m, 2H), 5.25-5.15 (m, 2H); LCMS (ESI+): m/z 341 (M+1).

Example 143

Synthesis of Compound 143

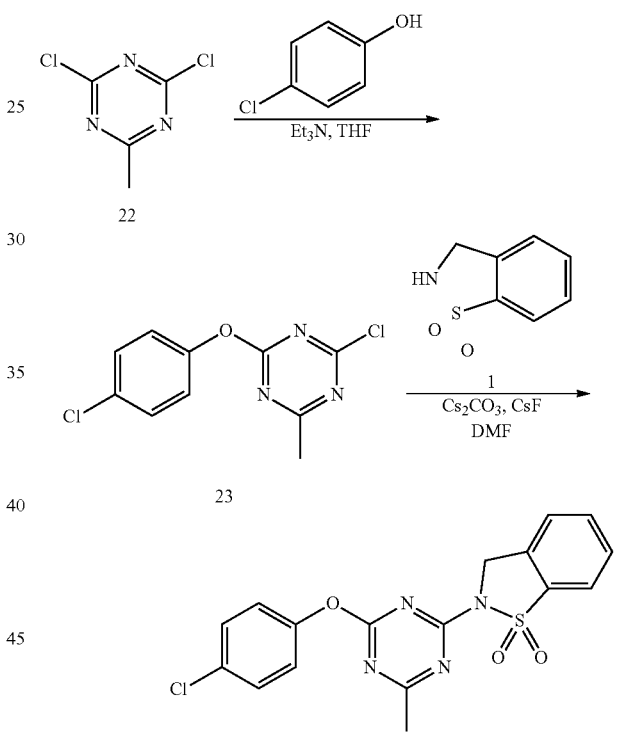

Compound 143

Step 1.

To a solution of compound 22 (100 mg, 0.61 mmol) and Et$_3$N (123 mg, 1.22 mmol) in anhydrous THF (15 mL) at 0° C. was added 4-chlorophenol (78 mg, 0.61 mmol). The mixture was stirred at 15° C. for 1 h and then concentrated to give 23 (180 mg) as a light yellow solid.

Step 2.

A mixture of 23 (180 mg, 0.70 mmol), 1 (60 mg, 0.35 mmol), CsF (107 mg, 0.70 mmol), Cs$_2$CO$_3$ (458 mg, 1.41 mmol) in DMF (3 mL) was degassed and purged with N$_2$ (3×). The mixture was stirred at 80° C. for 1 h, filtered, and then purified by prep-HPLC to give Compound 143 (15 mg, 5%) as a light yellow solid. $^1$H NMR (DMSO-d$_6$, 400 MHz) δ 7.97 (d, 1H), 7.81 (s, 1H), 7.72 (d, 1H), 7.43 (s, 1H), 7.31 (s, 2H), 7.18 (s, 2H), 5.09 (s, 2H), 2.33 (s, 3H); LCMS (ESI): m/z 356.0 (M+H).

Example 144

Synthesis of Compound 144

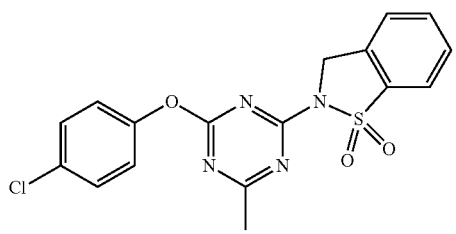 [SMILES: Cc1nc(Oc2ccc(Cl)cc2)nc(N2Cc3ccccc3S2(=O)=O)n1]

Compound 144 was synthesized in a manner similar to Compound 143. $^1$H NMR (DMSO-$d_6$, 400 MHz) δ 8.02 (d, 1H), 7.86-7.81 (m, 1H), 7.75 (d, 1H), 7.72-7.65 (m, 1H), 7.53 (d, 2H), 7.38 (d, 2H), 5.15 (br. s., 2H), 2.45 (s, 3H); LCMS (ESI): m/z 389.0 (M+H).

Example 145

Synthesis of Compound 145

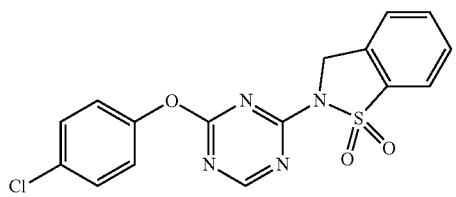 [SMILES: O=S1(=O)c2ccccc2CN1c1ncnc(Oc2ccc(Cl)cc2)n1]

Compound 145 was synthesized in a manner similar to Compound 143. $^1$H NMR (DMSO-$d_6$, 400 MHz) δ 8.86 (s, 1H), 8.04 (d, 1H), 7.88-7.81 (m, 1H), 7.79-7.67 (m, 2H), 7.54 (d, 2H), 7.40 (d, 2H), 5.17 (br. s., 2H); LCMS (ESI): m/z 375.0 (M+H).

Example 146

Synthesis of Compound 146

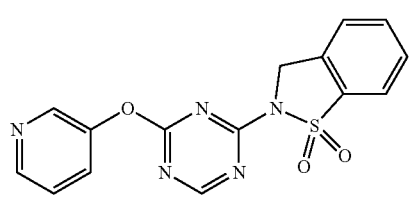 [SMILES: O=S1(=O)c2ccccc2CN1c1ncnc(Oc2cccnc2)n1]

Compound 146 was synthesized in a manner similar to Compound 143. $^1$H NMR (DMSO-$d_6$, 400 MHz) δ 8.91 (s, 1H), 8.80 (d, 1H), 8.65 (d, 1H), 8.10 (d, 1H,) 8.04 (d, 1H), 7.88-7.82 (m, 1H), 7.77-7.68 (m, 3H), 5.18 (s, 2H); LCMS (ESI): m/z 342.0 (M+H).

BIOLOGICAL EXAMPLES

Example 147

GPR120 β-Arrestin Recruitment Assay

This in vitro assay tests compounds' ability to activate intracellular signaling via β-Arrestin recruitment to heterologously expressed human GPR120. This functional cellular assay utilizes enzyme fragment complementation with β-galactosidase (β-gal) as a functional reporter (DiscoveRx PathHunter® β-Arrestin assay platform). The human GPR120 receptor (GenBank accession Number NM_181745) was fused in frame with the small enzyme fragment ProLink™ and co-expressed in CHO-K1 cells with a fusion protein of β-Arrestin 2 and the larger, N-terminal deletion mutant of β-gal. Activation by a GPR120 agonist stimulates binding of β-arrestin to the ProLink-tagged GPCR and forces complementation of the two enzyme fragments, resulting in the formation of an active β-gal enzyme. This interaction leads to an increase in enzyme activity that can be measured using chemiluminescent PathHunter® Detection Reagents.

One day prior to the assay, cells were seeded in a total volume of 20 µl of growth medium into white walled 384-well microplates and incubated at 37° C./5% $CO_2$ overnight. On the day of the assay, growth medium was removed and 20 µl assay buffer (HBSS+10 mM HEPES+ 0.1% heat-inactivated BSA) were added to each well.

Test compounds were dissolved in 100% DMSO to a concentration of 10 mM to provide stock solutions. Serial dilutions were performed from stock solutions into assay buffer to obtain intermediate concentrations of 5-fold higher than the concentrations to be tested. 5 µl of the 5× compound solutions were added to the cells and the assay plates were incubated at 37° C. for 90 minutes. The final concentration of compounds tested in the assay ranged from 1.5 nM to 100 µM. Following incubation, 12.5 µl of PathHunter® detection reagent were added to each well, and plates were incubated at room temperature for 60 minutes. Chemiluminescence was read using an EnVision plate reader (PerkinElmer), raw data were expressed as relative light units (RUT).

To determine agonist potencies (ECso values), non-linear least-squares curve fits of the raw data (RLU) were performed in the GraphPad Prism software package, using the 4-parameter model with variable Hill Slope:

$$Y = \text{Bottom} + \frac{\text{Top} - \text{Bottom}}{1 + 10^{((logEC50-x)*Hill\ Slope)}}$$

Reported below in Table 1 are $pEC_{50}$ values ($pEC_{50}$=-log($EC_{50}$) from curve fit) for compounds of Formula 1 in this assay, β-Arr pEC50. Alternatively, percent activation at a single concentration is reported.

Example 148

Human GPR120 Calcium-Release Assay

This in vitro assay tests compounds' ability to activate heterologously expressed human GPR120 via G-protein coupling leading to generation of inositol 1,4,5-triphosphate and mobilization of intracellular calcium. This functional cellular assay is based on the luminescence of mitochondrial aequorin following intracellular $Ca^{2+}$ release. Aequorin is a photoprotein isolated from the jellyfish *Aequorea victoria*. The active protein is formed in the presence of molecular oxygen from apoaequorin and its cofactor coelenterazine. Binding of $Ca^{2+}$ to the active protein induces a conformational change, resulting in oxidation of coelenterazine and subsequent blue luminescence.

The short variant of the human GPR120 receptor (GenBank accession Number AAI01176) was stably expressed in a CHO-K1 cell line coexpressing Ga16 and mitochondrial apoaequorin.

Cells were grown to mid-log phase in culture media without antibiotics, were detached with PBS/EDTA, centrifuged and resuspended in assay buffer (DMEM-F12 medium with 15 mM HEPES pH 7.0 and 0.1% protease free BSA) at a concentration of $10^6$ cells/mL. Cells were incubated at room temperature for at least 4 hours with 5 µM coelenterazine h.

Test compounds were dissolved in 100% DMSO to a concentration of 20 mM to provide stock solutions. Serial dilutions were performed from stock solutions in 100% DMSO to obtain intermediate concentrations 200-fold higher than the concentrations to be tested. Each sample was diluted 100-fold into assay buffer. 50 µl of these compound solutions were dispensed into each well of 96-well assay plates. The final concentration of compounds tested in the assay ranged from 5 nM to 100 µM. α-Linolenic acid was used as a reference compound. Each test was performed in duplicate.

To start the assay, 50 µl of cell suspension were added to each well of the assay plate. The resulting luminescence was recorded using a Hamamatsu Functional Drug Screening System 6000 (FDSS 6000), and raw data were expressed as relative light units (RLU).

To determine agonist potencies ($EC_{50}$ values), non-linear least-squares curve fits of the raw data (RLU) were performed in the GraphPad Prism software package, using the 4-parameter model with variable Hill Slope:

$$Y = Bottom + \frac{Top - Bottom}{1 + 10^{((logEC50-x)*Hill\ Slope)}}$$

Reported below in Table 1 are $pEC_{50}$ values ($pEC_{50}=-log(EC_{50})$ from curve fit) for representative compounds of Formula I in this assay, Ca2+ pEC50.

Table 1. Activity of compounds of Formula I in in vitro assays.

TABLE 1

| Compound # | β-Arr pEC50 | Ca2+ pEC50 |
| --- | --- | --- |
| 1 | 5.1 | 5.1 |
| 2 | 18% @ 10 uM | |
| 3 | <4.5 | |
| 4 | <4.5 | |
| 5 | <5.0 | |
| 6 | <5.0 | |
| 7 | 4.9 | |
| 8 | 4.9 | |
| 9 | <4.5 | |
| 10 | <4.5 | |
| 11 | <5.0 | |
| 12 | <4.5 | |
| 13 | 9% @ 10 uM | |
| 14 | 8% @ 10 uM | |
| 15 | 3% @ 10 uM | |
| 16 | 5.2 | 5.9 |
| 17 | 4% @ 10 uM | |
| 18 | <5 | |
| 19 | 5.3 | 6.1 |
| 20 | 5.2 | 5.4 |
| 21 | <5.1 | 6.3 |
| 22 | 5.8 | <4.0 |
| 23 | 5.5 | |
| 24 | 1% @ 10 uM | |
| 25 | 16% @ 10 uM | |
| 26 | 4.9 | |
| 27 | 9% @ 10 uM | |
| 28 | 4.9 | |
| 29 | 4.8 | |
| 30 | 17% @ 10 uM | |
| 31 | 11% @ 10 uM | |
| 32 | 4.6 | |
| 33 | 5.1 | <4 |
| 34 | 5.8 | 6.7 |
| 35 | 5.8 | <4.0 |
| 36 | 6.2 | 5.1 |
| 37 | 6 | 6.7 |
| 38 | 4.8 | |
| 39 | <5.0 | |
| 40 | <5.0 | |
| 41 | 5.6 | 6.1 |
| 42 | 6 | 6.5 |
| 43 | <4.5 | |
| 44 | <5.0 | 5.8 |
| 45 | 5.8 | <4.0 |
| 46 | 5.3 | |
| 47 | 5.2 | |
| 48 | <5.0 | |
| 49 | 5.6 | |
| 50 | 5.3 | 5.2 |
| 51 | 5 | 6 |
| 52 | 4.9 | |
| 53 | <5.0 | |
| 54 | <5.0 | |
| 55 | <5.0 | |
| 56 | <5.0 | 6.1 |
| 57 | 6 | |
| 58 | 5.6 | 6.2 |
| 59 | 5.2 | 4.9 |
| 60 | 5.8 | 6.3 |
| 61 | <4.5 | <4.0 |
| 62 | <5.0 | |
| 63 | 6.3 | <4.0 |
| 64 | <5.0 | |
| 65 | <5.0 | |
| 66 | <5.0 | |
| 67 | <5.0 | 5.2 |
| 68 | 5.6 | |
| 69 | 5.4 | |
| 70 | 4.8 | |
| 71 | 1% @ 10 uM | |
| 72 | <5.0 | <4.0 |
| 73 | <5.0 | |
| 74 | <4.5 | |
| 75 | <4.5 | |
| 76 | <4.5 | |
| 77 | 5.6 | 6 |
| 78 | 5.8 | 5.4 |
| 79 | 5.8 | 6.3 |
| 80 | 6.3 | 5.6 |
| 81 | 5.2 | |
| 82 | 5.6 | 5.9 |
| 83 | 5.6 | 6.1 |
| 84 | <5.0 | |
| 85 | <4.5 | |
| 86 | 6.6 | 6.4 |
| 87 | 6.1 | 5.8 |
| 88 | <5.0 | |
| 89 | 5.6 | 4.7 |
| 90 | 4.9 | |
| 91 | 5.4 | |
| 92 | 5.5 | |
| 93 | 5.1 | 6.2 |
| 94 | <5.0 | |
| 95 | 6.4 | |

TABLE 1-continued

| Compound # | β-Arr pEC50 | Ca2+ pEC50 |
|---|---|---|
| 96 | 6 | <5.0 |
| 97 | 6.2 | 6 |
| 98 | 6.1 | 5.6 |
| 99 | 6.3 | 6.8 |
| 100 | 6.8 | |
| 101 | 6.4 | <7.0 |
| 102 | 6.1 | |
| 103 | 5.7 | |
| 104 | 5.4 | |
| 105 | 5.6 | |
| 106 | 6 | 6.7 |
| 107 | 6.1 | |
| 108 | <4.5 | |
| 109 | <4.5 | |
| 110 | <4.5 | |
| 111 | <5.0 | |
| 112 | <4.5 | |
| 113 | 4.9 | |
| 114 | 4.9 | 4.8 |
| 115 | 5.2 | |
| 116 | 4.4 | |
| 117 | <5 | |
| 118 | 6 | |
| 119 | 4.5 | |
| 120 | <4.5 | |
| 121 | 5.8 | 6.7 |
| 122 | <5 | 6.3 |
| 123 | <4.5 | <4.0 |
| 124 | <4.5 | |
| 125 | <4.5 | <5.0 |
| 126 | <4.5 | |
| 127 | <4.5 | |
| 128 | 7.4 | 7.1 |
| 129 | <4.5 | |
| 130 | <4.5 | |
| 131 | 6.8 | 6.5 |
| 132 | <4.5 | |
| 133 | <4.5 | |
| 134 | 5 | |
| 135 | <5.0 | |
| 136 | 6.2 | |
| 137 | 5.6 | |
| 138 | 5.5 | |
| 139 | <5.0 | |
| 140 | 6 | |
| 141 | 5.2 | |
| 142 | 4.4 | 5.9 |
| 143 | <4.5 | |
| 144 | 5.7 | |
| 145 | 5.1 | |
| 146 | 4.8 | |

The results above show that the compounds of the invention, as illustrated in the examples above and generally as defined by Formula 1, are potent GRP120 agonists that will find application in the treatment of T2D. While, as disclosed in the detailed description above, these compounds can be administered via any route of administration and at various frequencies, in one preferred embodiment, they are administered once a day to T2D patients for treatment and control of that condition in the form of a tablet or capsule, taken orally.

Example 149

GPR120 C57BL/6J Mouse Oral Glucose Tolerance Test

An oral glucose tolerance test (OGTT) was performed with certain compounds to determine their acute effect on glucose excursions.

Male C57BL/6J mice aged 8-10 weeks and kept on a regular chow diet were used for the study. 10 Mice were used per treatment group, with individual mice weighing in the range of 24-30 grams on study day, and a mean weight of 27.2-27.3 grams for each treatment group.

Test articles were prepared as suspensions in dosing vehicle (0.5% hydroxypropyl methylcellulose and 2% Tween-20 in water) at a concentration of 10 mg/mL by mixing and sonication.

The mice were fasted for 6 hours prior to dosing of vehicle or test articles at 100 mg/kg (10 mL/kg) by oral gavage. Glucose was dosed (PO) at 3 g/kg 30 min after dosing of test articles. Animals were bled via tail snip to determine basal glucose levels 30 min prior to the glucose challenge, and again at 0, 15, 30, 60, 90 and 120 minutes following the glucose challenge. A Johnson & Johnson OneTouch Glucometer was used to determine glucose levels in all blood samples.

Glucose values were entered into an Excel sheet, and mean values±standard error of the mean were graphed in GraphPad Prism. Significance of difference between groups was analyzed by performing two-way RM ANOVA for the time course study. P values less than 0.05 were considered statistically significant.

The ability of compounds of this invention to inhibit TNFα production was assessed by using human peripheral blood mononuclear cells (hPBMC) which synthesize and secrete TNFα when stimulated with lipopolysaccharide (LPS).

Mononuclear Cell packs collected by and purchased from Key Biologics were used for the preparation of hPBMC. Briefly, cell product was sterilely removed from the phoresis bag, carefully layered onto pre-warmed Ficoll (Histopaque 1077) and centrifuged at 1,800×g for 15 minutes at room temperature with the brake off. Following centrifugation, the interface was removed and added to sterile Dulbecco's Phosphate Buffered Saline (DPBS). The cells were then pelleted at 300×g for ten minutes at room temperature. The cells were resuspended in fresh DPBS then repelleted to minimize platelet contamination. The subsequent pellet was resuspended in DPBS and the cells counted. Cells were repelleted and then cryopreserved at $1\times10^8$ cells per ml in DMEM/30% FBS/10% DMSO. For all hPBMC preparations, individual donors were kept separate throughout the entire process. For the assay, hPBMC were seeded into flat-bottom 96-well plates at 500,000 cells/well in 80 μl assay medium (DMEM, 0.1% FBS, 1% penicillin/streptomycin) and allowed to recover in a 37° C. incubator for one hour before the addition of compounds.

Compounds were solubilized from powder as 20 mM stocks with 100% DMSO and then serially diluted into assay medium to prepare 10× stocks to achieve five concentrations (100 μM, 30 μM, 10 μM, 3 μM and 1 μM) in the assay. All compound dilutions were added to the plates containing hPBMC (10 μl in final assay volume of 100 μl) and incubated at 37° C. for an hour before the addition of stimulus. Control wells received 10 μl vehicle (media containing 5% DMSO).

For the LPS challenge, a 1 mg/ml stock solution of lipopolysaccharide (LPS) was diluted 1000-fold into assay medium (10 μl LPS+10 ml media). All wells except the "Unstimulated" control wells received 10 μl of LPS. The "Unstimulated" control wells received 10 μl media. The plates were incubated for 4 hours at 37° C. After 4 hours, the plates were centrifuged at 1,200 rpm for 5 minutes and culture media supernatants were collected into fresh 96-well plates.

TNFα levels in culture supernatants were determined by immunoassay using the Meso Scale Diagnostics electrochemiluminescent immunoassay system. Meso Scale V-plex 96-well plates (Meso Scale Diagnostics, Rockville, Md.) were used for detection of TNFα as directed by the manufacturer (overnight incubation protocol). Samples were diluted 100-fold. TNFα concentrations were determined by interpolating against a standard curve and then multiplying by 100 to arrive at "pg/ml" values. TNFα release was reported as % of vehicle treated LPS stimulated cells.

While certain embodiments have been illustrated and described, it will be understood that changes and modifications can be made therein in accordance with ordinary skill in the art without departing from the present invention in its broader aspects as defined in the following claims.

REFERENCES

1. Data for diabetes: World Health Organization, Fact Sheet No. 312 (http://www.who.int/mediacentre/factsheets/fs312/en/)
2. Hirasawa et al. *Nat. Med.* 2005, 11:90-94.
3. Oh et al. *Cell* 2010, 142:687-698.
4. Ichimura et al. *Nature* 2012, 483:350-354.
5. Cornall et al. *Drug Disc. Today* 2014, 19:670-679.
5a. Nobili et al. *PLOSone* 2014, 9: e88005.
6a. Wellhauser et al. *J Neuroinflamm* 2014, 11: 60.
7a. Dragano et al. *J Neuroinflamm* 2017, 17:91.
8a. Heneka et al. *Nature* 2013, 493: 674.
9a. Yan et al. *Immunity* 2013, 38: 1154.
10a. Tan et al. *Cell Death Dis* 2014, 5: e1382.
11a. Kaushal et al. *Cell Death Differentiation* 2015, 22: 1676.
6. Suzuki et al. *J. Med. Chem.* 2008, 51:7640-7644.
7. Hara et al. *Naunyn Schmied. Arch. Pharmacol.* 2009, 380:247-255.
8. Shimpukade et al. *J. Med. Chem.* 2012, 55:4511-4515.
9. Hudson et al. *Mol Pharmacol.* 2013, 84:710-725.
10. Oh et al. *Nat. Med.* 2014, 20:942-947.
11. Sparks et al. *Bioorg. Med. Chem. Lett.* 2014, 24:3100-3103.
12. Tanaka et al. *Naunyn-Schmiedeberg's Arch Pharnacol.* 2008, 377:523-527.
13. Lu et al. *Am. J. Gastrointest. Liver Physiol.* 2012, 303:G367-G376.
14. Suckow et al. *J. Bio. Chem.* 2014, 289: 15751-15763.
15. US 20080167378
16. WO 2008066131
17. WO 2008103501
18. WO 2008139987
19. WO 2009147990
20. US 20100130559
21. WO 2010048207
22. WO 2010080537
23. WO 2011159297
24. US 20110313003
25. WO 2013139341
26. WO 2014069963
27. US 20140275172
28. US 20140275179
29. WO 20140275182
30. WO 2014059232
31. WO 2014159794
32. US 20140275173
33. WO 2010104195

The invention claimed is:

1. A compound of formula II:

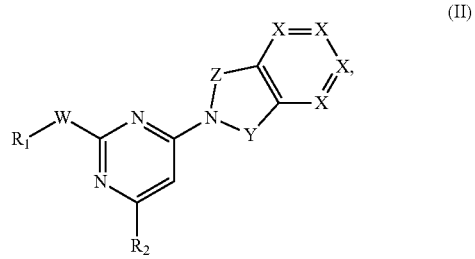

or a pharmaceutically acceptable salt thereof, wherein:
W is O;
each X independently is CH, $CR_3$ or N wherein $R_3$ is halogen, alkyl, alkoxy, or CN;
Y is $SO_2$, CO, $CH_2$, —$C(CH_3)_2$—, or —$CH(CH_3)$—;
Z is —$CH_2$—, —$CH(CH_3)$—, —$C(CH_3)_2$—, or —$C(CH_2CH_2)$—;
$R_1$ is an unsubstituted alkyl, a substituted alkyl, an unsubstituted 3-7 membered cycloalkyl, a substituted 3-7 membered cycloalkyl, an unsubstituted heterocyclyl, a substituted heterocyclyl, unsubstituted aryl, a substituted aryl, an unsubstituted heteroaryl or a substituted heteroaryl; and
$R_2$ is H, halogen, CN, $OCH_3$, $OCF_3$, NHAc, an unsubstituted alkyl, a substituted alkyl, an unsubstituted amido, a substituted amido, an unsubstituted cycloalkyl, a substituted cycloalkyl, an unsubstituted heterocyclyl, a substituted heterocyclyl, an unsubstituted aryl, a substituted aryl, an unsubstituted heteroaryl, or a substituted heteroaryl.

2. The compound of claim 1, wherein $R_1$ is selected from the group of:

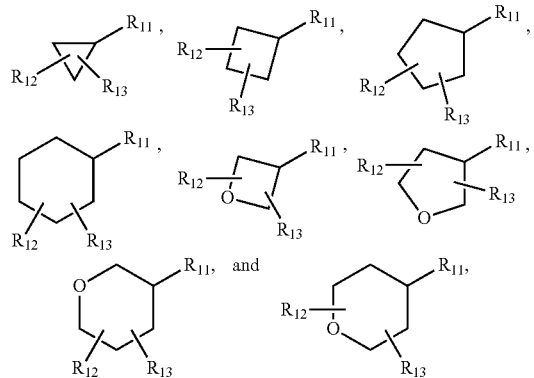

wherein, Ru is the point of attachment to W and $R_{12}$ and $R_{13}$ are independently H, $CH_3$, $CF_3$, or F.

3. The compound of claim 1, wherein $R_1$ is selected from the group of:

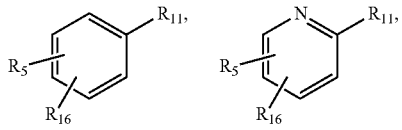

-continued

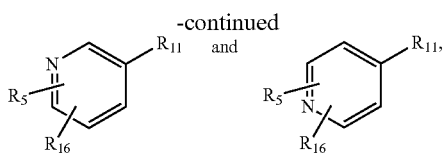

wherein, $R_{11}$ is the point of attachment to W and $R_{15}$ is H, halogen, alkyl, $CF_3$, $OCH_3$, $OCF_3$, or CN, and $R_{16}$ is H, halogen, alkyl, $CF_3$, $OCH_3$, $OCF_3$, CN, $NHCOR_{14}$, or $N(CH_3)COR_{14}$ wherein $R_{14}$ is alkyl, cycloalkyl, aryl or heteroaryl.

4. The compound of claim 1, wherein $R_1$ is selected from the group of:

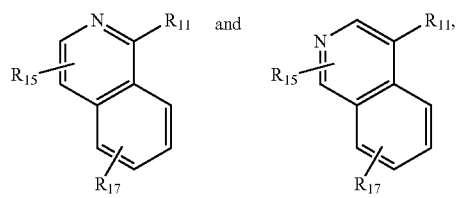

wherein Ru is the point of attachment to W and $R_{15}$ and $R_{17}$ are independently H, halogen, alkyl, $CF_3$, $OCH_3$, $OCF_3$, or CN.

5. A compound of formula III:

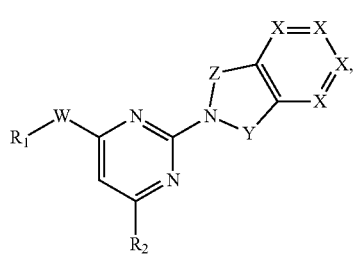

(III)

wherein:

W is O;

each X independently is CH, $CR_3$ or N wherein $R_3$ is halogen, alkyl, alkoxy, CN;

Y is $SO_2$, CO, $CH_2$, $—C(CH_3)_2—$, or $—CH(CH_3)—$;

Z is $—CH_2—$, $—CH(CH_3)—$, $—C(CH_3)_2—$, or $—C(CH_2CH_2)—$;

$R_1$ is an unsubstituted alkyl, a substituted alkyl, an unsubstituted 3-7 membered cycloalkyl, a substituted 3-7 membered cycloalkyl, an unsubstituted heterocyclyl, a substituted heterocyclyl, an unsubstituted aryl, a substituted aryl, an unsubstituted heteroaryl or a substituted heteroaryl; and $R_2$ is H, halogen, CN, $OCH_3$, $OCF_3$, NHAc, an unsubstituted alkyl, a substituted alkyl, an unsubstituted amido, a substituted amido, an unsubstituted cycloalkyl, a substituted cycloalkyl, unsubstituted heterocyclyl, a substituted heterocyclyl, an unsubstituted aryl, a substituted aryl, an unsubstituted heteroaryl, or a substituted heteroaryl.

6. The compound of claim 5, wherein $R_1$ is selected from the group of:

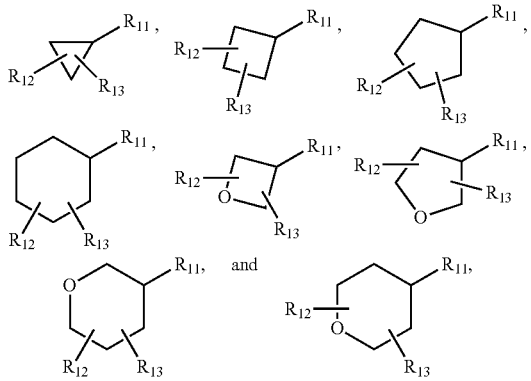

wherein, $R_{11}$ is the point of attachment to W and $R_{12}$ and $R_{13}$ are independently H, $CH_3$, $CF_3$, or F.

7. The compound of claim 5, wherein $R_1$ is selected from the group of:

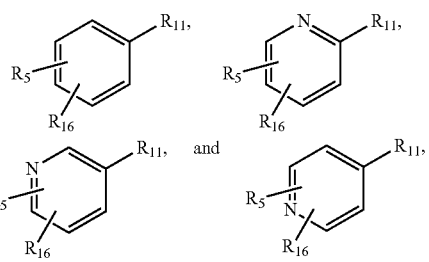

wherein, $R_{11}$ is the point of attachment to W and $R_{15}$ is H, halogen, alkyl, $CF_3$, $OCH_3$, $OCF_3$, or CN, and $R_{16}$ is H, halogen, alkyl, $CF_3$, $OCH_3$, $OCF_3$, CN, $NHCOR_{14}$, or $N(CH_3)COR_{14}$ wherein $R_{14}$ is alkyl, cycloalkyl, aryl or heteroaryl.

8. The compound of claim 5, wherein $R_1$ is selected from the group of:

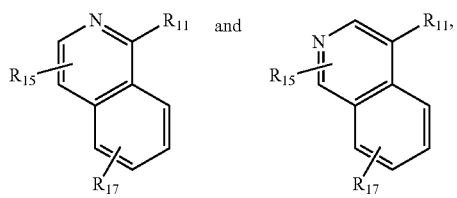

wherein Ru is the point of attachment to W and $R_{15}$ and $R_{17}$ are independently H, halogen, alkyl, $CF_3$, $OCH_3$, $OCF_3$, or CN.

9. A pharmaceutical composition comprising the compound of claim 1 and a pharmaceutically acceptable excipient.

10. A pharmaceutical composition comprising the compound of claim 5 and a pharmaceutically acceptable excipient.

* * * * *

UNITED STATES PATENT AND TRADEMARK OFFICE
CERTIFICATE OF CORRECTION

PATENT NO. : 11,548,886 B2  
APPLICATION NO. : 16/998660  
DATED : January 10, 2023  
INVENTOR(S) : Brian Raimundo et al.

Page 1 of 2

It is certified that error appears in the above-identified patent and that said Letters Patent is hereby corrected as shown below:

In the Claims

At Column 104, Line 56 - "Ru" should be replaced with "$R_{11}$".

At Column 104, Line 65 - " 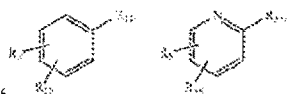 " should be replaced with " 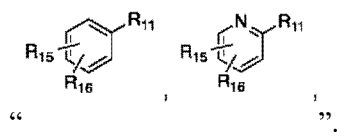 ".

At Column 105, Line 5 - " 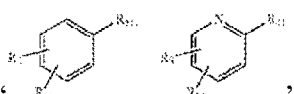 " should be replaced with -- 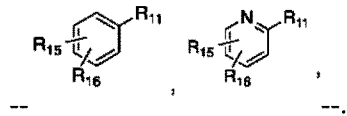 and 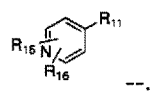 --.

At Column 105, Line 26 - "Ru" should be replaced with "Rn".

At Column 106, Line 26 - " should be replaced with -- ; -- .

Signed and Sealed this  
Twenty-eighth Day of March, 2023

Katherine Kelly Vidal  
*Director of the United States Patent and Trademark Office*

CERTIFICATE OF CORRECTION (continued)
U.S. Pat. No. 11,548,886 B2

At Column 106, Line 31 - 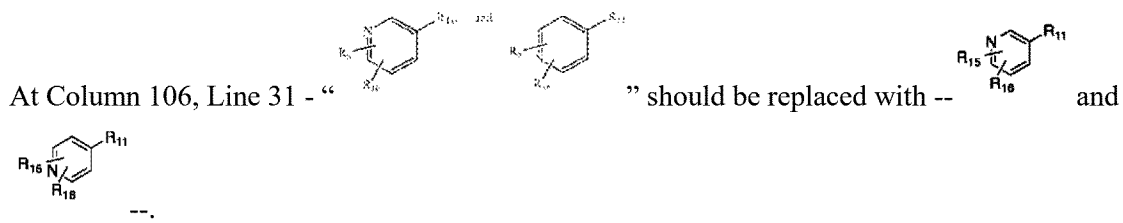 should be replaced with --

At Column 106, Line 54 - "Ru" should be replaced with "$R_{11}$".